(12) United States Patent
Miyamoto et al.

(10) Patent No.: US 10,098,962 B2
(45) Date of Patent: Oct. 16, 2018

(54) GLYCOSAMINOGLYCAN DERIVATIVE AND METHOD FOR PRODUCING SAME

(71) Applicant: Seikagaku Corporation, Tokyo (JP)

(72) Inventors: Kenji Miyamoto, Tokyo (JP); Yosuke Yasuda, Tokyo (JP); Hisayuki Takeuchi, Tokyo (JP); Keiji Yoshioka, Tokyo (JP)

(73) Assignee: Seikagaku Corporation, Tokyo (JP)

( * ) Notice: Subject to any disclaimer, the term of this patent is extended or adjusted under 35 U.S.C. 154(b) by 219 days.

(21) Appl. No.: 14/903,817

(22) PCT Filed: Jul. 10, 2014

(86) PCT No.: PCT/JP2014/068512
§ 371 (c)(1),
(2) Date: Jan. 8, 2016

(87) PCT Pub. No.: WO2015/005458
PCT Pub. Date: Jan. 15, 2015

(65) Prior Publication Data
US 2016/0151506 A1 Jun. 2, 2016

(30) Foreign Application Priority Data
Jul. 10, 2013 (JP) .................. 2013-144364

(51) Int. Cl.
| | |
|---|---|
| *A61K 31/192* | (2006.01) |
| *A61K 31/196* | (2006.01) |
| *A61K 31/405* | (2006.01) |
| *A61K 31/573* | (2006.01) |
| *A61K 47/48* | (2006.01) |
| *A61K 47/36* | (2006.01) |
| *C08B 37/00* | (2006.01) |
| *C08B 37/08* | (2006.01) |
| *A61K 47/61* | (2017.01) |

(52) U.S. Cl.
CPC ........ *A61K 47/4823* (2013.01); *A61K 31/192* (2013.01); *A61K 31/196* (2013.01); *A61K 31/405* (2013.01); *A61K 31/573* (2013.01); *A61K 47/36* (2013.01); *A61K 47/61* (2017.08); *C08B 37/0069* (2013.01); *C08B 37/0072* (2013.01)

(58) Field of Classification Search
None
See application file for complete search history.

(56) References Cited

U.S. PATENT DOCUMENTS

| | | | |
|---|---|---|---|
| 4,489,065 A * | 12/1984 | Walton ................. | A61K 31/715 514/34 |
| 6,458,347 B1 | 10/2002 | Sugawara et al. | |
| 6,548,347 B2 * | 4/2003 | Juengling ......... | H01L 27/10873 257/E21.654 |
| 2004/0157810 A1 | 8/2004 | Teicher et al. | |
| 2006/0116346 A1 | 6/2006 | De Luca et al. | |
| 2008/0221062 A1 | 9/2008 | Miyamoto et al. | |
| 2009/0118348 A1 | 5/2009 | Miyamoto et al. | |
| 2010/0056488 A1 | 3/2010 | Teicher et al. | |
| 2011/0083991 A1 | 4/2011 | Miyamoto et al. | |

FOREIGN PATENT DOCUMENTS

| | | |
|---|---|---|
| EP | 1710257 A1 | 10/2006 |
| JP | H05-39306 A | 2/1993 |
| JP | 2006-504747 A | 2/2006 |
| JP | 4792294 B2 | 10/2011 |
| WO | 9635721 A1 | 11/1996 |
| WO | 9738727 A1 | 10/1997 |
| WO | 1999/059603 A1 | 11/1999 |
| WO | 2004/0157810 A2 | 3/2004 |
| WO | 2005/066214 A1 | 7/2005 |
| WO | 2007/004675 A1 | 1/2007 |

OTHER PUBLICATIONS

Onishi, Chem.Pharm. Bull. 61(9) 902-912 (2013). (Year: 2013).*
International Search Report issued in PCT/JP2014/068512 dated Sep. 16, 2014 (4 pages).
Written Opinion of the International Searching Authority issued in PCT/JP2014/068512 dated Sep. 16, 2014 (6 pages).
Xin, D. et al.; "The Use of Amino Acid Linkers in the Conjunction of Paclitaxel with Hyalurionic Acid as Drug Delivery System: Synthesis, Self-Assembled Property, Drug Release, and In Vitro Efficiency"; Pharmaceutical Research, vol. 27, Oct. 30, 2009, pp. 380-389 (10 pages).
Office Action issued in corresponding Japanese Application No. 2016-114657 dated May 23, 2017, and English translation thereof (5 pages).
"Controlled Release from Glycosaminoglycan Drug Complexes", Sparer, Randall V., et al. Case Western Reserve University, XP009025950; Chapter 6, pp. 107-119 (14 pages).
"Preparation and in vitro properties of a chondroitin sulfate-prednisolone conjugate" Matsuyama, Mototaka, et al., Department of Drug Delivery Research, Hoshi University, Section P24-12 of the APSTJ (The Academy of Pharmaceutical Science and Technology, Japan) journal, pp. 207 (8 pages).
Extended European Search Report issued in European Patent Application No. 14822727.5 dated Jan. 20, 2017 (7 pages).
Yoshinobu Shiose et al.; "Systematic Research of Peptide Spacers Controlling Drug Release from Macromolecular Prodrug System, Caeboxymethyldextran Polyalcohol—Peptide—Drug Conjugates"; 2009 American Chemical Society, Bioconjugate Chem. pp. 60-70; Published on web Dec. 18, 2008.

(Continued)

Primary Examiner — Layla D Berry
(74) Attorney, Agent, or Firm — Osha Liang LLP

(57) ABSTRACT

The present invention provides a glycosaminoglycan derivative in which a group derived from glycosaminoglycan and a group derived from a physiologically active substance having at least one of a carboxy group and a hydroxy group are coupled by covalent bond with a spacer therebetween, in which the spacer is selected in accordance with the decomposition rate of the covalent bond to the group derived from the physiologically active substance.

10 Claims, 6 Drawing Sheets

(56) References Cited

OTHER PUBLICATIONS

Andrei Ponta et al.; "PEG—poly (amino acid) Block Copolymer Micelles for Tunable Drug Release"; 2010 Springer Science + businee Media, LLC. Pharm Res 27: pp. 2330-2342.

Sitnikov N S et al: "Antitumor liposomes bearing a prodrug of combretastatin A-4 and a tetrasaccharide ligand of selectins", Russian Chemical Bulletin, Kluwer Academic Publishers-Plenum Publishers, NE, vol. 59, No. 12, May 19, 2011, p. 2290-2296, XP019905575, ISSN: 1573-91 71, DOI: 10.1 007IS11172-010-0390-Y.

Dan-Qi Chen et al: "Novel liver-specific cholic acid-cytarabine conjugates with potent antitumor activities: Synthesis and biological characterization", Acta Pharmacologica Sinica, vol. 32, No. 5, Apr. 25, 2011, pp. 664-672, XP055443759, GB ISSN: 1671-4083, DOI: 10.1 038Iaps.2011.7.

Haihua Xiao et al: "Biodegradable polymer cisplatin(1V) conjugate as a pro-drug of cisplatin(II)", Biomaterials, Elsevier Science Publishers BV., Barking, GB, vol. 32, No. 30,Jun. 28, 2011 (Jun. 28, 2011), pp. 7732-7739, XP028261601, ISSN: 0142-9612, DOI: 10.1 01 6IJ.BIOMATERIALS.2011.06.072.

Office Action issued in corresponding EP Application No. 14822727.5 dated Jan. 31, 2018 (6 pages).

Office Action is corresponding JP Application No. 2015-526416 with English translation dated Mar. 6, 2018 (8 pages).

Hiraku Onishi et al._Chondroitin sulfate using glycine as a linker—in vivo assessment of prednisolone The 29th Annual Meeting of the Japan Society of Drug Delivery System_Jun. 5, 2013_p. 186 (4 pages).

\* cited by examiner

GLYCOSAMINOGLYCAN DERIVATIVE AND METHOD FOR PRODUCING SAME

TECHNICAL FIELD

The present invention relates to a glycosaminoglycan derivative and a method for producing it.

BACKGROUND ART

Glycosaminoglycan (hereinbelow, also referred to as "GAG") is a compound present in a living body, and there are many examples in which glycosaminoglycan is used for a drug or a medical device. Currently, several techniques of applying a glycosaminoglycan derivative (hereinbelow, also referred to as "GAG derivative") in which a drug is chemically introduced to GAG for application to a drug or a medical device are known (see, JP 4792294 B1 and WO 99/59603 A, for example).

There can be several objects for introducing a drug to GAG, i.e., (1) delivery to a target site is achieved by using GAG as a carrier, (2) the drug is maintained and released in an affected part by using polymeric GAG, and (3) the activity, pharmaceutical effect, or the like of GAG itself is utilized, or the like.

Although it can be applied to various kinds of disorders, depending on the type of a disorder, there can be a disorder which requires early release of a drug, a disorder which requires release of a drug for a long period of time, or a disorder which requires complex release rate that lies between them.

CITATION LIST

Patent Literatures

Patent Literature 1: JP 4792294 B1
Patent Literature 2: WO 99/59603 A

SUMMARY OF INVENTION

Problem to be Solved by the Invention

When a drug-introduced GAG derivative with slow drug release rate is administered to an affected part which is believed to require release of a drug in a relatively early stage, the drug-introduced GAG derivative is metabolized and discharged even before introduction of the drug at the appropriate time, and thus it becomes useless. On the contrary, when a drug-introduced GAG derivative having fast drug release rate is administered to an affected part which is believed to require release of a drug for a relatively long period of time, it is not expected to have a continuous therapeutic effect for an extended period of time.

However, the drug-introduced GAG derivative which has been developed until now can exhibit the effect only when the release rate required for an application area and the property of the compound coincide accidently, and no attempt has been made to control actively the release rate.

Accordingly, an object of the present invention is to provide a drug-introduced glycosaminoglycan derivative enabling dissociation of introduced drug at a rate that is appropriate for a disorder for application as the drug dissociation rate can be controlled without significantly depending on a structure of a drug, and a method for producing the drug-introduced glycosaminoglycan derivative.

Means for Solving the Problem

Considering the object described above, the inventors of the present invention conducted intensive studies to develop a drug-introduced glycosaminoglycan derivative which can dissociate a drug at an appropriate rate in accordance with a disorder. As a result of introducing a drug (hereinbelow, it is also referred to as a "physiologically active substance") to GAG via a spacer and carrying out determinations on various structures of a spacer, it was found that the drug dissociation rate can be controlled without significantly depending on a structure of a drug. The present invention is completed accordingly. Namely, specific means for solving the problems described above are as follows.

<1> A method for controlling dissociation rate of a physiologically active substance from a glycosaminoglycan derivative, the method including selecting a spacer included in a glycosaminoglycan derivative, in which a group derived from glycosaminoglycan and a group derived from a physiologically active substance having at least one of a carboxy group and a hydroxy group are coupled by covalent bond with a spacer therebetween, in accordance with decomposition rate of the covalent bond between the group derived from a physiologically active substance and the spacer.

<2> A glycosaminoglycan derivative containing a group derived from glycosaminoglycan and a group derived from a physiologically active substance having at least one of a carboxy group and a hydroxy group, which are coupled by covalent bond with a spacer therebetween, in which the spacer is selected in accordance with the decomposition rate of the covalent bond to the group derived from a physiologically active substance.

<3> The glycosaminoglycan derivative described in <2>, in which the glycosaminoglycan is at least one selected from the group consisting of chondroitin sulfate, hyaluronic acid, heparin, heparan sulfate, keratan sulfate, dermatan sulfate, and a derivative thereof.

<4> The glycosaminoglycan derivative described in <2> or <3>, in which the physiologically active substance is at least one selected from the group consisting of a nonsteroidal anti-inflammatory drug, steroid, an anti-rheumatic drug, an anti-allergic drug, a therapeutic agent for hyperlipidemia, and a β stimulator.

<5> The glycosaminoglycan derivative described in any one of <2> to <4>, in which the group derived from a physiologically active substance and the spacer are covalently bonded through an ester bond.

<6> The glycosaminoglycan derivative described in any one of <2> to <5>, in which the group derived from glycosaminoglycan and the spacer are covalently bonded through an amide bond.

<7> The glycosaminoglycan derivative described in any one of <2> to <6>, in which the spacer is a divalent or higher valent group that is derived from at least one compound selected from the group consisting of amino alcohol, an amino acid, and a derivative thereof.

<8> The glycosaminoglycan derivative described in any one of <2> to <7>, in which the spacer is a divalent group derived from an amino acid represented by the following formula (I):

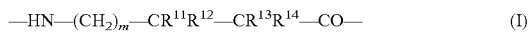

$$-HN-(CH_2)_m-CR^{11}R^{12}-CR^{13}R^{14}-CO- \quad (I)$$

(in the formula, m is an integer of 0 to 12. $R^{11}$ to $R^{14}$ each independently represent a hydrogen atom, an electron withdrawing group, an electron donating group, or a sterically hindered group).

<9> The glycosaminoglycan derivative described in any one of <2> to <7>, in which the spacer is a divalent group derived from amino alcohol represented by the following formula (II):

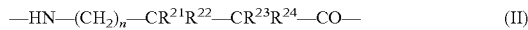

(in the formula, n is an integer of 0 to 12. $R^{21}$ to $R^{24}$ each independently represent a hydrogen atom, an electron withdrawing group, an electron donating group, or a sterically hindered group).

<10> The glycosaminoglycan derivative described in any one of <2> to <7>, in which the spacer is a divalent or higher valent group that is derived from at least one amino acid selected from the group consisting of glycine, alanine, leucine, isoleucine, valine, serine, threonine, asparaginic acid, glutamic acid, asparagine, glutamine, arginine, lysine, histidine, tryptophan, phenylalanine, tyrosine, methionine, cysteine, proline, β-alanine, and a derivative thereof, or a divalent or higher valent group that is derived from at least one amino alcohol selected from the group consisting of aminopropanol, aminoethanol, and a derivative thereof.

<11> A pharmaceutical composition containing the glycosaminoglycan derivative described in any one of <2> to <10>.

<12> A controlled release preparation containing the glycosaminoglycan derivative described in any one of <2> to <10>.

<13> A continuous type pain suppressing agent containing the glycosaminoglycan derivative described in any one of <2> to <10>.

<14> A method for producing a glycosaminoglycan derivative, the method including preparing a physiologically active substance having at least one of a carboxy group and a hydroxy group, selecting a spacer for forming a covalent bond with a group derived from a physiologically active substance in accordance with decomposition rate of the covalent bond, and forming a covalent bond between the group derived from a physiologically active substance and a group derived from glycosaminoglycan with the spacer therebetween.

<15> A glycosaminoglycan derivative containing a group derived from glycosaminoglycan and a group derived from a physiologically active substance having at least one of a carboxy group and a hydroxy group which are coupled by covalent bond with a spacer therebetween, in which
the glycosaminoglycan is chondroitin sulfate or hyaluronic acid,
the physiologically active substance is a nonsteroidal anti-inflammatory drug,
the group derived from a physiologically active substance and the spacer are covalently bonded through an ester bond,
the group derived from glycosaminoglycan and the spacer are covalently bonded through an amide bond, and
the spacer is a divalent group derived from amino alcohol represented by the following formula (II):

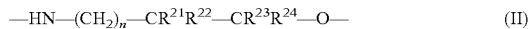

(in the formula, n is an integer of 0 to 12. $R^{21}$ to $R^{24}$ each independently represent a hydrogen atom or a sterically hindered group).

<16> The glycosaminoglycan derivative described in <15>, in which the physiologically active substance is diclofenac.

<17> The glycosaminoglycan derivative described in <15> or <16>, in which one or two or more of $R^{21}$ to $R^{24}$ is a sterically hindered group.

<18> The glycosaminoglycan derivative described in <15> or <16>, in which one or two or more of $R^{21}$ to $R^{24}$ is a methyl group.

<19> A glycosaminoglycan derivative containing a group derived from glycosaminoglycan and a group derived from a physiologically active substance having at least one of a carboxy group and a hydroxy group which are coupled by covalent bond with a spacer therebetween, in which
the glycosaminoglycan is chondroitin sulfate,
the physiologically active substance is a nonsteroidal anti-inflammatory drug,
the group derived from a physiologically active substance and the spacer are covalently bonded through an ester bond,
the group derived from glycosaminoglycan and the spacer are covalently bonded through an amide bond, and
the spacer is a divalent group derived from amino alcohol represented by the following formula (II):

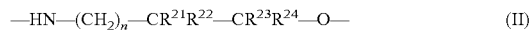

(in the formula, n is an integer of 0 to 12. $R^{21}$ to $R^{24}$ each independently represent a hydrogen atom or an electron withdrawing group).

<20> The glycosaminoglycan derivative described in <19>, in which the physiologically active substance is ketoprofen.

<21> The glycosaminoglycan derivative described in <19> or <20>, in which one or two or more of $R^{21}$ to $R^{24}$ is an electron withdrawing group.

<22> The glycosaminoglycan derivative described in <19> or <20>, in which one or two or more of $R^{21}$ to $R^{24}$ is fluorine.

<23> A pharmaceutical composition containing the glycosaminoglycan derivative described in any one of <15> to <22>.

<24> A pain suppressing agent containing the glycosaminoglycan derivative described in any one of <15> to <22>.

<25> The pain suppressing agent described in <24>, in which introduction ratio of a physiologically active substance in glycosaminoglycan derivative is 3% to 50%.

<26> The pain suppressing agent described in <24>, in which introduction ratio of a physiologically active substance in glycosaminoglycan derivative is 5% to 35%.

<27> The pain suppressing agent described in <24>, in which introduction ratio of a physiologically active substance in glycosaminoglycan derivative is 10% to 30%.

<28> The pain suppressing agent in solution form described in any one of <13> and <24> to <27>, in which content of the glycosaminoglycan derivative is 0.5% (w/v %) to 10% (w/v %) in the entire solution.

<29> The pain suppressing agent described in any one of <13> and <24> to <27>, in which content of the glycosaminoglycan derivative is 0.7% (w/v %) to 1.8% (w/v %) in the entire solution.

<30> The pain suppressing agent described in any one of <13> and <24> to <27>, in which content of the glycosaminoglycan derivative is 1% (w/v %) to 7% (w/v %) in the entire solution.

<31> The pain suppressing agent described in any one of <13> and <24> to <30>, in which it is administered with an administration interval of 3 days or more.

<32> The pain suppressing agent described in any one of <13> and <24> to <30>, in which it is administered with an administration interval of 7 days or more.

<33> The pain suppressing agent described in any one of <13> and <24> to <30>, in which it is administered with an administration interval of 10 days or more.

<34> The pain suppressing agent described in any one of <13> and <24> to <30>, in which it is administered with an administration interval of 14 days or more.

<35> The pain suppressing agent described in any one of <13> and <24> to <34>, in which the pain suppressing effect is maintained for 3 days or more after administration.

<36> The pain suppressing agent described in any one of <13> and <24> to <34>, in which the pain suppressing effect is maintained for 7 days or more after administration.

<37> The pain suppressing agent described in any one of <13> and <24> to <34>, in which the pain suppressing effect is maintained for 10 days or more after administration.

<38> The pain suppressing agent described in any one of <13> and <24> to <34>, in which the pain suppressing effect is maintained for 14 days or more after administration.

<39> The pain suppressing agent described in any one of <13> and <24> to <38>, in which it is a pain suppressing agent used for intramuscular injection.

<40> The pain suppressing agent described in any one of <13> and <24> to <39>, in which it is a pain suppressing agent used for treating muscle pain.

<41> The glycosaminoglycan derivative described in any one of <2> to <10> and <15> to <22>, in which dissociation rate of the physiologically active substance from the glycosaminoglycan derivative is 0.1 to 30%/day in a phosphate buffered saline with pH of 7.5 at 36° C.

<42> The pharmaceutical composition described in <11> or <23>, in which dissociation rate of the physiologically active substance from the glycosaminoglycan derivative is 0.1 to 30%/day in a phosphate buffered saline with pH of 7.5 at 36° C.

<43> The pain suppressing agent described in any one of <13> and <24> to <40>, in which dissociation rate of the physiologically active substance from the glycosaminoglycan derivative is 0.1 to 30%/day in a phosphate buffered saline with pH of 7.5 at 36° C.

Advantageous Effects of Invention

According to the present invention, the drug dissociation rate can be controlled without significantly depending on a structure of a drug, and thus a drug-introduced glycosaminoglycan derivative by which the introduced drug dissociates at an appropriate rate in accordance with a disorder for application, and a method for producing it can be provided.

DESCRIPTION OF EMBODIMENTS

Figure 1:
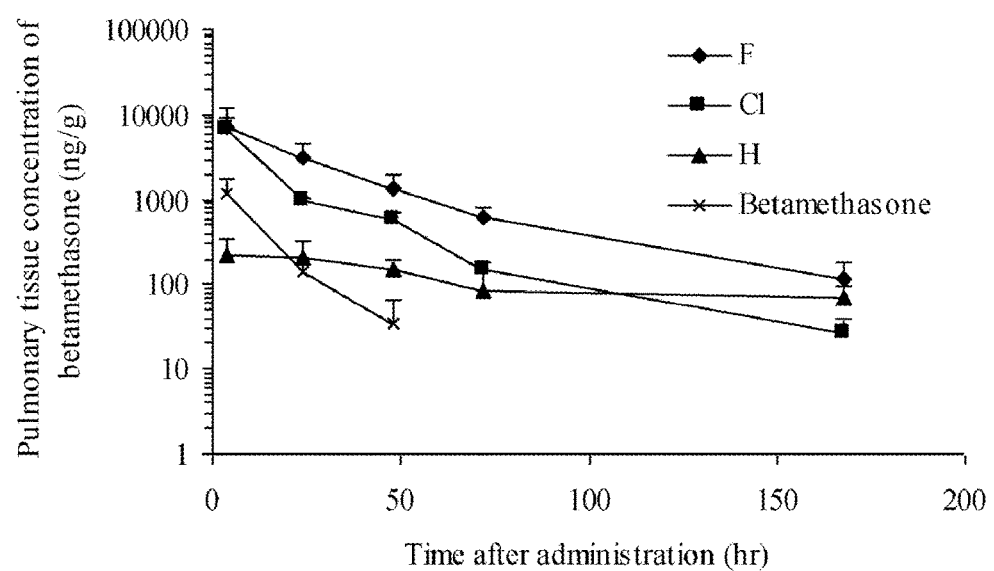
FIG. 1 is a graph illustrating the change of drug content in pulmonary tissue after administration of a GAG derivative.

As described herein, the term "step" encompasses not only an independent step but also a step which is not clearly distinguished from other steps but allows achievement of pre-determined purpose of the step. In addition, the numerical range described by using "to" indicates a range which has the numbers described before and after the "to" as a minimum value and a maximum value, respectively. Furthermore, when plural materials corresponding to each component are present in the composition, content of each component in the composition means the total amount of those plural materials in the composition, unless it is specifically described otherwise.

Hereinbelow, the present invention is explained in view of the embodiments of invention.

<Glycosaminoglycan Derivative>

The glycosaminoglycan derivative of this embodiment is a drug-introduced glycosaminoglycan derivative in which a group derived from glycosaminoglycan and a group derived from a physiologically active substance having at least one of a carboxy group and a hydroxy group (hereinbelow, also referred to as a "drug") are coupled by covalent bond with a spacer therebetween and the spacer is selected in accordance with the decomposition rate of the covalent bond between the group derived from the physiologically active substance and the spacer.

The glycosaminoglycan derivative of this embodiment allows having controlled drug release rate without significantly depending on a structure of a drug, and thus it allows drug release at rate that is appropriate for a disorder for application. Accordingly, it can be applied to any one of a disorder which requires early release of a drug and a disorder which requires sustained release of a drug for a long period of time. In addition, in terms of form of a pharmaceutical composition containing the glycosaminoglycan derivative, it can be applied as an injection solution, a powder preparation, or the like, and it can be used for control of various disorders like hyperlipidemia, arthritis, asthma, low back pain, pain, or the like.

Furthermore, according to this embodiment, the drug dissociation rate can be controlled at any temperature condition, and regarding a period for drug release, the drug dissociation rate can be controlled regardless of units like seconds, minutes, hours, days, months, or years.

The GAG derivative has a group derived from glycosaminoglycan (GAG), a group derived from a physiologically active substance, and a spacer which couples by covalent bond the group derived from glycosaminoglycan to group derived from a physiologically active substance. Regarding the GAG derivative, as the covalent bond between the spacer and the group derived from a physiologically active substance is dissociated (preferably, solvolyzed), the physiologically active substance is dissociated and released. The GAG derivative may further have other substituent groups, if necessary. Furthermore, when the GAG derivative has an acidic group like a carboxy group and a sulfuric acid group, it may be in a free acid state without forming a salt or in a state of a pharmaceutically acceptable salt.

As the pharmaceutically acceptable salt, there may be mentioned, for example, a salt with an alkali metal ion such as a sodium salt or a potassium salt, a salt with an alkaline earth metal ion such as a magnesium salt or a calcium salt. The GAG derivative is, from the viewpoint of applicability to a living body and affinity therefor, preferably a salt with a pharmaceutically acceptable alkali metal ion, and more preferably a sodium salt.

In a GAG derivative, coupling by a covalent bond of a group derived from GAG and a group derived from a physiologically active substance with a spacer therebetween means that the spacer is a group with valency of 2 or higher, and according to covalent bonding of each of a group derived from GAG and a group derived from a physiologically active substance to the spacer, a state in which the group derived from GAG and the group derived from a physiologically active substance are coupled to each other with a spacer therebetween is yielded.

In a GAG derivative, it is also possible that a group derived from GAG is covalently bonded with two or more groups derived from a physiologically active substance with one spacer therebetween. Number of the group derived from a physiologically active substance which is covalently bonded to one spacer is not particularly limited, if it is one or more. The spacer is not particularly limited either, if it is a divalent or higher valent group. It is preferably a divalent group.

The covalent bond between a group derived from a physiologically active substance and a spacer is, from the viewpoint of controlling the dissociation rate of a physiologically active substance from a GAG derivative, a covalent bond which can be decomposed in a living body, and it is preferably a covalent bond formed by condensation reaction, more preferably an ester bond or amide bond, and still more preferably an ester bond. As the covalent bond between a group derived from a physiologically active substance and a spacer in a GAG derivative is decomposed (preferably, solvolyzed), the physiologically active substance is dissociated. It is also possible that, after decomposition of a covalent bond between a group derived from GAG and a spacer, the covalent bond between a group derived from a physiologically active substance and a spacer is also decomposed to dissociate a physiologically active substance.

As described herein, the group derived from GAG means a group formed by removing at least one selected from a group consisting of a hydroxy group and a hydrogen atom from a GAG molecule. Furthermore, the group derived from a physiologically active substance is a group formed by removing at least one selected from a group consisting of a hydroxy group and a hydrogen atom from a physiologically active substance. Meanwhile, the site in a GAG molecule or a physiologically active substance from which a hydroxy group or a hydrogen atom is removed is not particularly limited. For example, when a hydroxy group is removed, it is preferable that a hydroxy group is removed from a carboxy group or a sulfuric acid group which may be found in a GAG molecule or a physiologically active substance. More preferably, a hydroxy group is removed from a carboxy group. Furthermore, when a hydrogen group is removed, for example, it is preferable that a hydrogen atom is removed from a hydroxy group or an amino group which may be found in a GAG molecule or a physiologically active substance.

The dissociation rate of a physiologically active substance can be measured by a method known per se. For example, it is possible that a GAG derivative is dissolved in a phosphate buffer solution having predetermined pH, a solution is sampled at a specific time interval (e.g., once a day) at predetermined temperature, and the dissociation rate is obtained from the dissociation ratio of a physiologically active substance in a sample solution, The GAG molecule constituting a GAG derivative is not particularly limited if the structural unit consisting of disaccharides, in which amino sugar and uronic acid or galactose are linked through a glycoside bond, has a repeating unit linked by glycoside bond.

Examples of the amino sugar constituting a GAG molecule include D-glucosamine and α-D-galactosamine. Examples of the uronic acid include β-D-glucuronic acid and α-L-iduronic acid.

The GAG molecule may have a structure in which a sulfuric acid group is added. The sulfuric acid group may be added to a hydroxy group or an amino group.

The GAG molecule may be used either singly or in combination of two or more types.

Examples of the GAG molecule include chondroitin sulfate (hereinbelow, also referred to as "CS"), hyaluronic acid (hereinbelow, also referred to as "HA"), heparin, heparan sulfate, keratan sulfate, dermatan sulfate, and a derivative thereof.

Among them, from the viewpoint of controlling the dissociation rate of a physiologically active substance from a GAG derivative, the GAG molecule is preferably a GAG molecule which has, in constructional unit, at least one reactive functional group selected from a group consisting of a carboxy group and a sulfuric acid group. It is more preferably at least one selected from a group consisting of chondroitin sulfate, hyaluronic acid, heparin, heparan sulfate, and a derivative thereof.

Molecular weight of the GAG molecule is not particularly limited, and it is suitably selected depending on the type of a monosaccharide molecule for constituting the GAG molecule, purpose, or the like. The weight average molecular weight of a GAG molecule can be 10,000 to 5,000,000 or 10 kDa to 5,000 kDa. It is preferably 15,000 to 2,000,000 or 15 kDa to 2,000 kDa, and more preferably 20,000 to 1,500,000 or 20 kDa to 1,500 kDa. The weight average molecular weight of a GAG molecule can be measured by a common method using size exclusion chromatography.

When hyaluronic acid is used as a GAG molecule, the weight average molecular weight of hyaluronic acid is not particularly limited, and it can be suitably selected depending on the purpose (e.g., disorder for application). The weight average molecular weight can be 10,000 to 5,000,000 or 10 kDa to 5,000 kDa. From the viewpoint of production efficiency, it is preferably 50,000 to 3,000,000 or 50 kDa to 3,000 kDa, and more preferably 200,000 to 1,500,000 or 200 kDa to 1,500 kDa. Furthermore, the molecular weight thereof may be selected in accordance with a disorder for application or the like When chondroitin sulfate is used as a GAG molecule, type of the chondroitin sulfate is not particularly limited, and any chondroitin sulfate like chondroitin sulfate A, chondroitin sulfate B, chondroitin sulfate C, chondroitin sulfate D, and chondroitin sulfate E can be used. Type of the chondroitin sulfate can be suitably selected depending on the purpose (e.g., disorder for application). The weight average molecular weight of the chondroitin sulfate is not particularly limited, and it can be selected depending on the purpose or the like. For example, the weight average molecular weight is preferably 10,000 to 100,000 or 10 kDa to 100 kDa, more preferably 10,000 to 60,000 or 10 kDa to 60 kDa, and even more preferably 10,000 to 40,000 or 10 kDa to 40 kDa.

The GAG derivative has at least one group derived from a physiologically active substance. The physiologically active substance is a compound which has at least one of a carboxy group and a hydroxy group. Accordingly, the dissociation rate from a GAG derivative can be easily controlled.

Type of the physiologically active substance for constituting a GAG derivative is not particularly limited, and it can be suitably selected depending on a purpose or the like. The physiological activity possessed by a physiologically active substance can be a physiological activity for treatment, prevention, or the like of a disorder, or a physiological activity for diagnosis or the like. Specific examples of the physiological activity include a steroidal activity, a nonsteroidal anti-inflammatory activity, an anti-rheumatoid activity, an anti-allergy activity, a β stimulation activity, a theophylline type activity, an anti-viral activity, an anti-choline activity, an anti-bacterial activity, an anti-hyperlipidemia activity, an expectorant activity, an anti-oxidant activity, an interferon type activity, and a local anesthetics activity.

Specific examples of the physiologically active substance include steroids, a nonsteroidal anti-inflammatory drug (NSAID), an anti-rheumatic drug (DMARD), an anti-allergic drug, a β stimulator, an anti-cholinergic drug, a bronchodilator, an anti-viral drug, an anti-bacterial drug, a therapeutic agent for hyperlipidemia, an expectorant, an anti-oxidant, an interferon agent, and local anesthetics. It is preferably at least one selected from a group consisting of steroids, a nonsteroidal anti-inflammatory drug, an anti-rheumatic drug, an anti-allergic drug, a β stimulator, and a therapeutic agent for hyperlipidemia.

Type of the steroids is not particularly limited, and it can be suitably selected depending on purpose or the like. Specific examples thereof include betamethasone, prednisolone, budesonide, and fluticasone. It is preferably at least one selected from a group consisting of them. Those steroids are suitably selected in consideration of disorders for application, activity strength of steroid itself, side effects, or the like.

Type of the nonsteroidal anti-inflammatory drug (NSAID) is not particularly limited, and it can be suitably selected depending on purpose or the like. Specific examples of the nonsteroidal anti-inflammatory drug (NSAID) include mefenamic acid, diclofenac, fenbufen, indometacin, felbinac, flurbiprofen, ketoprofen, and loxoprofen. It is preferably at least one selected from a group consisting of them.

Type of the bronchodilator is not particularly limited, and it can be suitably selected depending on purpose or the like.

Specific examples of the bronchodilator include a β stimulator, a theophylline drug (i.e., xanthine derivatives), and a parasympatholytic agent.

Specific examples of the β stimulator include tulobuterol. Furthermore, specific examples of the xanthine derivatives include proxyphylline. Examples of the parasympatholytic agent include an anti-cholinergic drug that is described below.

Type of the anti-allergic drug is not particularly limited, and it can be suitably selected depending on purpose or the like. Specific examples of the anti-allergic drug include a drug for suppressing dissociation of chemical delivery substance, a histamine antagonist, a thromboxane synthesis inhibitor, a thromboxane antagonist, a $TH_2$ cytokine inhibitor, and a leukotriene antagonist.

Specific examples of the thromboxane antagonist include seratrodast. Specific examples of the leukotriene antagonist include montelukast.

Type of the anti-cholinergic drug is not particularly limited, and it can be suitably selected depending on purpose or the like. Specific examples of the anti-cholinergic drug include ipratropium.

Type of the therapeutic agent for hyperlipidemia is not particularly limited, and it can be suitably selected depending on purpose or the like. Specific examples of the therapeutic agent for hyperlipidemia include bezafibrate.

The spacer in a GAG derivative is a divalent or higher valent group which couples by a covalent bond a group derived from GAG to a group derived from a physiologically active substance and it is selected depending on the decomposition rate of the covalent bond to a group derived from a physiologically active substance. From the viewpoint of controlling the dissociation rate of a physiologically active substance in a GAG derivative, it is preferable that at least one of a group derived from GAG and a spacer and a group derived from a physiologically active substance and a spacer is covalently bonded through an ester bond. More preferably, a group derived from a physiologically active substance and a spacer are covalently bonded through an ester bond. Even more preferably, a group derived from GAG and a spacer are covalently bonded through an amide bond and a group derived from a physiologically active substance and a spacer are covalently bonded through an ester bond.

Selecting a spacer depending on decomposition rate of a covalent bond to a group derived from a physiologically active substance includes selecting or employing the type of covalent bond between a spacer and a group derived from a physiologically active substance (e.g., ester bond, amide bond, carbonate bond, or urethane bond), selecting or employing the length of a spacer, selecting or employing the presence or absence of a substituent group on a carbon atom which directly or indirectly binds to the covalent bond between a spacer and a group derived from a physiologically active substance, and selecting or employing the type of a substituent group on a carbon atom which directly or indirectly binds to the covalent bond between a spacer and a group derived from a physiologically active substance (e.g., electron withdrawing group, electron donating group, and sterically hindered group).

The compound for forming a spacer (hereinbelow, it is also referred to as a spacer-forming molecule) preferably has, in the molecular structure, two or more reactive functional groups that are selected from a group consisting of a carboxy group, a hydroxy group and an amino group and a coupling group which couples those two or more reactive functional groups.

Herein, the two or more functional groups that are selected from a group consisting of a carboxy group, a hydroxy group and an amino group are suitably selected in accordance with a structure of a GAG molecule and a physiologically active substance. For example, when a carboxy group is contained as a reactive functional group of a GAG molecule, the spacer-forming molecule preferably has a hydroxy group or an amino group corresponding to the carboxy group of the GAG. More preferably, it has an amino group. When a hydroxy group is contained as a reactive functional group of a GAG molecule, the spacer-forming molecule preferably has a carboxy group corresponding to the hydroxyl group of the GAG.

Meanwhile, when a carboxy group is contained in a physiologically active substance, the spacer-forming molecule preferably has a hydroxy group or an amino group corresponding to the carboxy group of the physiologically active substance. More preferably, it has a hydroxy group. When a hydroxy group is contained in a physiologically active substance, the spacer-forming molecule preferably has a carboxy group corresponding to the hydroxyl group of the physiologically active substance.

From the viewpoint of controlling dissociation rate of a physiologically active substance from a GAG derivative, the spacer-forming molecule is preferably at least one selected from a group consisting of a compound having a carboxy group, an amino group, and a coupling group (preferably, an amino acid), a compound having a hydroxy group, an amino group, and a coupling group (preferably, an amino alcohol), a compound having two or more carboxy groups and a coupling group (preferably, dicarboxylic acid), a compound having a carboxy group, a hydroxy group, and a coupling group (preferably, hydroxy acid), and a compound having two or more hydroxy groups and a coupling group (preferably, diol compound). It is more preferably at least one selected from a group consisting of a compound having a carboxy group, an amino group, and a coupling group (preferably, an amino acid), a compound having a hydroxy group, an amino group, and a coupling group (preferably, an amino alcohol), and a compound having two or more carboxy groups and a coupling group (preferably, dicarboxylic acid).

Thus, from the viewpoint of controlling dissociation rate of a physiologically active substance from a GAG derivative, the GAG derivative is preferably a compound which is composed of a combination of constitutional molecules selected from a group consisting of a combination of "GAG molecule having a carboxy group, a physiologically active substance having a hydroxy group, and a spacer-forming molecule having an amino group and a carboxy group", a combination of "GAG molecule having a carboxy group, a physiologically active substance having a hydroxy group, and a spacer-forming molecule having a hydroxy group and a carboxy group", a combination of "GAG molecule having a carboxy group, a physiologically active substance having a carboxy group, and a spacer-forming molecule having an amino group and a hydroxy group", a combination of "GAG molecule having a carboxy group, a physiologically active substance having a carboxy group, and a spacer-forming molecule having two or more hydroxy groups", a combination of "GAG molecule having a hydroxy group, a physiologically active substance having a hydroxy group, and a spacer-forming molecule having two or more carboxy groups", and a combination of "GAG molecule having a hydroxy group, a physiologically active substance having a carboxy group, and a spacer-forming molecule having a carboxy group and a hydroxy group". It is more preferably a compound which is composed of a combination of constitutional molecules selected from a group consisting of a combination of "GAG molecule having a carboxy group, a physiologically active substance having a hydroxy group, and a spacer-forming molecule having an amino group and a carboxy group" and a combination of "GAG molecule having a carboxy group, a physiologically active substance having a carboxy group, and a spacer-forming molecule having an amino group and a hydroxy group".

The coupling group contained in a spacer-forming molecule is not particularly limited if it is a divalent or a higher valent group which can couple by a covalent bond two or more reactive functional groups. Examples of the coupling group include a divalent or a higher valent group derived from aliphatic hydrocarbons with 2 to 12 carbon atoms, a divalent or a higher valent group derived from aromatic hydrocarbons with 6 to 10 carbon atoms, and a combination thereof. The divalent or a higher valent group derived from aliphatic hydrocarbons means a hydrocarbon group which is formed by removing two or more hydrogen atoms from an aliphatic hydrocarbon molecule, and the site from which a hydrogen atom is removed is not particularly limited. The divalent or a higher valent group derived from aromatic hydrocarbons means an aromatic group which is formed by removing two or more hydrogen atoms from an aromatic hydrocarbon molecule, and the site from which a hydrogen atom is removed is not particularly limited.

From the viewpoint of suppressing immunogenicity, the length of the coupling group between reactive functional groups is preferably 12 or less atoms. It is more preferably 2 to 6 atoms.

The coupling group may have a substituent group. As the coupling group has a substituent group, the dissociation rate of a physiologically active substance in a GAG derivative can be more easily controlled to a desired range. Namely, without significantly depending on a structure of a physiologically active substance, the dissociation rate of a physiologically active substance from a GAG derivative can be more easily controlled.

Site for a substituent group in the coupling group can be any site at which stability of the covalent bond between a group derived from a physiologically active substance and a spacer (preferably, ester bond) is affected and it is preferably at least one site selected from a group consisting of a position and β position of a reactive functional group which binds to a group derived from a physiologically active substance. Number of the substituent group can be selected depending on the purpose, and it is preferably 1 to 4, and more preferably 1 to 2. When there are two substituent groups, for example, the substitution position can be α position and β position, or it may be α position only or β position only.

Type of the substituent group on a coupling group is, from the viewpoint of controlling dissociation rate of a physiologically active substance in a GAG derivative, preferably at least one selected from a group consisting of an electron withdrawing group, an electron donating group, and a sterically hindered group.

When a substituent group introduced to a coupling group is an electron withdrawing group, the covalent bond between a group derived from a physiologically active substance and a spacer decomposes more easily than a non-substitution case, and thus the dissociation rate of a physiologically active substance tends to increase. Thus, by selecting an electron withdrawing group based on electron withdrawing strength of an electron withdrawing group, for example, electronegativity, Hammett's constant, or the like as an indicator, it is possible to easily control the dissociation rate of a physiologically active substance to a desired range. Namely, there is a tendency that, by selecting a strong electron withdrawing group, the dissociation rate can be increased. Specifically, when a halogen atom like fluorine, chlorine, and bromine is introduced, the dissociation rate of a physiologically active substance tends to increase in the order of high electronegativity (F>Cl>Br).

The electron withdrawing group is not particularly limited as long as it can be introduced to a coupling group, and it can be suitably selected from generally used electron withdrawing groups. Specific examples of the electron withdrawing group include a halogen atom like fluorine, chlorine, and bromine, an alkyl and aryl sulfoxide group, an alkyl and aryl sulfone group, a sulfonic acid group, an acetamide group, a carboxy group, an alkyl and arylcarbonyloxy group (ester group), a fluoromethyl group, and a dimethylamino group. Among them, it is preferably at least one selected from a group consisting of a halogen atom and an alkylcarbonyloxy group.

When the substituent group which is introduced to a coupling group is an electron donating group, the covalent bond between a group derived from a physiologically active substance and a spacer decomposes less easily than a non-substitution case, and thus the dissociation rate of a physiologically active substance tends to decrease. The electron donating group can be selected by using a Hammett's constant as an indicator.

The electron donating group is not particularly limited as long as it can be introduced to a coupling group, and it can be suitably selected from generally used electron donating groups. Specific examples of the electron donating group include an alkene group and an alkyne group.

When the substituent group which is introduced to a coupling group is a sterically hindered group, the dissociation rate of a physiologically active substance tends to decrease. For a case in which the spacer-forming molecule is an amino acid, for example, the sterically hindered group can be selected by using the hydropathy index of an amino acid as an indicator.

Examples of the sterically hindered group include a linear alkyl group such as a methyl group, an ethyl group, a propyl group, or a butyl group, a branched alkyl group such as an isopropyl group, an isobutyl group, or a tert-butyl group, a cyclic alkyl group such as a cyclohexyl group, and an aryl group such as a phenyl group. Among them, a branched alkyl group, a cyclic alkyl group, and the like are preferable.

The substituent group on a coupling group may not be clearly classified into an electron withdrawing group, an electron donating group, or a sterically hindered group, but by selecting a substituent group using a Hammett's constant, hydropathy index, or the like as an indicator, the dissociation rate can be controlled.

Furthermore, it is also possible that the dissociation rate is finely controlled by introducing both the electron withdrawing group and the electron donating group. Still furthermore, it is also possible that the dissociation rate is finely controlled by introducing a substituent group having an electron withdrawing or electron donating property and steric hindrance.

Controlling the dissociation rate of a physiologically active substance includes increasing or decreasing the dissociation rate depending on a spacer structure. For example, regarding a method for controlling dissociation rate, when the dissociation rate is to be increased, a spacer having a substituent group of an electron withdrawing group needs to be selected. When the dissociation rate is to be decreased, a spacer having at least one substituent group selected from an electron donating group and a sterically hindered group needs to be selected. As for the spacer, it can be directly used, without introducing a substituent group, after being selected from a group consisting of an electron withdrawing group, an electron donating group, and a sterically hindered group.

Controlling the dissociation rate of a physiologically active substance by use of a spacer can be combined with selection of a coupling site to a spacer in a physiologically active substance. Specifically, when steroid is used as a physiologically active substance, for example, the ester bond generated by a hydroxy group at position 11 is hardly hydrolyzed due to steric hindrance, and thus it is believed that the steroid as a physiologically active substance introduced to a GAG derivative hardly dissociates. However, by suitably selecting a spacer which promotes hydrolysis of an ester bond from the aforementioned spacers, it becomes possible to dissociate the steroid from a GAG derivative. In addition, compared to a case in which an ester bond is generated by a hydroxy group at position 21, for example, the dissociation duration is extended so that the continuous working duration of the steroid can be extended.

Namely, by selecting a structure of a spacer, the range of a physiologically active substance applicable to a GAG derivative can be broadened.

The spacer-forming molecule is, although not particularly limited, preferably at least one selected from a group consisting of an amino acid, an amino alcohol, dicarboxylic acid, hydroxy acid, a diol compound, and a derivative thereof. It is more preferably at least one selected from a group consisting of an amino acid, an amino alcohol, dicarboxylic acid, and a derivative thereof. It is still more preferably at least one selected from a group consisting of an amino acid, an amino alcohol, and a derivative thereof.

For a case in which the physiologically active substance has a hydroxy group, the spacer-forming molecule is preferably at least one selected from a group consisting of an amino acid, dicarboxylic acid, hydroxy acid, and a derivative thereof. It is more preferably at least one selected from a group consisting of an amino acid, dicarboxylic acid, and a derivative thereof. It is still more preferably at least one selected from a group consisting of an amino acid and a derivative thereof.

For a case in which the physiologically active substance has a carboxy group, the spacer-forming molecule is preferably at least one selected from a group consisting of an amino alcohol, hydroxy acid, a diol compound, and a derivative thereof. It is more preferably at least one selected from a group consisting of an amino alcohol and a derivative thereof.

The amino acid as a spacer-forming molecule is not particularly limited if it is a compound having an amino group and a carboxy group. It may be either an amino acid of natural origin or a synthetic amino acid.

Specific examples of the amino acid include glycine, alanine, β-alanine, arginine, asparagine, serine, asparaginic acid, cysteine, glutamine, glutamic acid, proline, tyrosine, tryptophan, lysine, methionine, phenylalanine, threonine, valine, isoleucine, leucine, histidine, norvaline, norleucine, isoserine, ornithine, aminobutyric acid, aminovaleric acid, aminoheptanoic acid, aminooctanoic acid, aminodecanoic acid, aminoundecanoic acid, aminododecanoic acid, and a structural isomer thereof.

Among them, ω-aminofatty acid like glycine, β-alanine, aminobutyric acid, aminovaleric acid, aminoheptanoic acid, aminooctanoic acid, aminodecanoic acid, aminoundecanoic acid, and aminododecanoic acid can be preferably used. Meanwhile, those ω-aminofatty acids may have a substituent group, and it is preferable to have a substituent group on α position or β position of a carboxy group. Number of the carbon atom in ω-aminofatty acid is not particularly limited, but from the viewpoint of controlling the dissociation rate, it is preferably 3 or more, more preferably 3 to 12, and still more preferably 3 to 6. Meanwhile, the number of carbon atoms in ω-aminofatty acid indicates the total carbon number including the carbonyl carbon of a carboxy group.

Examples of the amino acid derivative include a halogenated derivative in which the hydrogen atom of the carbon at α position, which is adjacent to the carboxy group, is substituted with a halogen, e.g., 2-fluoro-3-amino-propanoic acid, 2-chloro-3-amino-propanoic acid, and 2-bromo-3-amino-propanoic acid, an alkyl substituted derivative in which the hydrogen atom of the carbon at α position, which is adjacent to the carboxy group, is substituted with an alkyl chain, e.g., 2-methyl-2-aminopropanoic acid, and diethylglycine, and an amino acid with an ether bond like 11-amino-3,6,9-trioxaundecanoic acid.

As for the amino acid derivative, a derivative selected from the aforementioned amino acids, or a dipeptide, a tripeptide, or a tetrapeptide resulting from a combination thereof can be also used.

Specific examples of the amino alcohol include aliphatic amino alcohol such as aminoethanol, aminopropanol, aminobutanol, or aminohexanol; and aminoarylalkylalcohol such as aminophenylethanol or aminobenzylalcohol; and a structural isomer thereof.

Examples of the amino alcohol derivative include halogenated amino alcohol in which the hydrogen atom of the carbon at α position or the carbon at β position, which is adjacent to the first position or second position when counted from the hydroxy group, such as 3-amino-2-fluoro-1-propanol or 4-amino-3-fluoro-1-butanol.

Specific examples of the dicarboxylic acid include aliphatic dicarboxylic acid such as oxalic acid, malonic acid, succinic acid, glutaric acid, adipic acid, pimellic acid, suberic acid, azellaic acid, or sebacic acid; aromatic dicarboxylic acid such as phthalic acid, isophthalic acid, or terephthalic acid; and a structural isomer thereof.

Examples of the dicarboxylic acid derivative include tartronic acid, tartaric acid, isocitric acid, citric acid, citramalic acid, and malic acid.

Examples of the hydroxy acid include glycolic acid, lactic acid, 2-hydroxybutyric acid, 3-hydroxybutyric acid, γ-hydroxybutyric acid, 2-phosphoglyserine acid, 3-phosphoglyserine acid, leucine acid, ricinoleic acid, cereblonic acid, and a structural isomer thereof.

Examples of the hydroxy acid derivative include malic acid, glycerin acid, tartronic acid, tartaric acid, pantoic acid, and mevalonic acid.

The spacer in a GAG derivative is, from the viewpoint of controlling the dissociation rate of a physiologically active substance from a GAG derivative, preferably a divalent or higher valent group derived from at least one selected from a group consisting of an amino acid, an amino alcohol, dicarboxylic acid, and a derivative thereof. It is more preferably a divalent or higher valent group derived from at least one selected from a group consisting of an amino acid, an amino alcohol, and a derivative thereof.

When the spacer in a GAG derivative is a divalent group derived from an amino acid or a derivative thereof, the spacer is preferably a divalent group derived from an amino acid that is represented by the following formula (I). The spacer represented by the formula (I) can be preferably applied for a case in which the physiologically active substance has a hydroxy group.

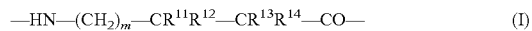

$$-HN-(CH_2)_m-CR^{11}R^{12}-CR^{13}R^{14}-CO- \quad (I)$$

In the formula, m is an integer of 0 to 12. $R^{11}$, $R^{12}$, $R^{13}$, and $R^{14}$ each independently represent a hydrogen atom, an electron withdrawing group, an electron donating group, or a sterically hindered group. m is preferably 0 to 8, and more preferably 0 to 4. Furthermore, $R^{11}$, $R^{12}$, $R^{13}$, and $R^{14}$ groups may be the same or different from each other, either completely or partially.

Details of the electron withdrawing group, electron donating group, and sterically hindered group are as defined above. By suitably selecting $R^{11}$, $R^{12}$, $R^{13}$, and $R^{14}$ in the spacer represented by the formula (I), the dissociation rate of a physiologically active substance from a GAG derivative can be controlled. Thus, at least one of $R^{11}$ to $R^{14}$ is preferably an electron withdrawing group, an electron donating group, or a sterically hindered group.

For example, when at least one of $R^{11}$ to $R^{14}$ is an electron withdrawing group like a halogen atom, the coupling strength is lowered so that the physiologically active substance is more easily dissociated and the dissociation rate is increased.

In terms of the influence of an ester bond on the dissociation rate, a higher effect can be obtained when an electron withdrawing group is introduced to $R^{13}$ or $R^{14}$ instead of $R^{11}$ and $R^{12}$. Furthermore, by selecting an electron withdrawing group in accordance with the strength of an electron withdrawing property, e.g., electronegativity, it becomes possible to control the dissociation rate of a physiologically active substance. Namely, there is a tendency that the dissociation rate increases by introducing a substituent group with higher electronegativity.

The electron withdrawing group introduced to $R^{11}$ to $R^{14}$ can be any kind of an electron withdrawing group as long as it can be introduced, and examples thereof include a halogen atom, an alkyl and aryl sulfoxide group, an alkyl and aryl sulfone group, a sulfonic acid group, an acetamide group, a carboxy group, and an alkyloxy carbonyl group.

For example, when a halogen atom like fluorine, chlorine, and bromine is introduced to $R^{13}$ or $R^{14}$, the dissociation rate of a physiologically active substance tends to increase in the order of high electronegativity (F>Cl>Br) due to the reason described above.

On the contrary, when an electron donating group is introduced to $R^{13}$ or $R^{14}$, it is possible to lower the dissociation rate of a physiologically active substance. The electron donating group for $R^{13}$ or $R^{14}$ is not particularly limited as long as it has a structure capable of supplying an electron.

In order to further lower the dissociation rate of a physiologically active substance, it is possible to cause steric hindrance by introducing to a spacer a linear alkyl group such as a methyl group, an ethyl group, a propyl group, or a butyl group, a branched alkyl group such as an isopropyl group, an isobutyl group, or a tert-butyl group, a cyclic alkyl group such as a cyclohexyl group, and an aryl group such as a phenyl group, and thus lowering the dissociation rate.

It is also possible that, by having each of $R^{11}$ (or $R^{12}$), and $R^{13}$ (or $R^{14}$) as an electron withdrawing group and an electron donating group, respectively, the dissociation rate is finely controlled. Furthermore, by having a substituent group having an electron withdrawing property or an electron donating property with steric hindrance as $R^{11}$ to $R^{14}$, the dissociation rate can be finely controlled.

Specific examples of the spacer represented by the formula (I) include spacers described in the following Table 1, but this embodiment is not limited to them. Meanwhile, in the following Table 1, H represents a hydrogen atom, F represents a fluorine atom, Cl represents a chlorine atom, Br represents a bromine atom, OH represents a hydroxy group, and OTs represents a toluenesulfonyloxy group.

TABLE 1

|  | m | $R^{11}$ | $R^{12}$ | $R^{13}$ | $R^{14}$ |
|---|---|---|---|---|---|
| I-1 | 0 | H | H | H | H |
| I-2 | 0 | H | H | F | H |
| I-3 | 0 | H | H | Cl | H |
| I-4 | 0 | H | H | Br | H |
| I-5 | 0 | H | H | OH | H |
| I-6 | 0 | H | H | OTs | H |

When the spacer in a GAG derivative is a divalent group derived from an amino alcohol or a derivative thereof, the spacer is preferably a divalent group derived from an amino alcohol that is represented by the following formula (II). The spacer represented by the formula (II) can be preferably applied for a case in which the physiologically active substance has a carboxy group.

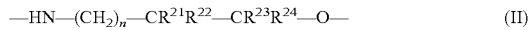  (II)

In the formula, n is an integer of 0 to 12. $R^{21}$, $R^{22}$, $R^{23}$, and $R^{24}$ each independently represent a hydrogen atom, an electron withdrawing group, an electron donating group, or a sterically hindered group. n is preferably 0 to 8, and even more preferably 0 to 4. Furthermore, $R^{21}$, $R^{22}$, $R^{23}$, and $R^{24}$ groups may be the same or different from each other, either completely or partially.

Details of the electron withdrawing group, electron donating group, and sterically hindered group are as defined above. By suitably selecting $R^{21}$, $R^{22}$, $R^{23}$, and $R^{24}$ in the spacer represented by the formula (II), the dissociation rate of a physiologically active substance from a GAG derivative can be controlled. At least one of $R^{21}$ to $R^{24}$ is preferably an electron withdrawing group, an electron donating group, or a sterically hindered group.

For example, when a spacer in which at least one of $R^{21}$ and $R^{22}$ is an electron withdrawing group like halogen atom is used, the dissociation rate of a physiologically active substance is increased. The electron withdrawing group introduced to $R^{21}$ or $R^{22}$ can be any kind of an electron withdrawing group as long as it can be introduced, and examples thereof include a halogen atom, an alkyl and aryl sulfoxide group, an alkyl and aryl sulfone group, a sulfonic acid group, an acetamide group, a carboxy group, and an alkyloxy carbonyl group.

For example, a physiologically active substance in a derivative in which $R^{21}$ is a halogen atom with high electronegativity and $R^{22}$ is a hydrogen atom has a high dissociation rate. Furthermore, by having a halogen atom for both of $R^{21}$ and $R^{22}$, the dissociation rate further increases. Furthermore, when $R^{23}$ or $R^{24}$ closer to an ester bond is an electron withdrawing group, it is also possible to further accelerate drug release.

On the contrary, when $R^{21}$ or $R^{22}$ is an electron donating group, the dissociation rate of a physiologically active substance can be further reduced. The electron donating group as $R^{21}$ or $R^{22}$ is not particularly limited as long as it has a structure capable of supplying an electron.

When an alkyl group or the like is introduced to $R^{23}$ or $R^{24}$ and the hydroxy group of a spacer-forming molecule is a secondary or tertiary hydroxy group, the dissociation rate is reduced. It is also possible to reduce the dissociation rate by causing steric hindrance according to introduction of a linear alkyl group such as a methyl group, an ethyl group, a propyl group, or a butyl group, a branched alkyl group such as an isopropyl group, an isobutyl group, or a tert-butyl group, a cyclic alkyl group such as a cyclohexyl group, and an aryl group such as a phenyl group to $R^{23}$ or $R^{24}$.

By having two selected from $R^{21}$ to $R^{24}$ as an electron withdrawing group and an electron donating group, respectively, the dissociation rate can be finely controlled. In addition, by having $R^{21}$ to $R^{24}$ as a substituent group which has an electron withdrawing property or an electron donating property with steric hindrance, the dissociation rate can be also finely controlled.

Specific examples of the spacer represented by the formula (II) include spacers described in the following Table 2, but this embodiment is not limited to them. Meanwhile, in the following Table 2, H represents a hydrogen atom, F represents a fluorine atom, Cl represents a chlorine atom, Br represents a bromine atom, Me represents a methyl group, and COOEt represents an ethoxycarbonyl group.

TABLE 2

|  | n | $R^{21}$ | $R^{22}$ | $R^{23}$ | $R^{24}$ |
|---|---|---|---|---|---|
| II-1 | 1 | H | H | H | H |
| II-2 | 1 | F | H | H | H |
| II-3 | 1 | F | F | H | H |
| II-4 | 1 | Cl | H | H | H |
| II-5 | 0 | COOEt | H | H | H |
| II-6 | 0 | H | H | Me | H |
| II-7 | 0 | COOEt | H | Me | H |

The spacer in a GAG derivative is, from the viewpoint of controlling the dissolution rate of a physiologically active substance, a divalent or higher valent group derived from at least one amino acid selected from a group consisting of glycine, alanine, leucine, isoleucine, valine, serine, threonine, asparaginic acid, glutamic acid, asparagine, glutamine, arginine, lysine, histidine, tryptophan, phenylalanine, tyrosine, methionine, cysteine, proline, ornithine, β-alanine, and a derivative thereof, and preferably a divalent or higher valent group derived from at least one amino alcohol selected from a group consisting of aminopropanol, aminoethanol, and a derivative thereof.

The ratio between a content number of constructional unit composed of disaccharide which constitutes a group derived from GAG and a content number of a group derived from a physiologically active substance in a GAG derivative is not particularly limited. The ratio can be represented by the mole number ratio of a group derived from a physiologically active substance relative to total mole number of carboxy group in the GAG (hereinbelow, it may be expressed as introduction ratio). The introduction ratio is, although not particularly limited, 1% to 100%, for example.

Meanwhile, the content ratio of a physiologically active substance can be suitably selected depending on use, type, and activity strength, a property of a physiologically active substance like solubility in water, and type of a spacer, or the like. For example, it is preferably prepared such that the content of a physiologically active substance is 1 μg to 100 mg per single administration.

The GAG derivative may be composed of a combination of a single type of GAG molecule and a single type of physiologically active substance, a combination of a single type of GAG molecule and two or more types of physiologically active substance, or a combination of two or more types of GAG molecule and a single type of physiologically active substance.

The duration during which dissociation rate of a physiologically active substance is controlled by GAG derivative is not particularly limited, and it can be unit like seconds, minutes, hours, months, or years. Preferably, it is controlled for 1 week or longer. More preferably, it is controlled for 2 weeks or longer. Still more preferably, it is controlled for 1 month or longer. Even sill more preferably, it is controlled for 6 months or longer. Particularly preferably, it is controlled for 1 year or longer.

The dissociation rate of a physiologically active substance from a GAG derivative is not particularly limited, and it can be suitably selected depending on the purpose or the like. For example, the dissociation rate of a physiologically active substance from a GAG derivative can be, in a phosphate buffered saline at pH 7.5, 36° C., 0.1 to 30%/day, 0.2 to 20%/day, 0.3 to 10%/day, 0.3 to 5%/day, 0.3% to 4%/day, 0.3 to 3%/day, 0.3 to 2%/day, 0.3 to 1%/day, 0.5 to 5%/day, 0.5 to 4%/day, 0.5 to 3%/day, 0.5 to 2%/day, 0.5 to 1%/day, 0.6 to 5%/day, 0.6 to 4%/day, 0.6 to 3%/day, 0.6 to 2%/day, or 0.6 to 1%/day. Herein, the dissociation rate of a physiologically active substance, which corresponds to a variation amount of dissociation ratio (%) per day, is defined by slope of a graph in which time is plotted on a horizontal axis and the dissociation ratio (%), which is a ratio of the dissociation amount (mole) of a physiologically active substance relative to total mole number (100%) of a group derived from a physiologically active substance contained in the GAG derivative, is plotted on a vertical axis. Thus, when the dissociation rate maintains a constant value during the measurement period, the graph shows a monotonically increasing straight line, and for a case in which all the physiologically active substances contained in a polysaccharide derivative are dissociated within 10 days in a 10 mM phosphate buffered saline at pH 7.5, 36° C., the dissociation rate is expressed as 10%/day. Meanwhile, when the dissociation rate shows a decrease over the time instead of having a constant value (i.e., graph shows a mild curve having a bulge in the upward direction and monotonic increase), the change in dissociation ratio during initial increase period (e.g., for 3 days) is approximated to a straight line to calculate the dissociation rate.

Meanwhile, the dissociation amount of a physiologically active substance can be measured by a method which is suitably selected depending on the type of a physiologically active substance.

The constitution and technical spirit of the GAG derivative of this embodiment can be applied to a polysaccharide other than GAG. Examples of the polysaccharide other than GAG include carboxymethyl cellulose, carboxymethylethyl cellulose, chitosan, chitin, cellulose, and a derivative thereof.

<Method for Producing Glycosaminoglycan Derivative>

The method for producing a glycosaminoglycan derivative of this embodiment is a production method which includes:

(1) preparing a physiologically active substance having a carboxy group or a hydroxy group, (2) selecting a spacer for forming a covalent bond with a group derived from a physiologically active substance in accordance with decomposition rate of the covalent bond, and (3) forming a covalent bond between the group derived from a physiologically active substance and a group derived from glycosaminoglycan with the spacer therebetween.

As the spacer constituting the GAG derivative is selected in accordance with decomposition rate of the covalent bond to a group derived from a physiologically active substance, it becomes possible to control the dissociation rate without significantly depending on the structure of a physiologically active substance.

Regarding the step (1), a substance having desired physiological activity can be prepared by selecting suitably from a known physiologically active substance, or it can be prepared by producing a desired physiologically active substance according to a known method.

Regarding the step (2), a spacer-forming molecule is preferably selected such that the dissociation rate of a physiologically active substance is within a desired range. The spacer-forming molecule has a hydroxy group or carboxy group as a reactive functional group for forming an ester bond with a physiologically active substance, a reactive functional group (preferably, amino group) for forming a covalent bond (preferably amide bond) with GAG, and a coupling group which is selected such that it can couple the two reactive functional groups and control the dissociation rate of an ester bond to a physiologically active substance. For example, by suitably selecting a substituent group present in a spacer-forming molecule, desired decomposition rate can be achieved. Details of a method for selecting the spacer-forming molecules are as described above.

Regarding the step (3), a GAG derivative is produced by using a prepared physiologically active substance, a selected spacer-forming molecule, and GAG. The step (3) may include the following steps, for example.

A production method including (3a) forming an ester bond between a carboxy group or a hydroxy group in a physiologically active substance and a reactive functional group in a spacer-forming molecule, and (3b) forming a covalent bond according to condensation of a carboxy group in a GAG molecule with a reactive functional group in a spacer-forming molecule.

According to the step (3a), an ester bond is formed, by a commonly used esterification method, between a carboxy group or a hydroxy group in a physiologically active substance and a reactive functional group in a spacer-forming molecule (preferably, hydroxy group or carboxy group). In that case, the reactive functional group which is supposed to bind to a GAG molecule of a spacer-forming molecule may be protected in advance according to a commonly used method, if necessary.

Examples of the esterification method include a method of using a condensation agent such as water soluble carbodiimide (e.g., 1-ethyl-3-(3-dimethylaminopropyl)carbodiimide) or dicyclohexyl carbodiimide, a symmetric acid anhydride method, a mixed acid anhydride method, and an active esterification method. The reaction conditions for the esterification method can be suitably selected depending on an esterification method for application.

During the step (3b), a covalent bond is formed according to condensation of a carboxy group in a GAG molecule with a reactive functional group (preferably, amino group) in a spacer-forming molecule. The condensation method can be suitably selected from a commonly used method depending on a convent bond to be formed. In that case, the reactive functional group which is supposed to bind to a physiologically active substance of a spacer-forming molecule may be protected in advance according to a commonly used method, if necessary.

Order of the step (3a) and the step (3b) is not particularly limited. From the viewpoint of production efficiency, it is preferable to perform the step (3b) after the step (3a).

The method for producing a GAG derivative may further include a step for preparing glycosaminoglycan before the step (3). Glycosaminoglycan is not particularly limited, and it can be selected from known glycosaminoglycans depending on the purpose of using GAG derivative, or it may be newly produced depending on the purpose.

The constitution and technical spirit of this embodiment can be applied to a polysaccharide other than GAG. Examples of the polysaccharide other than GAG include carboxymethyl cellulose, carboxymethylethyl cellulose, chitosan, chitin, cellulose, and a derivative thereof.

<Method for Controlling Dissociation Rate of Physiologically Active Substance from Glycosaminoglycan Derivative>

The method for controlling dissociation rate of a physiologically active substance from a glycosaminoglycan derivative of this embodiment is characterized in that it includes selecting a spacer included in a glycosaminoglycan derivative, in which a group derived from glycosaminoglycan and a group derived from a physiologically active substance having at least one of a carboxy group and a hydroxy group are coupled by covalent bond with a spacer therebetween, in accordance with decomposition rate of the covalent bond between the group derived from a physiologically active substance and the spacer.

As the spacer for constituting a GAG derivative is selected in accordance with decomposition rate of the covalent bond to the group derived from a physiologically active substance, it becomes possible to control the dissociation rate without significantly depending on a structure of a physiologically active substance.

Details of the GAG derivative are as defined above. Furthermore, selecting a spacer in accordance with decomposition rate of the covalent bond to the group derived from a physiologically active substance preferably includes selecting a substituent group which is contained in a spacer-forming molecule for forming a spacer. Accordingly, the dissociation rate of a physiologically active substance can be more easily controlled to a desired range. Meanwhile, the details of the method for selecting a spacer-forming molecule are as described above.

Temperature conditions for controlling the dissociation rate are not particularly limited, and they can be suitably selected depending on a storage container, a target tissue, or the like. Specific temperature may be 0° C. to 90° C., and it may be more specifically 2° C. to 80° C., 4° C. to 70° C., or 25° C. to 60° C.

The duration during which dissociation rate can be controlled is not particularly limited, and it can be unit like seconds, minutes, hours, months, or years. Preferably, it is controlled for 1 week or longer. More preferably, it is controlled for 2 weeks or longer. Still more preferably, it is controlled for 1 month or longer. Even sill more preferably, it is controlled for 6 months or longer. Particularly preferably, it is controlled for 1 year or longer.

The constitution and technical spirit of the method for controlling dissociation rate of a physiologically active substance can be applied to a polysaccharide other than GAG. Examples of the polysaccharide other than GAG include carboxymethyl cellulose, carboxymethylethyl cellulose, chitosan, chitin, cellulose, and a derivative thereof.

<Pharmaceutical Composition>

The pharmaceutical composition of this embodiment contains at least one glycosaminoglycan derivative described above. The pharmaceutical composition may contain only one type of a GAG derivative or two or more of them in combination. When two or more kinds of GAG derivatives are contained, it can be a combination of two or more kinds of GAG derivatives in which two or more different kinds of GAG are combined with one physiologically active substance or a combination of two or more kinds of GAG derivatives in which two or more kinds of different physiologically active substances are combined with one GAG.

Content of the GAG derivative in a pharmaceutical composition is not particularly limited, and it can be suitably selected depending on the purpose of the like.

The pharmaceutical composition may contain, in addition to a GAG derivative, other components including pharmaceutically acceptable vehicle or the like. Examples of other components include a surface active agent, a physiologically active substance, a stabilizer, an isotonic agent, a liquid medium and a buffer agent as well as a pharmaceutically acceptable vehicle or the like. The physiologically active substance may be the same or different from a physiologically active substance which is dissociated from a GAG derivative.

The disorder as a subject for the pharmaceutical composition of the present invention is not particularly limited. By suitably selecting a group derived from a physiologically active substance contained in GAG derivative, it can be applied to various disorders. Furthermore, as the dissociation rate of a physiologically active substance from a GAG derivative can be controlled, drug dissociation rate which is stable before administration to a living body and is suitable for application in a living body after administration can be achieved. Furthermore, as a drug is covalently bonded to a GAG via a spacer, the GAG derivative is expected to have a long-acting effect. In general, a long-acting effect is expected to have different acting time depending on disorder. Furthermore, in an actual case of a chronic disorder or the like, frequent administration is necessary to have a long-acting effect, and thus side effects or inconveniences or the like are caused by it. Furthermore, as lowered adherence may be also caused, there can be a case in which it is required to have lower administration frequency, i.e., to have a long-acting effect.

By using a drug with desired physiological activity, the pharmaceutical composition of this embodiment contains a GAG derivative with dissociation rate controlled to have desired rate. Thus, it can be applied to various chronic disorders so that it can contribute to improvement of adherence.

By containing a GAG derivative, the pharmaceutical composition can gradually dissociate a physiologically active substance in a target tissue. Namely, the GAG derivative may constitute a controlled release preparation containing it.

The duration during which dissociation rate of a physiologically active substance in a pharmaceutical composition can be controlled is not particularly limited, and it can be unit like seconds, minutes, hours, months, or years. Preferably, it is controlled for 1 week or longer. More preferably, it is controlled for 2 weeks or longer. Still more preferably, it is controlled for 1 month or longer. Even sill more preferably, it is controlled for 6 months or longer. Particularly preferably, it is controlled for 1 year or longer.

The constitution and technical spirit of the pharmaceutical composition of this embodiment can be applied to a polysaccharide other than GAG. Examples of the polysaccharide other than GAG include carboxymethyl cellulose, carboxymethylethyl cellulose, chitosan, chitin, cellulose, and a derivative thereof.

The long-acting effect of the pharmaceutical composition in a target tissue can be evaluated in accordance with a target tissue.

For example, when the target tissue is a lung, pH of an alveolar layer is generally known to be weakly alkaline (i.e., pH of 7.5 or so). Thus, when a pharmaceutical composition as a subject for evaluation is dissolved in 10 mM phosphate buffer solution prepared to have pH of about 7.5 and stored for 1 week at 36° C., the long-acting effect can be evaluated based on the dissociation ratio of a physiologically active substance.

Furthermore, when the target tissue is a nasal cavity, pH of nasal cavity mucosa from a patient suffering from allergic sinusitis is generally known to be weakly alkaline (i.e., pH of 8.0 or so). Thus, when a pharmaceutical composition as a subject for evaluation is dissolved in 10 mM phosphate buffer solution prepared to have pH of about 8.0 and stored for 1 week at 36° C., the long-acting effect can be evaluated based on the dissociation ratio of a physiologically active substance.

The pharmaceutical composition is used for administration to a respiratory organ. Namely, the pharmaceutical composition is preferably used in the form of intrapulmonary administration, intranasal administration, or the like.

In that case, the pharmaceutical composition may be in the form administrable to a respiratory organ, and it may be any form like powder, liquid, and suspension.

Examples of administration methods include an administration method using inhalation by a user himself, air stream created by an external device, or a method of using both of them, and an administration method using a nebulizer.

The pharmaceutical composition administered to a respiratory organ is arrived at and adhered to a target tissue of a respiratory organ while a physiologically active substance and a GAG are still covalently bonded via a spacer. After that, as the covalent bond between the spacer and the physiologically active substance is gradually decomposed, sustained release of a physiologically active substance for a long period of time (e.g., 24 hours or longer) is achieved.

Examples of the target tissue to which administration to a respiratory organ can be applied include a pulmonary tissue (alveolus, terminal bronchiole, bronchiole, and bronchus), nasal cavity (paranasal cavity, frontal sinus, ethmoid sinus, maxillary sinus, sphenoidal sinus, superior turbinate, middle turbinate, and inferior turbinate).

The pharmaceutical composition can be suitably applied to therapeutics of a respiratory disorder, for example, but the use of the pharmaceutical composition is not limited to therapeutics of a respiratory disorder. It can be applied for, in addition to prevention of a respiratory disorder, treatment, prevention, diagnosis, or the like of other disorders, depending on the type of a physiologically active substance.

When the pharmaceutical composition is used for therapeutics or prophylaxis of a respiratory disorder, examples of the respiratory disorder include bronchial asthma, chronic obstructive pulmonary disorder (COPD), viral infection, acute allergic disorder, and chronic allergic disorder.

The pharmaceutical composition can be preferably applied to bronchial asthma.

Bronchial asthma (or asthma) is a disorder in which an airway hyper-responsiveness is enhanced due to an allergic reaction or the like to cause obstructed airway, yielding difficult breathing. Currently, as a main treatment of asthma, combination of long-term management drug using steroids for inhaling and bronchial dilating drug prescribed for seizure is mainly employed. As described above, asthma is also defined as chronic inflammation of an airway, and thus an airway inflammation is shown from an asthma patient even before exhibiting any seizure. For such reasons, when steroids having a strong anti-inflammatory activity as a working mechanism are continuously inhaled as a long-term management drug even before an occurrence of a seizure, chronic inflammation of an airway is suppressed so that symptoms of asthma can be greatly improved.

Meanwhile, the acting time of anti-inflammatory activity of inhaling steroids is short so that 1 to 8 inhalations are needed per day. Thus, it is very inconvenient for a patient who takes everyday a long-term management drug, and it may cause a decrease in adherence.

Accordingly, when a steroid introduced GAG derivative in which steroid is chemically introduced to a GAG is used as a long-term management drug, a long-term anti-inflammatory effect can be continued for several days only by single inhalation. Thus, several inhalations per day are not necessary so that the inconvenience problem is solved and also it is expected to have an increase in adherence of a patient.

In that case, by modifying a structure of a spacer in the GAG derivative, it is also possible to extend or shorten the administration interval, i.e., time of having the sustained anti-inflammatory effect. It is also possible to control the strength of the anti-inflammatory effect according to steroid to be selected.

Specific examples of other application of the pharmaceutical composition include, other than asthma, application as a treatment agent for arthritis, an application to muscle disorder, an application as a treatment agent for low back pain, an application to myofascial pain syndrome, and an application to muscle pain.

Examples of the administration method include an intraarticular administration and an intramuscular administration.

For example, a nonsteroidal anti-inflammatory drug (NSAID) introduced GAG derivative in which a NSAID is introduced as a physiologically active substance to a GAG with controllable dissociation rate of a physiologically active substance is expected to exhibit a long-term pain suppressing and anti-inflammatory effect against arthritis, low back pain, or the like.

Namely, as the above glycosaminoglycan derivative has NSAIDs introduced thereto as a physiologically active substance, it can constitute a pain suppressing agent or a long-acting pain suppressing agent containing it.

Content of the GAG derivative in the pain suppressing agent of this embodiment is, although not particularly limited, preferably 0.5% (w/v %) to 10% (w/v %), more preferably 0.7% (w/v %) to 8% (w/v %), even more preferably 1% (w/v %) to 5% (w/v %), and still even more preferably 1% (w/v %) or 5% (w/v %) in the entire solution.

When hyaluronic acid is used as a GAG molecule, content of the GAG derivative in a pain suppressing agent of this embodiment is, although not particularly limited, preferably 0.5% (w/v %) to 3% (w/v %), more preferably 0.7% (w/v %) to 1.8% (w/v %), and even more preferably 1% (w/v %) in the entire solution.

When chondroitin sulfate is used as a GAG molecule, content of the GAG derivative in a pain suppressing agent of this embodiment is, although not particularly limited, preferably 0.5% (w/v %) to 10% (w/v %), more preferably 1% (w/v %) to 7% (w/v %), and even more preferably 1% (w/v %) or 5% (w/v %) in the entire solution.

Examples of the NSAIDs which can be introduced to a GAG derivative include a compound having at least one of a carboxy group and a hydroxy group, i.e., mefenamic acid, diclofenac, fenbufen, indometacin, felbinac, flurbiprofen, ketoprofen, and loxoprofen.

When coupling to GAG is achieved by utilizing the carboxy group of NSAIDs, an amino alcohol and a derivative thereof are used as a spacer, and a covalent bond is formed by an amide bond or ester bond for GAG and NSAIDs, respectively. By selecting the spacer constitution described above, the dissociation rate of NSAIDs can be controlled.

The GAG derivative introduced with NSAIDs can be also used as local intramuscular sustained-release analgesics for muscular pain like chronic low back pain or myofascial pain syndrome.

Among chronic pains, chronic low back pain is most frequently observed and it can be classified into specific low back pain with mixed inflammatory pain and neuropathic pain and identifiable focal area and non-specific low back pain with non-identifiable focal area of pain in which pain is sometimes strongly related to socio-psychological factors. Depending on a symptom and a cause, it is possible to use, for any one of specific low back pain and non-specific low back pain, a NSAIDs introduced GAG derivative capable of allowing control of dissociation rate of a physiologically active substance.

Myofascial pain syndrome (MPS) indicates a state in which a problem is not observed according to an image test or a blood test, but muscular pain or "wrick" continuously occurs for a long period of time (at least 2 to 3 months). Symptom of MPS is generally limited to muscles of 1 to 2 areas, and it is characterized in that an induration part (muscle induration) referred to as a trigger point is felt in affected muscle. Since the muscle induration causes micro damages in muscle due to over-load to muscle and muscle spasm is caused by the micro damages, the muscle is shrunken and stiffened. As a result, a tender point at which severe pain is caused upon an application of a physical force is observed, and in particular, the tender point causing related pain in a broad range including neighboring regions is referred to as a pain trigger point (or trigger point). The trigger point most frequently occurs in a neck region to a scapular region, a lumbodorsal part, and a femoral part.

As a therapeutic method, there are therapeutics based on using NSAIDs (internal or external administration), muscle relaxant, an anti-depressant, and an anti-spasm agent, and a trigger point injection therapeutics in which local anesthetic, neobitacain (registered trade mark) (pain suppressing agent (combination of dibucaine hydrochloride salt, sodium salicylic acid, and calcium bromide)), steroid, or noirotropin (registered trade mark) is injected.

In particular, although the local anesthetic trigger point injection generally used for MPS therapeutics can provide a constant analgesic effect, the effect is continued for 1 to 2 days at the most, and thus the treatment frequency is high. As such, there is a high need for a long acting analgesic which can reduce visiting times to hospital. In addition, although a nonsteroidal anti-inflammatory drug (NSAID), a muscle relaxant, an anti-depressant, or the like are administered as drug therapy, the effect is currently low. In addition, as most of the treatment subjects are senior people and local anesthetics exhibit a side effect on a cardiovascular system like bradysphygmia, arrhythmia, or the like and on a central nervous system like suppressed breathing or the like, there is a demand for a local pain suppressing agent having sustained effect and safety, and a NSAIDs introduced GAG derivative with controllable release is appropriate for the aforementioned use.

The NSAIDs introduced GAG derivative is suitable for use as a local intramuscular sustained-release analgesic for back pain like low back pain and muscular pain like myofascial pain syndrome as described above. In case of an intramuscular pharmaceutical, for example, the GAG derivative is relatively rapidly lost by metabolism. Thus, when a drug with relatively slow dissociation rate is used for such application, the effect may not exhibit as it is lost by metabolism before release of required amount of the drug. For such case, when a NSAIDs introduced GAG derivative with relatively fast drug dissociation rate, in which an electron withdrawing group is introduced to a spacer, is used, the drug can dissociate at a suitable level so that long-acting effect can be exhibited.

Furthermore, regarding the local intramuscular sustained-release analgesic for low back pain or muscle pain like myofascial pain syndrome described above, as a drug compound, a steroid introduced GAG derivative using steroid can be used instead of NSAIDs.

The administration interval for the pain suppressing agent of this embodiment is not particularly limited. For example, the administration interval is preferably 3 days or longer, more preferably 7 days or longer, even more preferably 10 days or longer, and particularly preferably 14 days or longer. For example, the pain suppressing effect of the pain suppressing agent of this embodiment is continued for 3 days or longer after the administration, more preferably 7 days or longer after the administration, even more preferably 10 days or longer after the administration, and particularly preferably 14 days or longer after the administration.

The present invention may contain, in addition to the aforementioned glycosaminoglycan derivative (hereinbelow, it may be also referred to as "first glycosaminoglycan derivative"), a second glycosaminoglycan derivative which is not coupled to a physiologically active substance described below. Namely, the present invention includes the following embodiments.

<1a> A second glycosaminoglycan derivative having a group derived from glycosaminoglycan and a spacer-forming group which forms a covalent bond with a group derived from glycosaminoglycan and has at least one substituent group selected from a group consisting of an electron withdrawing group, an electron donating group, and a sterically hindered group and a reactive functional group capable of forming a covalent bond to a physiologically active substance.

<2a> The second glycosaminoglycan derivative described in <1a>, in which the reactive functional group is at least one group selected from a hydroxy group, a carboxy group, and a derivative thereof and the covalent bond to a physiologically active substance is an ester bond.

<3a> The second glycosaminoglycan derivative described in <1a> or <2a>, in which the group derived from glycosaminoglycan and the spacer-forming group are covalently bonded through an amide bond.

<4a> The second glycosaminoglycan derivative described in any one of <1a> to <3a>, in which the spacer-forming group is a group derived from at least one selected from a group consisting of an amino alcohol, an amino acid, and a derivative thereof.

<5a> The second glycosaminoglycan derivative described in any one of <1a> to <4a>, in which the spacer-forming group is a group derived from an amino acid represented by the following formula (Ia):

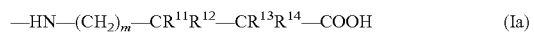

—HN—(CH$_2$)$_m$—CR$^{11}$R$^{12}$—CR$^{13}$R$^{14}$—COOH (Ia)

(in the formula, m is an integer of 0 to 12. $R^{11}$ to $R^{14}$ each independently represent a hydrogen atom, an electron withdrawing group, an electron donating group, or a sterically hindered group).

<6a> The second glycosaminoglycan derivative described in any one of <1a> to <4a>, in which the spacer-forming group is a group derived from an amino alcohol represented by the following formula (IIa):

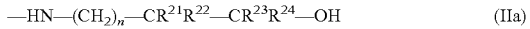
—HN—(CH$_2$)$_n$—CR$^{21}$R$^{22}$—CR$^{23}$R$^{24}$—OH    (IIa)

(in the formula, n is an integer of 0 to 12. $R^{21}$ to $R^{24}$ each independently represent a hydrogen atom, an electron withdrawing group, an electron donating group, or a sterically hindered group)

<7a> The second glycosaminoglycan derivative described in any one of <1a> to <6a>, in which the glycosaminoglycan is at least one selected from a group consisting of chondroitin sulfate, hyaluronic acid, heparin, heparan sulfate, and keratan sulfate.

<8a> A first glycosaminoglycan derivative obtained by covalent bond between the second glycosaminoglycan derivative described in any one of <1a> to <7a> and a physiologically active substance.

<9a> A controlled release preparation containing the second glycosaminoglycan derivative described in <8a>.

m and $R_{11}$ to $R^{14}$ in the formula (Ia) have the same meanings as m and $R^{11}$ to $R^{14}$ in the formula (I). Furthermore, m and $R^{21}$ to $R^{24}$ in the formula (IIa) have the same meanings as m and $R^{21}$ to $R^{24}$ in the formula (II).

By using the aforementioned second glycosaminoglycan derivative, the dissociation rate of a physiologically active substance can be controlled.

EXAMPLES

Hereinbelow, the present invention is explained in greater detail by referring to Examples and Test examples, but it is evident that the technical scope of the present invention is not limited to them. Meanwhile, except the dissociation ratio and introduction ratio, "%" is based on mass, unless specifically described otherwise.

<Example 1> Preparation of Betamethasone-Chondroitin Sulfate 1-1. Condensation Reaction of Boc-β-Alanine and Betamethasone 1 g (1.0 eq., 5.29 mmol) of Boc-β-alanine was dissolved in 18 mL of dichloromethane (DCM) and 12 mL of dimethyl formamide (DMF), and added with 2.07 g (1.0 eq., 5.29 mmol) of betamethasone and 194 mg (0.3 eq., 1.59 mmol) of N,N-dimethylaminopyridine (DMAP). After that, under ice cooling, 1.11 g (1.1 eq., 5.81 mmol) of water soluble carbodiimide (WSC, manufactured by Tokyo Chemical Industry Co., Ltd.) was added and stirred overnight at room temperature. After confirming by TLC the disappearance of the reacting materials, liquid fractionation extraction was performed 3 times using toluene and water, and the collected organic layer was washed in order with a saturated aqueous solution of NH$_4$Cl, a saturated aqueous solution of NaHCO$_3$, and a saturated aqueous solution of NaCl. After drying over magnesium sulfate, it was concentrated under reduced pressure by using an evaporator in water bath at 60° C., and as a result, 3.18 g of the desired Boc-β-alanine-betamethasone was obtained. Meanwhile, Boc represents a tert-butyloxycarbonyl group.

$^1$H-NMR signal assignment is given in the following.
$^1$H-NMR (500 MHz, CDCl$_3$) δ1.05 (3H, s), 1.13 (3H, m), 1.20 (1H, m), 1.46 (9H, s), 1.58-1.61 (4H, m), 1.99 (1H, m), 2.05 (1H, m), 2.15 (2H, m), 2.38 (1H, dd), 2.42 (1H, dd), 2.52 (1H, m), 2.62 (2H, t), 2.75 (1H, m), 3.38 (2H, t), 4.25 (1H, m), 4.95 (2H, s), 6.09 (1H, s), 6.29 (1H, d), 7.50 (1H, d).

1-2. De-Boc Protection Reaction of Boc-β-Alanine-Betamethasone 2 g of Boc-β-alanine-betamethasone was dissolved in 20 mL of tetrahydrofuran (THF), and under ice cooling, added with 15 mL of 4 M hydrochloric acid/ethyl acetate (HCl/AcOEt), and stirred for 7 hours. After confirming by TLC the disappearance of the reacting materials, it was concentrated under reduced pressure by using an evaporator in water bath at 40° C. As a result, the desired β-alanine-betamethasone hydrochloride salt was obtained in an amount of 1.2 g (two step yield of 73%).

$^1$H-NMR signal assignment is given in the following.
$^1$-NMR (500 MHz, CD$_3$OD) δ1.08 (3H, s), 1.12 (3H, m), 1.20 (1H, m), 1.54-1.62 (4H, m), 1.98-2.18 (4H, m), 2.38 (1H, dd), 2.42 (1H, dd), 2.52 (1H, m), 2.75 (1H, m), 2.91 (2H, t), 3.30 (2H, t), 4.27 (1H, m), 5.10 (2H, dd), 6.11 (1H, s), 6.30 (1H, d), 7.42 (1H, d).

1-3. Introduction of β-alanine-betamethasone hydrochloride salt to chondroitin sulfate 1 g of chondroitin sulfate (weight average molecular weight of about 40 kDa) was dissolved in 100 mL of water for injection (WFI) and 100 mL of ethanol (EtOH) and added with 199 mg (0.2 eq., 0.40 mmol) of β-alanine-betamethasone hydrochloride salt. After that, 187 mg (0.2 eq., 0.40 mmol) of 4-(4,6-dimethoxy-1,3,5-triazin-2-yl)-4-methylmoprpholinium chloride n-hydrate (DMT-MM) was added thereto and stirred overnight. Then, 750 mg of sodium hydrogen carbonate (NaHCO$_3$) was added, stirred for 3 hours, and added in order with 400 μL of acetic acid and 3 g of sodium chloride (NaCl). After stirring for 30 minutes, 200 mL of 90% EtOH/WFI was added to form precipitate. The supernatant was discarded and washing with 90% EtOH/WFI was performed 2 times. The obtained precipitate was dried overnight under reduced pressure, and as a desired GAG derivative (hereinbelow, also referred to as a conjugate), 760 mg of CS-betamethasone was obtained. As a result of obtaining the introduction ratio by a carbazole sulfate method, it was found to be 17%.

<Example 2> Preparation of Betamethasone (F)-Chondroitin Sulfate

Preparation of betamethasone (F)-chondroitin sulfate (i.e., betamethasone-chondroitin sulfate conjugate in which α-fluoro-β-alanine is used as a spacer-forming molecule) is shown in Scheme 2.

By using α-fluoro-β-alanine hydrochloride salt 1 as a reacting material and protecting the amino group of 1 with a tert-butoxycarbonyl (Boc) group, it was converted to the compound 2. After that, by subjecting it to a condensation reaction with betamethasone, the compound 3 was obtained. Subsequently, the Boc group of the compound 3 was removed under an acidic condition to convert it to the introduction precursor 4, which is an amine hydrochloride salt. Then, by performing introduction to chondroitin sulfate, the conjugate 5 was synthesized.

Scheme 2

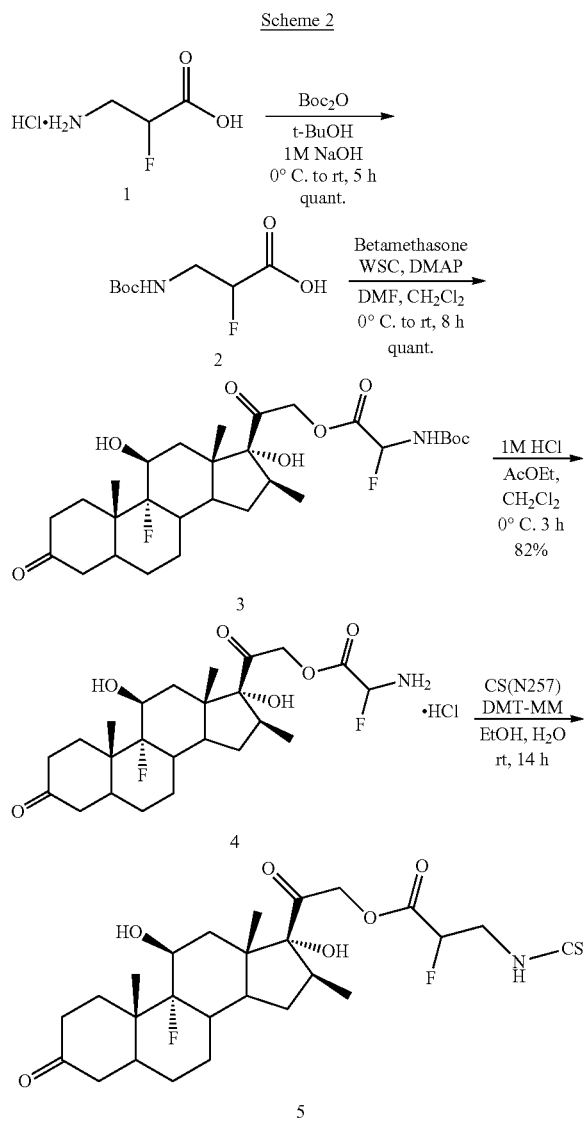

2-1. Boc Protection of α-fluoro-β-alanine hydrochloride salt 600 mg (1.0 eq., 4.18 mmol) of the α-fluoro-β-alanine hydrochloride salt 1 was dissolved in 24 mL of tert-butanol and 12 mL of 1 M sodium hydroxide (NaOH), and under ice cooling, added with 1.19 g (1.3 eq., 5.43 mmol) of di-tert-butyl bicarbonate (Boc$_2$O). After that, it was stirred overnight at room temperature. After confirming by thin layer chromatography (TLC) the disappearance of the reacting materials, it was concentrated under reduced pressure by using an evaporator in water bath at 40° C. Then, liquid fractionation extraction was performed 3 times using ethyl acetate and 1 M hydrochloric acid (HCl), and the collected organic layer was washed with a saturated aqueous solution of NaCl. After drying over magnesium sulfate, it was concentrated under reduced pressure by using an evaporator in water bath at 40° C. As a result, the desired compound 2 was obtained in an amount of 865 mg (yield of 99%).

$^1$H-NMR signal assignment is given in the following.
$^1$H-NMR (500 MHz, CDCl$_3$) δ1.45 (9H, s), 3.64-3.79 (2H, br), 4.98 (1H, br), 5.05 (1H, br).

2-2. Condensation Reaction Between the Compound 2 and Betamethasone 500 mg (1.0 eq., 2.41 mmol) of the compound 2 was dissolved in 30 mL of DMF, and added with 947 mg (1.0 eq., 2.41 mmol) of betamethasone and 89 mg (0.3 eq., 0.72 mmol) of DMAP. After that, under ice cooling, 694 mg (1.5 eq., 3.62 mmol) of WSC was added and stirred overnight at room temperature. After confirming by TLC the disappearance of the reacting materials, liquid fractionation extraction was performed 3 times using toluene and water, and the collected organic layer was washed in order with a saturated aqueous solution of ammonium chloride (NH$_4$Cl), a saturated aqueous solution of NaHCO$_3$, and a saturated aqueous solution of NaCl. After drying over magnesium sulfate, it was concentrated under reduced pressure by using an evaporator in water bath at 60° C., and the desired compound 3 was obtained in an amount of 1.4 g (yield of 99%).

$^1$H-NMR signal assignment is given in the following.
$^1$H-NMR (500 MHz, CDCl$_3$) δ1.04 (3H, d), 1.16 (4H, m), 1.46 (9H, s), 1.84-2.01 (6H, m), 2.31-2.65 (7H, m), 3.60-3.72 (2H, m), 4.41 (1H, d), 4.95-5.20 (3H, m), 6.12 (1H, s), 6.35 (1H, d), 7.21 (1H, d).

2-3. De-Boc Reaction of the Compound 3

250 mg of the compound 3 was dissolved in 20 mL of dichloromethane (DCM), and under ice cooling, added with 16 mL of 4 M hydrochloric acid/ethyl acetate (HCl/AcOEt), and stirred for 3 hours. After confirming by TLC the disappearance of the reacting materials, it was concentrated under reduced pressure by using an evaporator in water bath at 40° C. As a result, the desired introduction precursor 4 was obtained in an amount of 188 mg (yield of 82%).

$^1$H-NMR signal assignment is given in the following.
$^1$H-NMR (500 MHz, CD$_3$OD) δ1.04-1.80 (13H, m) 1.95-2.20 (4H, m), 2.31-2.80 (4H, m), 3.60-3.72 (2H, m), 4.20 (1H, m), 5.01 (1H, m), 5.35 (1H, m), 6.02 (1H, s), 6.28 (1H, d), 7.33 (1H, d).

2-4. Introduction of the Introduction Precursor 4 to Chondroitin Sulfate 1 g of chondroitin sulfate (weight average molecular weight of about 40 kDa) was dissolved in 80 mL of water for injection (WFI) and 80 mL of EtOH and added with 349 mg (0.34 eq., 0.68 mmol) of the introduction precursor 4. After that, 317 mg (0.34 eq., 0.68 mmol) of DMT-MM was added thereto and stirred overnight. Then, 3 g of NaCl was added, stirred for 30 minutes, and 160 mL of 90% ethanol (EtOH)/WFI was added to form precipitate. The supernatant was discarded and washing with 90% EtOH/WFI was performed 2 times. The obtained precipitate was dried overnight under reduced pressure, and as a result, 1.08 g of the target product 5 was obtained. As a result of obtaining the introduction ratio by a carbazole sulfate method, it was found to be 16%.

<Example 3> Preparation of Betamethasone (Cl)-Chondroitin Sulfate

Preparation of betamethasone (Cl)-chondroitin sulfate (i.e., betamethasone-chondroitin sulfate conjugate in which α-chloro-β-alanine is used as a spacer-forming molecule) is shown in Scheme 3.

By reacting the phthalimide 6 and the 2-chloroacrylonitrile 7, the compound 8 was prepared, and it was subjected to hydrolysis to obtain the α-chloro-β-alanine hydrochloride salt 9. Subsequently, the amino group of the α-chloro-β-alanine hydrochloride salt 9 was protected with Boc for conversion into the compound 10, and by performing a condensation reaction with betamethasone, the compound 11 was obtained. Furthermore, by removing the Boc group of the compound 11 under acidic condition, the introduction precursor 12 was yielded as an amine hydrochloride salt. After performing the introduction to chondroitin sulfate, the conjugate 13 was obtained.

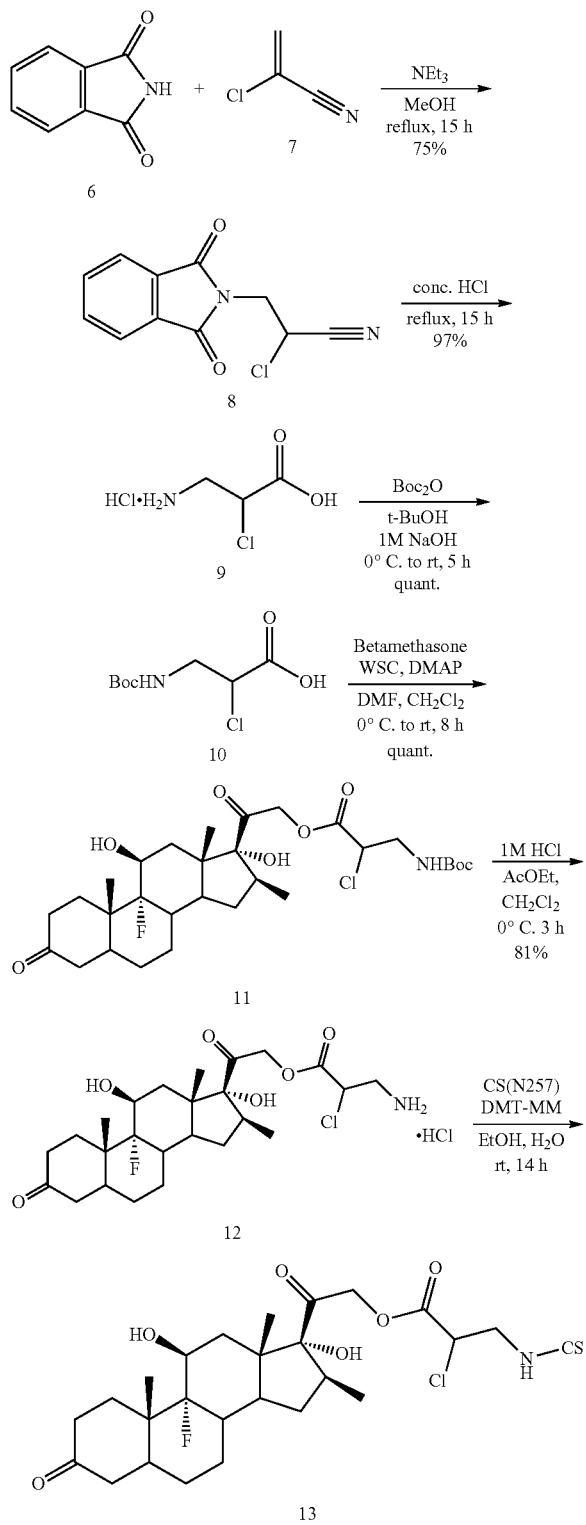

3-1. Synthesis of the Compound 8

To 5 g (1.0 eq., 33.4 mmol) of the phthalimide 6, 40 mL of methanol, 2.4 mL (0.5 eq., 16.7 mmol) of triethylamine and 5.4 mL (2.0 eq., 66.8 mmol) of 2-chloroacrylonitirile 7 were added, and stirred for 15 hours under reflux. After confirming by TLC the disappearance of the reacting materials, the solution was cooled to room temperature. The precipitate was washed with methanol and filtered under aspiration. The precipitate was dried under reduced pressure, and as a result, the target compound 8 was obtained in an amount of 5.9 g (yield of 75%).

$^1$H-NMR signal assignment is given in the following.
$^1$H-NMR (500 MHz, CDCl$_3$) δ4.26 (2H, dd), 4.95 (1H, t), 7.80 (2H, dd), 7.92 (2H, dd).

3-2. Synthesis of α-chloro-β-alanine hydrochloride salt 9

To 300 mg of the compound 8, 10 mL of conc. hydrochloric acid was added, and stirred for 15 hours under reflux. After confirming by TLC the disappearance of the reacting materials, the solution was cooled to room temperature, and the precipitate was filtered under aspiration. The precipitated solids obtained by drying of the resulting solution under reduced pressure were washed with acetone, and filtered again under aspiration. As a result of drying the solid under reduced pressure, the desired α-chloro-β-alanine hydrochloride salt 9 was obtained in an amount of 192 mg (yield of 97%).

$^1$H-NMR signal assignment is given in the following.
$^1$H-NMR (500 MHz, CD$_3$OD) δ3.49 (1H, dd), 3.60 (1H, dd), 4.68 (1H, t).

3-3. Boc Protection of α-chloro-β-alanine hydrochloride salt 9

168 mg (1.0 eq., 1.05 mmol) of the α-chloro-β-alanine hydrochloride salt 9 was dissolved in 6 mL of tert-butanol and 3 mL of 1 M NaOH, and under ice cooling, added with 300 mg (1.3 eq., 1.37 mmol) of Boc$_2$O. After that, it was stirred overnight at room temperature. After confirming by TLC the disappearance of the reacting materials, it was concentrated under reduced pressure by using an evaporator in water bath at 40° C. Then, liquid fractionation extraction was performed 3 times using ethyl acetate and 1 M HCl, and the collected organic layer was washed with a saturated aqueous solution of NaCl. After drying over magnesium sulfate, it was concentrated under reduced pressure by using an evaporator in water bath at 40° C. As a result, the desired compound 10 was obtained in an amount of 235 mg (yield: quant.).

$^1$H-NMR signal assignment is given in the following.
$^1$-NMR (500 MHz, CDCl$_3$) δ1.49 (9H, s), 3.64 (1H, br), 4.41-5.10 (2H, br).

3-4. Condensation Reaction Between the Compound 10 and Betamethasone 230 mg (1.0 eq., 1.03 mmol) of the compound 10 was dissolved in 10 mL of DMF and 10 mL of DCM, and added with 404 mg (1.0 eq., 1.03 mmol) of betamethasone and 63 mg (0.5 eq., 0.51 mmol) of DMAP. After that, under ice cooling, 297 mg (1.5 eq., 1.55 mmol) of WSC was added and stirred overnight at room temperature. After confirming by TLC the disappearance of the reacting materials, liquid fractionation extraction was performed 3 times using toluene and water, and the collected organic layer was washed in order with a saturated aqueous solution of NH$_4$Cl, a saturated aqueous solution of NaHCO$_3$, and a saturated aqueous solution of NaCl. After drying over magnesium sulfate, it was concentrated under reduced pressure by using an evaporator in water bath at 60° C., and the desired compound 11 was obtained in an amount of 625 mg (yield: quant.).

$^1$H-NMR signal assignment is given in the following.
$^1$H-NMR (500 MHz, CDCl$_3$) δ1.04-1.15 (7H, m), 1.46 (9H, s), 1.65 (4H, m), 1.95-2.23 (6H, m), 2.36-2.65 (5H, m) 3.78 (1H, m), 4.30-4.49 (3H, m), 4.95 (1H, m), 6.11 (1H, s), 6.35 (1H, d), 7.17 (1H, d).

3-5. De-Boc Reaction of the Compound 11

200 mg of the compound 11 was dissolved in 9 mL of DCM, and under ice cooling, added with 6 mL of 4 M HCl/AcOEt, and stirred for 2 hours. After confirming by TLC the disappearance of the reacting materials, it was concentrated under reduced pressure by using an evaporator in water bath at 40° C. The concentrate was washed with diethyl ether, and as a result, the desired introduction precursor 12 was obtained in an amount of 146 mg (yield of 81%).

$^1$H-NMR signal assignment is given in the following.
$^1$H-NMR (500 MHz, CD$_3$OD) δ1.04-1.70 (13H, m), 2.01-2.17 (5H, m), 2.36 (1H, m), 2.45 (2H, m), 2.89 (1H, m), 4.28 (1H, m), 5.15 (2H, m), 6.11 (1H, s), 6.30 (1H, d), 7.41 (1H, d).

3-6. Introduction of the Introduction Precursor 12 to Chondroitin Sulfate (Solubilization Treatment for 3 Hours)

200 mg of chondroitin sulfate (weight average molecular weight of about 40 kDa) was dissolved in 20 mL of WFI and 20 mL EtOH, and then added with 120 mg (0.56 eq., 0.22 mmol) of the introduction precursor 12. Then, it was added with 75 mg (0.56 eq., 0.22 mmol) of DMT-MM followed by stirring overnight. After that, the reaction solution was divided into two portions, which were then subjected to the following operations (1) and (2).

(1) With solubilization treatment for 3 hours: 75 mg of NaHCO$_3$ was added followed by stirring for 3 hours and addition in order of 40 µL of acetic acid and 300 mg of NaCl. After stirring for 30 minutes, 40 mL of 90% EtOH/WFI was added to form precipitate, the supernatant was discarded, and washing with 90% EtOH/WFI was performed 2 times. The obtained precipitate was dried overnight under reduced pressure, and as a result, 90 mg of the target product 13 was obtained. As a result of obtaining the introduction ratio by a carbazole sulfate method, it was found to be 14%.

(2) With no solubilization treatment: 300 mg of NaCl was added followed by stirring for 30 minutes and addition with 40 mL of 90% EtOH/WFI to form precipitate. The supernatant was discarded and washing with 90% EtOH/WFI was performed 2 times. The obtained precipitate was dried overnight under reduced pressure, and as a result, 97 mg of the target product 13 was obtained. As a result of obtaining the introduction ratio by a carbazole sulfate method, it was found to be 32%.

<Example 4> Preparation of Betamethasone (Br)-Chondroitin Sulfate

Preparation of betamethasone (Br)-chondroitin sulfate (i.e., betamethasone-chondroitin sulfate conjugate in which α-bromo-β-alanine is used as a spacer-forming molecule) is shown in Scheme 4.

After protecting the amino group of DL-isoserine 14 with Boc for conversion into the compound 15 and methyl esterification of the carboxyl group, it was converted into the compound 16. Then, the secondary hydroxy group was tosylated (compound 17) followed by reaction with lithium bromide for derivatization to the compound 18 in which a bromo group is introduced at a position. By further performing the hydrolysis of methyl ester, the compound 19 was synthesized followed by condensation with betamethasone (compound 20), deprotection of the Boc group (introduction precursor 21), and introduction to chondroitin sulfate, the conjugate 22 was synthesized.

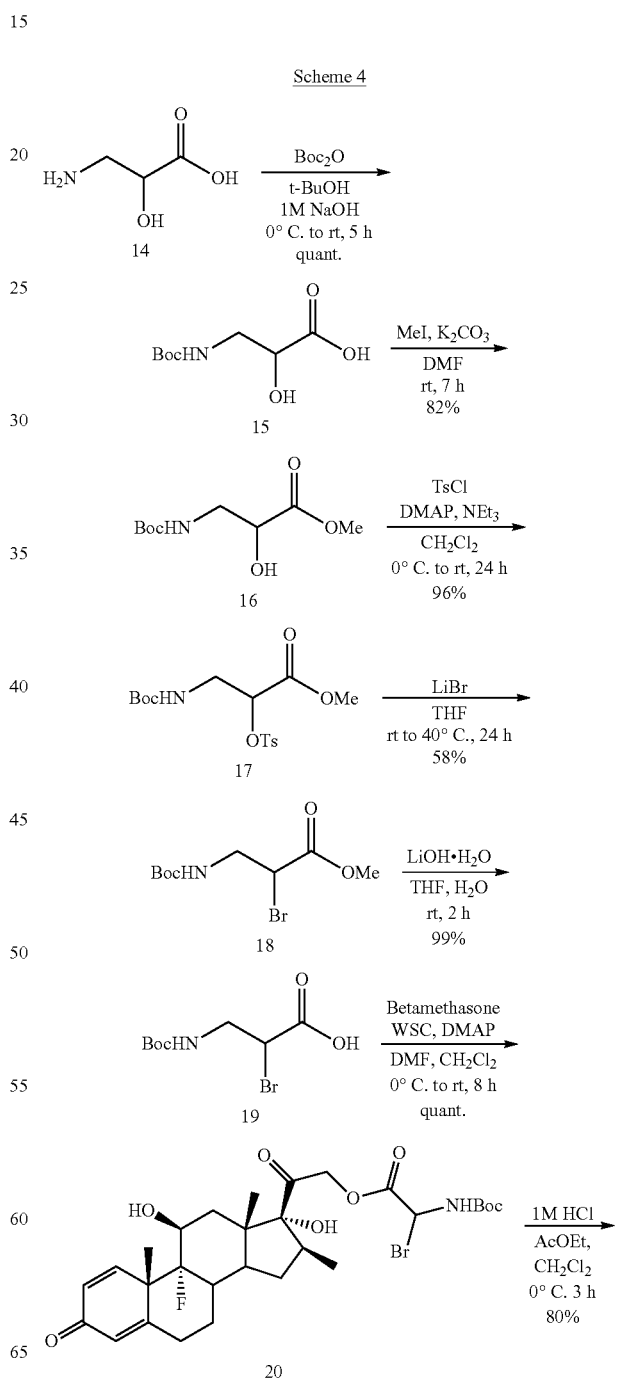

Scheme 4

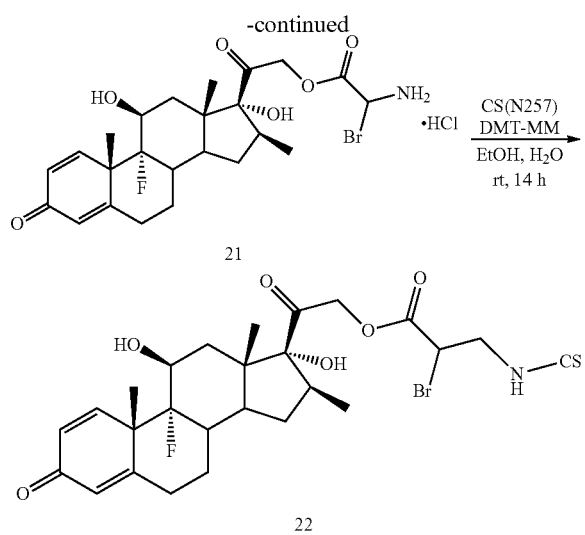

4-1. Synthesis of the Compound 15

1 g (1.0 eq., 9.52 mmol) of the DL-isoserine 14 was dissolved in 40 mL of tert-butanol and 20 mL of 1 M NaOH, and under ice cooling, added with 2.7 g (1.3 eq., 12.37 mmol) of $Boc_2O$. After that, it was stirred overnight at room temperature. After confirming by TLC the disappearance of the reacting materials, it was concentrated under reduced pressure by using an evaporator in water bath at 40° C. Then, liquid fractionation extraction was performed 3 times using ethyl acetate and 1 M HCl, and the collected organic layer was washed with a saturated aqueous solution of NaCl. After drying over magnesium sulfate, it was concentrated under reduced pressure by using an evaporator in water bath at 40° C. As a result, the desired compound 15 was obtained in an amount of 1.95 g (yield of 100%).

$^1$H-NMR signal assignment is given in the following.
$^1$H-NMR (500 MHz, $CDCl_3$) δ1.45 (9H, s), 3.51-3.65 (2H, m), 4.32 (1H, m), 5.10 (1H, br).

4-2. Synthesis of the Compound 16

800 mg (1.0 eq., 3.90 mmol) of the compound 15 was dissolved in 5 mL of DMF, and under ice cooling, added with 593 mg (1.1 eq., 4.29 mmol) of potassium carbonate and methyl iodide (1.1 eq., 4.29 mmol). After that, it was stirred overnight at room temperature under light shielding condition. After confirming by TLC the disappearance of the reacting materials, liquid fractionation extraction was performed 3 times using toluene and water. The collected organic layer was washed with a saturated aqueous solution of NaCl. After drying over magnesium sulfate, it was concentrated under reduced pressure by using an evaporator in water bath at 40° C. As a result, the desired compound 16 was obtained in an amount of 724 mg (yield of 82%).

$^1$H-NMR signal assignment is given in the following.
$^1$H-NMR (500 MHz, $CDCl_3$) δ1.48 (9H, s), 3.26 (1H, br), 3.50 (2H, d), 3.80 (3H, s), 4.28 (1H, dd), 4.88 (1H, br).

4-3. Synthesis of the Compound 17

660 mg (1.0 eq., 3.01 mmol) of the compound 16 was dissolved in 23 mL DCM, and added with 1.47 mL (3.5 eq., 10.54 mmol) of triethylamine and 184 mg (0.5 eq., 1.51 mmol) of DMAP. After that, under ice cooling, 1.72 g (3.0 eq., 9.03 mmol) of tosyl chloride was added thereto and stirred overnight at room temperature. After confirming by TLC the disappearance of the reacting materials, liquid fractionation extraction was performed 3 times by using DCM and water, and the collected organic layer was washed in order with a saturated aqueous solution of $NH_4Cl$, a saturated aqueous solution of $NaHCO_3$, and a saturated aqueous solution of NaCl. After drying over magnesium sulfate, it was concentrated under reduced pressure by using an evaporator in water bath at 40° C. The resulting reaction solution was purified by silica gel column chromatography (hexane:ethyl acetate=5:1) to obtain the compound 17 in an amount of 1.08 g (yield of 96%).

$^1$H-NMR signal assignment is given in the following.
$^1$H-NMR (500 MHz, $CDCl_3$) δ1.45 (9H, s), 2.45 (3H, s), 3.52-3.66 (2H, m), 3.77 (3H, s), 4.80 (1H, dd), 4.98 (1H, br), 7.35 (2H, d), 7.82 (2H, d).

4-4. Synthesis of the Compound 18

690 mg (1.0 eq., 1.84 mmol) of the compound 17 was dissolved in 7 mL of THF, and added with lithium bromide (5.0 eq., 9.22 mmol) followed by stirring overnight at 50° C. After confirming by TLC the disappearance of the reacting materials, liquid fractionation extraction was performed 3 times using ethyl acetate and water. The collected organic layer was washed in order with a saturated aqueous solution of $NH_4Cl$, a saturated aqueous solution of $NaHCO_3$, and a saturated aqueous solution of NaCl. After drying over magnesium sulfate, it was concentrated under reduced pressure by using an evaporator in water bath at 40° C. The resulting solution was purified by silica gel column chromatography (hexane:ethyl acetate=7:1) to obtain the compound 18 in an amount of 300 mg (yield of 58%).

$^1$H-NMR signal assignment is given in the following.
$^1$H-NMR (500 MHz, $CDCl_3$) δ1.48 (9H, s), 3.65 (2H, dd), 3.80 (3H, s), 4.38 (1H, dd), 5.01 (1H, br).

4-5. Synthesis of the Compound 19

400 mg (1.0 eq., 1.42 mmol) of the compound 18 was dissolved in 14 mL of THF and 7 mL of water, and under ice cooling, added with lithium hydroxide monohydrate (1.3 eq., 1.85 mmol). After that, it was stirred for 2 hours at room temperature. After confirming by TLC the disappearance of the reacting materials, liquid fractionation extraction was performed 3 times using 1 M HCl, diethyl ether, and water. The collected organic layer was washed with a saturated aqueous solution of NaCl. After drying over magnesium sulfate, it was concentrated under reduced pressure by using an evaporator in water bath at 40° C. As a result, the compound 19 was obtained in an amount of 380 mg (yield of 99%).

$^1$H-NMR signal assignment is given in the following.
$^1$H-NMR (500 MHz, $CDCl_3$) δ1.48 (9H, s), 3.67 (2H, m), 4.18 (1H, br), 4.42 (1H, dd), 5.09 (1H, br).

4-6. Condensation Reaction Between the Compound 19 and Betamethasone 422 mg (1.0 eq., 1.58 mmol) of the compound 19 was dissolved in 18 mL of DMF and 18 mL of DCM, and added with 589 mg (0.95 eq., 1.50 mmol) of betamethasone and 96 mg (0.5 eq., 0.79 mmol) of DMAP. After that, under ice cooling, 606 mg (2.0 eq., 3.16 mmol) of WSC was added and stirred overnight at room temperature. After confirming by TLC the disappearance of the reacting materials, liquid fractionation extraction was performed 3 times using toluene and water, and the collected organic layer was washed in order with a saturated aqueous solution of $NH_4Cl$, a saturated aqueous solution of $NaHCO_3$, and a saturated aqueous solution of NaCl. After drying over magnesium sulfate, it was concentrated under reduced pressure by using an evaporator in water bath at 60° C., and the desired compound 20 was obtained in an amount of 961 mg (yield of 95%).

$^1$H-NMR signal assignment is given in the following.

$^1$H-NMR (500 MHz, $CD_3OD$) δ1.11-1.84 (22H, m), 2.04-2.10 (5H, m), 2.30-2.50 (3H, m), 2.60 (1H, m), 3.53 (1H, m), 4.39 (2H, m), 4.50 (1H, m), 5.01 (1H, m), 6.11 (1H, s), 6.33 (1H, d), 7.18 (1H, d).

4-7. De-Boc Reaction of the Compound 20

819 mg of the compound 20 was dissolved in 20 mL of DCM and 52 mL of AcOEt, and under ice cooling, added with 48 mL of 4 M HCl/AcOEt, and stirred for 2 hours. After confirming by TLC the disappearance of the reacting materials, it was concentrated under reduced pressure by using an evaporator in water bath at 40° C. The concentrate was washed with diethyl ether, and as a result, the desired introduction precursor 21 was obtained in an amount of 589 mg (yield of 80%).

$^1$H-NMR signal assignment is given in the following.

$^1$H-NMR (500 MHz, $CD_3OD$) δ1.11-1.48 (11H, m), 1.67 (2H, m), 2.04-2.17 (5H, m) 2.20-2.61 (3H, m), 2.89 (1H, m) 3.55 (2H, m), 4.25 (1H, m), 4.45 (1H, d), 6.10 (1H, s), 6.30 (1H, d), 7.43 (1H, d).

4-8. Introduction of the Introduction Precursor 21 to Chondroitin Sulfate 100 mg of chondroitin sulfate (weight average molecular weight of about 40 kDa) was dissolved in 8 mL of WFI and 8 mL of EtOH and added with 24 mg (0.21 eq., 0.04 mmol) of the introduction precursor 21. After that, 20 mg (0.21 eq., 0.04 mmol) of DMT-MM was added thereto and stirred overnight. Then, 300 mg of NaCl was added, stirred for 30 minutes, and 20 mL of 90% EtOH/WFI was added to form precipitate. The supernatant was discarded and washing with 90% EtOH/WFI was performed 2 times. The obtained precipitate was dried overnight under reduced pressure, and as a result, 105 mg of the target product 22 was obtained. As a result of obtaining the introduction ratio by a carbazole sulfate method, it was found to be 15%.

<Example 5> Synthesis of CS (Cl)-Fenbufen

Synthesis of CS (Cl)-fenbufen is shown in Scheme 5.

By using 3-amino-1,2-propanediol (23) as a reacting material and protecting the amino group of 23 with Boc, the compound 24 was prepared. According to benzylation of the primary hydroxy group, the compound 25 was obtained. Subsequently, the secondary hydroxy group of the compound 25 was tosylated for derivatization to the compound 26 and also the tosyl group was converted to a chloro group. By performing hydrogenation reaction of the compound 27 as a chlorinated product by using palladium hydroxide, the compound 28 was obtained as a de-benzylated product, which was then subjected to condensation with fenbufen. Boc group of the compound 29 as a fenbufen condensate was removed under acidic condition for conversion into the introduction precursor 30 as an amine hydrochloride salt. According to introduction to CS, the conjugate 31 was obtained.

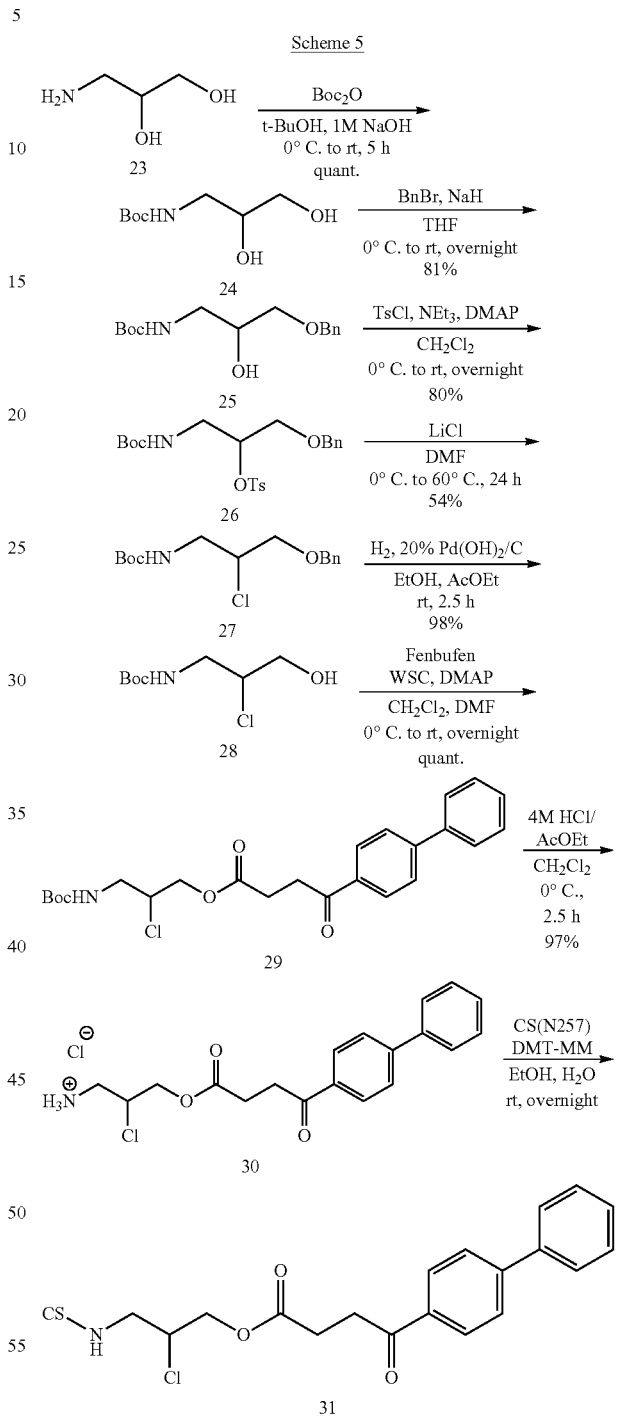

Scheme 5

5-1. Boc protection of 3-amino-1,2-propane diol 3 g (1.0 eq., 32.93 mmol) of the 3-amino-1,2-propane diol 23 was dissolved in 20 mL of tert-BuOH and 20 mL of 1 M NaOH, and under ice cooling, added with 20 mL of tert-BuOH solution containing 7.19 g (1.0 eq., 32.93 mmol) of $Boc_2O$. After that, it was stirred for 5 hours at room temperature. After confirming by TLC the disappearance of the reacting materials, it was concentrated under reduced pressure by using an evaporator in water bath at 50° C. Then, the reaction solution was neutralized by using 1 M HCl. Liquid fractionation extraction of the neutralized solution was performed 3 times by adding ethyl acetate and water, and the collected organic layer was washed with a saturated aqueous solution of NaCl. After drying over magnesium sulfate, it was concentrated under reduced pressure by using an evaporator in water bath at 40° C. As a result, the desired compound 2 was obtained in an amount of 6.3 g (yield: quant.).

$^1$H-NMR signal assignment is given in the following.
$^1$H-NMR (500 MHz, CDCl$_3$) δ1.45 (9H, s), 2.68-2.71 (1H, br), 2.75-2.81 (1H, br), 3.20 (2H, dd), 3.63 (2H, dd), 3.71 (1H, m) 4.91 (1H, br).

5-2. Benzylation Reaction of the Compound 24

1.91 g (1.0 eq., 9.96 mmol) of the compound 24 was dissolved in 20 mL of THF, and added with 251 mg (1.05 eq., 10.46 mmol) of sodium hydride followed by stirring for 15 minutes at room temperature. After that, under ice cooling, 1.24 mL (1.05 eq., 10.46 mmol) of benzyl chloride was added thereto and stirred overnight at room temperature. After confirming by TLC the disappearance of the reacting materials, the reaction solution was quenched with a saturated aqueous solution of NH$_4$Cl under ice cooling and liquid fractionation extraction was performed 3 times by using ethyl acetate and water. The collected organic later was washed in order with a saturated aqueous solution of NH$_4$Cl, a saturated aqueous solution of NaHCO$_3$, and a saturated aqueous solution of NaCl. After drying over magnesium sulfate, it was concentrated under reduced pressure by using an evaporator in water bath at 40° C. The resulting reaction solution was purified by silica gel column chromatography (hexane:ethyl acetate=5:1) to obtain the desired compound 25 in an amount of 2.3 g (yield of 81%).

$^1$H-NMR signal assignment is given in the following.
$^1$H-NMR (500 MHz, CDCl$_3$) δ1.44 (9H, s), 3.18 (1H, m), 3.29 (1H, m), 3.32 (1H, br), 3.45 (1H, dd), 3.54 (1H, dd), 3.63 (1H, m), 4.57 (2H, s), 4.91 (1H, br), 7.26-7.31 (5H, m).

5-3. Tosylation Reaction of the Compound 25

1.14 g (1.0 eq., 4.06 mmol) of the compound 25 was dissolved in 40 mL DCM, and added with 1.4 mL (2.5 eq., 10.14 mmol) of triethylamine, 248 mg (0.5 eq., 2.03 mmol) of DMAP, and 1.55 g (2.0 eq., 8.11 mmol) of tosyl chloride under ice cooling followed by stirring overnight at room temperature. After confirming by TLC the disappearance of the reacting materials, the reaction solution was quenched with a saturated aqueous solution of NH$_4$Cl under ice cooling and liquid fractionation extraction was performed 3 times by using DCM and water. The collected organic layer was washed in order with a saturated aqueous solution of NH$_4$Cl, a saturated aqueous solution of NaHCO$_3$, and a saturated aqueous solution of NaCl. After drying over magnesium sulfate, it was concentrated under reduced pressure by using an evaporator in water bath at 40° C. The resulting reaction solution was purified by silica gel column chromatography (hexane:ethyl acetate=5:1) to obtain the desired compound 26 in an amount of 1.4 g (yield of 80%).

$^1$H-NMR signal assignment is given in the following.
$^1$H-NMR (500 MHz, CDCl$_3$) δ1.55 (9H, s), 2.44 (3H, s), 3.35 (1H, m), 3.51 (1H, m), 3.53 (2H, d), 4.10 (1H, m), 4.39 (2H, dd), 7.20-7.79 (9H, m).

5-4. Chlorination Reaction of the Compound 26

425 mg (1.0 eq., 0.98 mmol) of the compound 26 was dissolved in 4 mL of DMF, and added with 207 mg (5.0 eq., 4.89 mmol) of lithium chloride followed by stirring overnight at room temperature. After confirming by TLC the disappearance of the reacting materials, the reaction solution was quenched with a saturated aqueous solution of NH$_4$Cl under ice cooling and liquid fractionation extraction was performed 3 times by using toluene and water. The collected organic layer was washed with a saturated aqueous solution of NaCl. After drying over magnesium sulfate, it was concentrated under reduced pressure by using an evaporator in water bath at 60° C. The resulting reaction solution was purified by silica gel column chromatography (hexane:ethyl acetate=9:1) to obtain the desired compound 27 in an amount of 158 mg (yield of 54%).

$^1$H-NMR signal assignment is given in the following.
$^1$H-NMR (500 MHz, CDCl$_3$) δ1.44 (9H, s), 3.37-3.64 (4H, m), 4.14 (1H, m), 4.59 (2H, dd), 7.29-7.38 (5H, m).

5-5. De-Benzylation Reaction of the Compound 27

100 mg (1.0 eq., 0.33 mmol) of the compound 27 was dissolved in 2 mL of AcOEt and 1 mL of EtOH, and added with 70 mg (0.3 eq., 0.10 mmol) of 20% palladium hydroxide. After adding hydrogen 3 times, it was stirred overnight at room temperature. After confirming by TLC the disappearance of the reacting materials, the reaction solution was filtered through Celite, and it was concentrated under reduced pressure by using an evaporator in water bath at 50° C. As a result, the desired compound 28 was obtained in an amount of 69 mg (yield of 98%).

$^1$H-NMR signal assignment is given in the following.
$^1$H-NMR (500 MHz, CDCl$_3$) δ1.45 (9H, s), 3.34 (1H, m), 3.58 (1H, m), 3.74 (1H, m), 3.87 (1H, m), 4.01 (1H, m), 5.01 (1H, br).

5-6. Condensation Reaction Between the Compound 28 and Fenbufen 65 mg (1.0 eq., 0.31 mmol) of the compound 28 was dissolved in 1 mL of DMF and 4 mL of DCM, and added with 83 mg (1.05 eq., 0.33 mmol) of fenbufen and 19 mg (0.5 eq., 0.16 mmol) of DMAP. Then, under ice cooling, 119 mg (2.0 eq., 0.62 mmol) of WSC was added followed by stirring overnight at room temperature. After confirming by TLC the disappearance of the reacting materials, the reaction solution was quenched with a saturated aqueous solution of NH$_4$Cl under ice cooling and liquid fractionation extraction was performed 3 times by using toluene and water. The collected organic layer was washed in order with a saturated aqueous solution of NH$_4$Cl, a saturated aqueous solution of NaHCO$_3$, and a saturated aqueous solution of NaCl. After drying over magnesium sulfate, it was concentrated under reduced pressure by using an evaporator in water bath at 60° C., and the desired compound 29 was obtained in an amount of 139 mg (yield of 100%).

$^1$H-NMR signal assignment is given in the following.
$^1$H-NMR (500 MHz, CDCl$_3$) δ1.45 (9H, s), 2.84 (2H, m), 3.40-3.42 (3H, m), 3.53 (1H, m), 4.20 (1H, m), 4.35 (2H, m), 5.01 (1H, br), 7.16-8.07 (9H, m).

5-7. De-Boc Reaction of the Compound 29

138 mg of the compound 29 was dissolved in 5 mL of DCM, and under ice cooling, added with 2 mL of 4 M HCl/AcOEt, and stirred for 2.5 hours. After confirming by TLC the disappearance of the reacting materials, it was concentrated under reduced pressure by using an evaporator in water bath at 40° C. The concentrate was washed with diethyl ether, and as a result, the desired introduction precursor 30 was obtained in an amount of 115 mg (yield of 97%).

$^1$H-NMR signal assignment is given in the following.

$^1$H-NMR (500 MHz, CD$_3$OD) δ2.82 (2H, dt), 3.52 (2H, m), 3.68 (2H, m), 3.82 (1H, m), 4.40 (2H, m), 7.43-8.13 (9H, m).

5-8-1. Introduction of the Introduction Precursor 30 to CS (Injected with 0.22 Eq.)

200 mg of CS (weight average molecular weight of about 40 kDa) was dissolved in 16 mL of WFI and 16 mL of EtOH and added with 33 mg (0.22 eq., 0.087 mmol) of the introduction precursor 30 and 41 mg (0.22 eq., 0.087 mmol) of DMT-MM followed by stirring overnight. Then, 600 mg of NaCl and 80 mL of 90% EtOH/WFI were added to form precipitate. The supernatant was discarded and washing with 90% EtOH/WFI was performed 2 times. The obtained precipitate was dried overnight under reduced pressure, and as a result, 198 mg of the target product 31 was obtained. As a result of obtaining the introduction ratio by a carbazole sulfate method, it was found to be 15%.

5-8-2. Introduction of the Introduction Precursor 30 to CS (Injected with 0.28 Eq.)

200 mg of CS (weight average molecular weight of about 40 kDa) was dissolved in 16 mL of WFI and 16 mL of EtOH and added with 43 mg (0.28 eq., 0.11 mmol) of the introduction precursor 8 and 52 mg (0.28 eq., 0.11 mmol) of DMT-MM followed by stirring overnight. Then, 600 mg of NaCl and 80 mL of 90% EtOH/WFI were added to form precipitate. The supernatant was discarded and washing with 90% EtOH/WFI was performed 2 times. The obtained precipitate was dried overnight under reduced pressure, and as a result, 198 mg of the target product 31 was obtained. As a result of obtaining the introduction ratio by a carbazole sulfate method, it was found to be 19%.

<Example 6> Synthesis of CS (F)-Fenbufen

Synthesis of CS (F)-fenbufen is shown in scheme 6

After converting the hydroxy group of the compound 25 to fluorine to have the compound 32, the benzyl group was deprotected to obtain the compound 33. It was then subjected to condensation with fenbufen for conversion into the compound 34. De-Boc reaction was performed subsequently to have the introduction precursor 35. Finally, the introduction precursor 35 was introduced to CS to obtain the conjugate 36.

Scheme 6

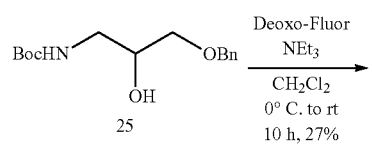

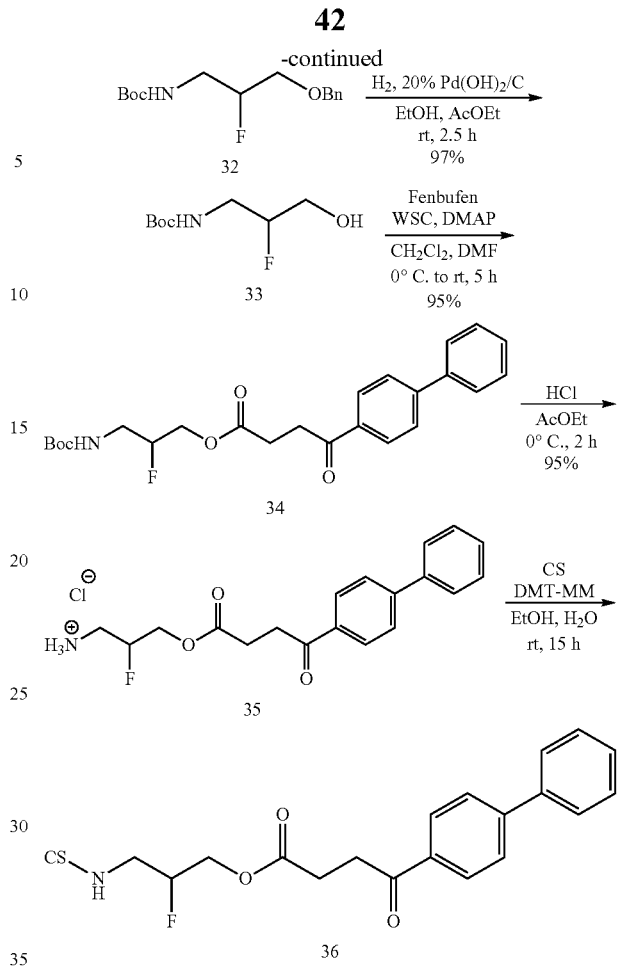

6-1. Fluorination Reaction of the Compound 25

1.5 g (1.0 eq., 5.34 mmol) of the compound 25 was dissolved in 18 mL DCM, and added with 7.3 mL (10.0 eq., 53.4 mmol) of triethylamine and 2.95 mL (3.0 eq., 16.01 mmol) of Deoxo-Fluoro under ice cooling followed by stirring overnight at room temperature. After confirming an appearance of a new spot by TLC, the reaction solution was quenched with a saturated aqueous solution of NaHCO$_3$ under ice cooling. Then, liquid fractionation extraction was performed 3 times by using DCM and water. The collected organic layer was washed with a saturated aqueous solution of NaCl. After drying over magnesium sulfate, it was concentrated under reduced pressure by using an evaporator in water bath at 40° C. The resulting solution was purified by silica gel column chromatography (hexane:ethyl acetate=10:1) to obtain the desired compound 32 in an amount of 408 mg (yield of 27%).

$^1$H-NMR signal assignment is given in the following.

$^1$H-NMR (500 MHz, CDCl$_3$) δ1.44 (9H, s), 3.42 (2H, m), 3.65 (2H, m), 4.56 (2H, dd), 4.70 (1H, m), 4.83 (1H, br), 7.20-7.36 (5H, m).

6-2. De-Benzylation Reaction of the Compound 32

25 mg (1.0 eq., 0.09 mmol) of the compound 32 was dissolved in 2 mL of AcOEt and 1 mL of EtOH, and added with 19 mg (0.3 eq., 0.03 mmol) of 20% palladium hydroxide. After adding hydrogen 3 times, it was stirred overnight at room temperature. After confirming by TLC the disappearance of the reacting materials, the reaction solution was filtered through Celite, and it was concentrated under reduced pressure by using an evaporator in water bath at 50° C. As a result, the desired compound 33 was obtained in an amount of 17 mg (yield of 97%).

$^1$H-NMR signal assignment is given in the following.

$^1$H-NMR (500 MHz, CDCl$_3$) δ1.45 (9H, s), 3.39-3.55 (4H, m), 3.73 (1H, m).

6-3. Condensation Reaction Between the Compound 33 and Fenbufen 15 mg (1.0 eq., 0.08 mmol) of the compound 33 was dissolved in 1 mL of DMF and 3 mL of DCM, and added with 21 mg (1.05 eq., 0.08 mmol) of fenbufen and 4.7 mg (0.5 eq., 0.04 mmol) of DMAP. Then, under ice cooling, 30 mg (2.0 eq., 0.16 mmol) of WSC was added followed by stirring overnight at room temperature. After confirming by TLC the disappearance of the reacting materials, the reaction solution was quenched with a saturated aqueous solution of NH$_4$Cl under ice cooling and liquid fractionation extraction was performed 3 times by using toluene and water. The collected organic layer was washed in order with a saturated aqueous solution of NH$_4$Cl, a saturated aqueous solution of NaHCO$_3$, and a saturated aqueous solution of NaCl. After drying over magnesium sulfate, it was concentrated under reduced pressure by using an evaporator in water bath at 60° C., and the desired compound 34 was obtained in an amount of 32 mg (yield of 95%).

$^1$H-NMR signal assignment is given in the following.

$^1$H-NMR (500 MHz, CDCl$_3$) δ1.45 (9H, s), 2.80 (2H, dt), 3.37-3.53 (6H, m), 4.33 (1H, m), 7.41-8.07 (9H, m).

6-4. De-Boc Reaction of the Compound 34

142 mg of the compound 34 was dissolved in 5 mL of DCM, and under ice cooling, added with 2 mL of 4 M HCl/AcOEt, and stirred for 2 hours. After confirming by TLC the disappearance of the reacting materials, it was concentrated under reduced pressure by using an evaporator in water bath at 40° C. The concentrate was washed with diethyl ether, and as a result, the desired introduction precursor 35 was obtained in an amount of 115 mg (yield of 95%).

$^1$H-NMR signal assignment is given in the following.

$^1$H-NMR (500 MHz, CD$_3$OD) δ2.82 (2H, m), 3.26 (2H, t), 3.45 (2H, m), 3.67 (2H, m), 4.40 (1H, m), 7.43-8.13 (9H, m).

6-5-1. Introduction of the Introduction Precursor 35 to CS (Injected with 0.24 Eq.)

200 mg of CS (weight average molecular weight of about 40 kDa) was dissolved in 16 mL of WFI and 16 mL of EtOH and added with 35 mg (0.24 eq., 0.095 mmol) of the introduction precursor 35 and 45 mg (0.24 eq., 0.095 mmol) of DMT-MM followed by stirring overnight. Then, 600 mg of NaCl and 90 mL of 90% EtOH/WFI were added to form precipitate. The supernatant was discarded and washing with 90% EtOH/WFI was performed 2 times. The obtained precipitate was dried overnight under reduced pressure, and as a result, 195 mg of the target product 36 was obtained. As a result of obtaining the introduction ratio by a carbazole sulfate method, it was found to be 9%.

6-5-2. Introduction of the Introduction Precursor 35 to CS (Injected with 0.26 Eq.)

200 mg of CS (weight average molecular weight of about 40 kDa) was dissolved in 16 mL of WFI and 16 mL of EtOH and added with 43 mg (0.26 eq., 0.103 mmol) of the introduction precursor 8 and 49 mg (0.26 eq., 0.103 mmol) of DMT-MM followed by stirring overnight. Then, 600 mg of NaCl and 90 mL of 90% EtOH/WFI were added to form precipitate. The supernatant was discarded and washing with 90% EtOH/WFI was performed 2 times. The obtained precipitate was dried overnight under reduced pressure, and as a result, 196 mg of the target product 36 was obtained. As a result of obtaining the introduction ratio by a carbazole sulfate method, it was found to be 12%.

<Example 7> Synthesis of CS (F,F)-Felbinac (Hereinbelow, Also Referred to as FB-(F,F)-CS)

Synthesis of CS (F,F)-felbinac is shown in Scheme 7.

By using the compound 37 as a starting material and hydrolyzing ethyl ester at one side, the compound 38 was obtained. Ethyl ester of the compound 38 was reacted with benzylamine to give the compound 39 as an amide product. Subsequently, the amide and carboxylic acid were simultaneously reduced to synthesize the compound 40. Further, after deprotecting the benzyl group of the compound 40 and protecting the Boc group with an amino group, the compound 42 and felbinac were subjected to a condensation reaction. Furthermore, the Boc group of the compound 43 as a felbinac condensate was deprotected for derivatization into the introduction precursor 44. Finally, it was introduced to CS to obtain the conjugate 45.

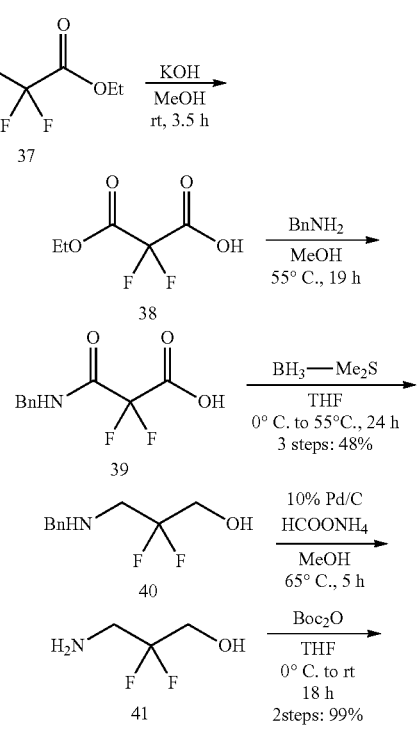

Scheme 7

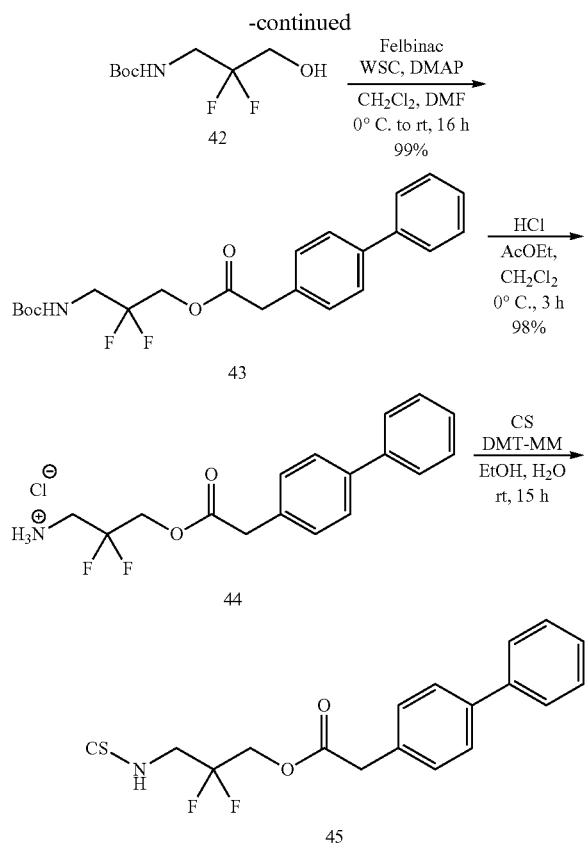

7-1-1. Conversion of the Compound 37 to the Compound 39

5 g (1.0 eq., 25.49 mmol) of the compound 37 was dissolved in 40 mL of methanol, and 30 mL of methanol solution of sodium hydroxide (1.43 g (1.0 eq., 25.49 mmol)) was added dropwise thereto. It was then stirred for 3 hours at room temperature. After confirming by TLC the disappearance of the reacting materials, benzyl amine (8.4 mL (3.0 eq., 76.47 mmol)) was added and stirred overnight at 55° C. The reaction solution was concentrated under reduced pressure by using an evaporator, and the precipitated solids were added with diethyl ether followed by washing and filtering. The washed solids were dissolved in 1 M HCl. Then, liquid fractionation extraction was performed 3 times using ethyl acetate. The collected organic layer was washed with a saturated aqueous solution of NaCl. After drying over magnesium sulfate, it was concentrated under reduced pressure by using an evaporator in water bath at 40° C. to obtain the residues (compound 39). It was directly subjected to the following reducing reaction.

7-1-2. Reducing Reaction of the Compound 39

4.9 g (1.0 eq., 21.35 mmol) of the compound 39 was dissolved in 35 mL of THF, and added dropwise at 0° C. with a solution in which dimethyl sulfide borane (8.2 mL (4.0 eq., 85.41 mmol)) is added in 15 mL of THF. After stirring for 1 hour at 0° C., it was again stirred for 3 and half hours at room temperature and overnight at 55° C. After confirming an appearance of a new spot by TLC, the reaction was quenched by using 1 M HCl, and liquid fractionation extraction was performed 3 times by using ethyl acetate and water. The collected organic layer was washed in order with 1 M aqueous solution of NaOH and a saturated aqueous solution of NaCl. After drying over magnesium sulfate, it was concentrated under reduced pressure by using an evaporator in water bath at 40° C. The resulting solution was purified by silica gel column chromatography (hexane:ethyl acetate=2:1) to obtain the desired compound 40 in an amount of 2.5 g (3 step yield of 48% from the compound 37).

$^{1}$H-NMR signal assignment is given in the following.
$^{1}$H-NMR (500 MHz, CDCl$_{3}$) δ3.12 (2H, dd), 3.87-3.93 (4H, m), 7.26-7.37 (5H, m).

7-2-1. De-Benzylation Reaction of the Compound 40

1.04 g (1.0 eq., 5.17 mmol) of the compound 40 was dissolved in 9 mL of methanol, and added with 550 mg of 10% palladium carbon and 1.63 g (5.0 eq., 25.86 mmol) of ammonium formate. It was then stirred for 5 hours at 65° C. After confirming by TLC the disappearance of the reacting materials, the reaction solution was filtered through Celite, and pH was adjusted to about 3 by adding dropwise 1 M HCl thereto. After that, methanol was removed using an evaporator and washing was carried out 2 times using ethyl acetate. Obtained aqueous layer was added with 1 M NaOH to adjust pH to about 10 to obtain an aqueous solution of the compound 41. It was directly subjected to the following Boc reaction.

7-2-2. Boc Protection of the Compound 41

50 mL of THF was added to 50 mL of aqueous solution of the compound 41, and then reacted with 1.13 g (1.0 eq., 5.17 mmol) of Boc$_{2}$O at 0° C. It was then stirred overnight. After confirming by TLC the disappearance of the reacting materials, THF was removed by using an evaporator. The residual liquid was added with ethyl acetate, and liquid fractionation extraction was performed 3 times. The collected organic layer was washed with a saturated aqueous solution of NaCl. After drying over magnesium sulfate, it was concentrated under reduced pressure by using an evaporator in water bath at 40° C. As a result, the solids are obtained, which were then washed with hexane to obtain 1.08 g of the desired compound 42 (2 step yield of 99% from the compound 18).

$^{1}$H-NMR signal assignment is given in the following.
$^{1}$H-NMR (500 MHz, CDCl$_{3}$) δ1.46 (9H, s), 3.54 (2H, ddd), 3.67 (2H, ddd), 3.95 (1H, m), 4.98 (1H, br).

7-3. Condensation Reaction Between the Compound 42 and Felbinac 300 mg (1.0 eq., 1.42 mmol) of the compound 42 was dissolved in 10 mL of DCM and 1 mL of DMF, and added with 317 mg (1.05 eq., 1.49 mmol) of felbinac and 52 mg (0.3 eq., 0.426 mmol) of DMAP. Then, under ice cooling, 545 mg (2.0 eq., 2.84 mmol) of WSC was added followed by stirring overnight at room temperature. After confirming by TLC the disappearance of the reacting materials, the reaction solution was quenched with a saturated aqueous solution of NH$_{4}$Cl under ice cooling and liquid fractionation extraction was performed 3 times by using toluene and water. The collected organic layer was washed in order with a saturated aqueous solution of NH$_{4}$Cl, a saturated aqueous solution of NaHCO$_{3}$, and a saturated aqueous solution of NaCl. After drying over magnesium sulfate, it was concentrated under reduced pressure by using an evaporator in water bath at 60° C., and the residues (compound 43) was obtained in an amount of 570 mg (yield of 99%). It was directly subjected to the following de-Boc reaction.

7-4. De-Boc Reaction of the Compound 43

570 mg of the compound 43 was dissolved in 15 mL of DCM, and under ice cooling, added with 6 mL of 4 M HCl/AcOEt, and stirred for 3 hours. After confirming by TLC the disappearance of the reacting materials, it was concentrated under reduced pressure by using an evaporator in water bath at 40° C. The residues were washed with diethyl ether, and as a result, the desired introduction precursor 44 was obtained in an amount of 471 mg (yield of 98%).

$^1$H-NMR signal assignment is given in the following.

$^1$H-NMR (500 MHz, CD$_3$OD) δ3.45 (2H, m), 3.83 (2H, s), 4.52 (2H, dd), 4.62 (2H, br), 7.36-7.64 (9H, m).

7-5-1. Introduction of the Introduction Precursor 44 to CS (Injected with 0.28 Eq.)

200 mg of CS (weight average molecular weight of about 40 kDa) was dissolved in 16 mL of WFI and 16 mL of EtOH and added with 34 mg (0.28 eq., 0.111 mmol) of the introduction precursor 44 and 52 mg (0.28 eq., 0.111 mmol) of DMT-MM followed by stirring overnight. Then, 600 mg of NaCl and 90 mL of 90% EtOH/WFI were added to form precipitate. The supernatant was discarded and washing with 90% EtOH/WFI was performed 2 times. The obtained precipitate was dried overnight under reduced pressure, and as a result, 202 mg of the target product 45 was obtained. As a result of obtaining the introduction ratio by a carbazole sulfate method, it was found to be 13%.

7-5-2. Introduction of the Introduction Precursor 44 to CS (Injected with 0.24 Eq.)

200 mg of CS (weight average molecular weight of about 40 kDa) was dissolved in 16 mL of WFI and 16 mL of EtOH and added with 29 mg (0.24 eq., 0.095 mmol) of the introduction precursor 44 and 45 mg (0.24 eq., 0.095 mmol) of DMT-MM followed by stirring overnight. Then, 600 mg of NaCl and 90 mL of 90% EtOH/WFI were added to form precipitate. The supernatant was discarded and washing with 90% EtOH/WFI was performed 2 times. The obtained precipitate was dried overnight under reduced pressure, and as a result, 200 mg of the target product 45 was obtained. As a result of obtaining the introduction ratio by a carbazole sulfate method, it was found to be 12%.

<Example 8> Synthesis of CS (F,F)-Indomethacin (Hereinbelow, Also Referred to as IM-(F,F)-CS)

Synthesis of CS (F,F)-indomethacin is shown in Scheme 8.

According to condensation between the compound 1 and indomethacin to give the compound 2, the Boc group was removed under an acidic condition for conversion into the introduction precursor 3 as an amine hydrochloride salt. By performing the introduction to CS, the conjugate 4 was obtained.

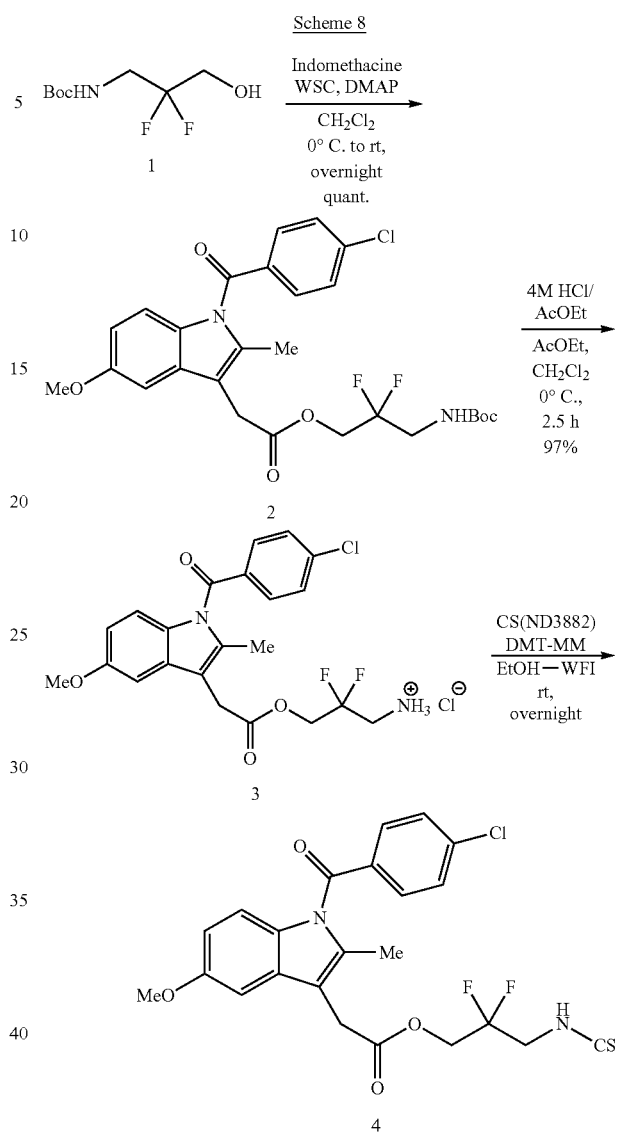

Scheme 8

8-1. Condensation Reaction Between the Compound 1 and Indomethacin 100 mg (1.0 eq., 0.47 mmol) of the compound 1 was dissolved in 10 mL of DCM, and added with 178 mg (1.05 eq., 0.50 mmol) of indomethacin and 17 mg (0.3 eq., 0.14 mmol) of DMAP. Then, under ice cooling, 182 mg (2.0 eq., 0.95 mmol) of WSC was added followed by stirring overnight at room temperature. After confirming by TLC the disappearance of the reacting materials, the reaction solution was quenched with a saturated aqueous solution of NH$_4$Cl under ice cooling and liquid fractionation extraction was performed 3 times by using DCM and water. The collected organic layer was washed in order with a saturated aqueous solution of NH$_4$Cl, a saturated aqueous solution of NaHCO$_3$, and a saturated aqueous solution of NaCl. After drying over magnesium sulfate, it was concentrated under reduced pressure by using an evaporator in water bath at 40° C., and the desired compound 2 was obtained in an amount of 260 mg (yield: quant.).

8-2. De-Boc Reaction of the Compound 2

260 mg of the compound 2 was dissolved in 7 mL of DCM, and under ice cooling, added with 3 mL of 4 M HCl/AcOEt, and stirred for 2.5 hours. After confirming by TLC the disappearance of the reacting materials, it was concentrated under reduced pressure by using an evaporator in water bath at 40° C. The residues were washed with diethyl ether, and as a result, the desired introduction precursor 3 was obtained in an amount of 223 mg (yield of 97%).

$^1$H-NMR signal assignment is given in the following.
$^1$H-NMR (500 MHz, CD$_3$OD) δ2.36 (3H, s), 3.51 (2H, m), 3.84 (3H, s), 3.90 (2H, s), 4.55 (2H, m), 6.72-7.71 (7H, m).

8-3. Introduction of the Introduction Precursor 3 to CS (Injected with 0.3 Eq.)

639 mg of CS (weight average molecular weight of about 20 kDa) was dissolved in 13 mL of WFI and 13 mL of EtOH and added with 186 mg (0.3 eq., 0.41 mmol) of the introduction precursor 3 and 179 mg (0.3 eq., 0.41 mmol) of DMT-MM followed by stirring overnight. Then, it was added with 620 mg of NaCl and the resulting solution was added dropwise to 60 mL of 95% EtOH/WFI to form precipitate. The supernatant was discarded and washing with 90% EtOH/WFI and 95% EtOH/WFI was performed 2 times for each. The obtained precipitate was dried overnight under reduced pressure, and as a result, 736 mg of the target product 4 was obtained. As a result of obtaining the introduction ratio by $^1$H-NMR, it was found to be 28%.

<Example 9> Synthesis of CS (F,F)-Ketoprofen (Hereinbelow, Also Referred to as KP-(F,F)-CS)

Synthesis of CS (F,F)-ketoprofen is shown in Scheme 9.

After condensation between the compound 1 and ketoprofen was performed to give the compound 5, the Boc group was removed under an acidic condition for conversion into the introduction precursor 6 as an amine hydrochloride salt. By performing the introduction to CS, the conjugate 7 was obtained.

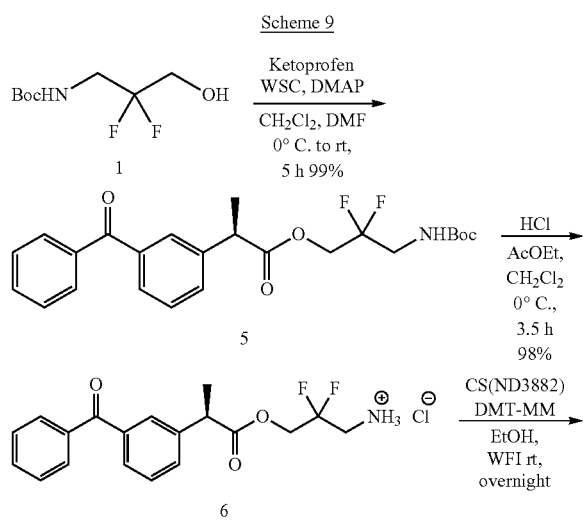

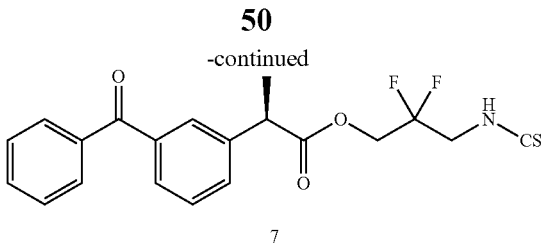

9-1. Condensation Reaction Between the Compound 1 and Ketoprofen 100 mg (1.0 eq., 0.47 mmol) of the compound 1 was dissolved in 3 mL of DCM, and added with 127 mg (1.05 eq., 0.50 mmol) of ketoprofen and 17 mg (0.3 eq., 0.14 mmol) of DMAP. Then, under ice cooling, 182 mg (2.0 eq., 0.95 mmol) of WSC was added followed by stirring overnight at room temperature. After confirming by TLC the disappearance of the reacting materials, the reaction solution was quenched with a saturated aqueous solution of NH$_4$Cl under ice cooling and liquid fractionation extraction was performed 3 times by using DCM and water. The collected organic layer was washed in order with a saturated aqueous solution of NH$_4$Cl, a saturated aqueous solution of NaHCO$_3$, and a saturated aqueous solution of NaCl. After drying over magnesium sulfate, it was concentrated under reduced pressure by using an evaporator in water bath at 40° C., and the desired compound 5 was obtained in an amount of 210 mg (yield of 99%).

9-2. De-Boc Reaction of the Compound 5

210 mg of the compound 5 was dissolved in 7 mL of DCM, and under ice cooling, added with 3 mL of 4 M HCl/AcOEt, and stirred for 3.5 hours. After confirming by TLC the disappearance of the reacting materials, it was concentrated under reduced pressure by using an evaporator in water bath at 40° C. The residues were washed with diethyl ether, and as a result, the desired introduction precursor 6 was obtained in an amount of 177 mg (yield of 98%).

$^1$H-NMR signal assignment is given in the following.
$^1$H-NMR (500 MHz, CD$_3$OD) δ1.58 (3H, d), 3.51 (2H, m), 4.03 (1H, q), 4.53 (2H, m), 7.53-7.87 (9H, m).

9-3. Introduction of the Introduction Precursor 6 to CS (Injected with 0.3 Eq.)

716 mg of CS (weight average molecular weight of about 20 kDa) was dissolved in 14 mL of WFI and 14 mL of EtOH and added with 164 mg (0.3 eq., 0.47 mmol) of the introduction precursor 6 and 200 mg (0.3 eq., 0.47 mmol) of DMT-MM followed by stirring overnight. Then, 870 mg of NaCl was added and the solution was added dropwise to 55 mL of 95% EtOH/WFI to form precipitate. The supernatant was discarded and washing with 90% EtOH/WFI and 95% EtOH/WFI was performed 2 times for each. The obtained precipitate was dried overnight under reduced pressure, and as a result, 784 mg of the target product 7 was obtained. As a result of obtaining the introduction ratio by $^1$H-NMR, it was found to be 32%.

<Example 10> Synthesis of CS (F,F)-Flurbiprofen

Synthesis of CS (F,F)-flurbiprofen is shown in Scheme 10.

According to condensation between the compound 1 and flurbiprofen to give the compound 8, the Boc group was removed under an acidic condition for conversion into the introduction precursor 9 as an amine hydrochloride salt. By performing the introduction to CS, the conjugate 10 was obtained.

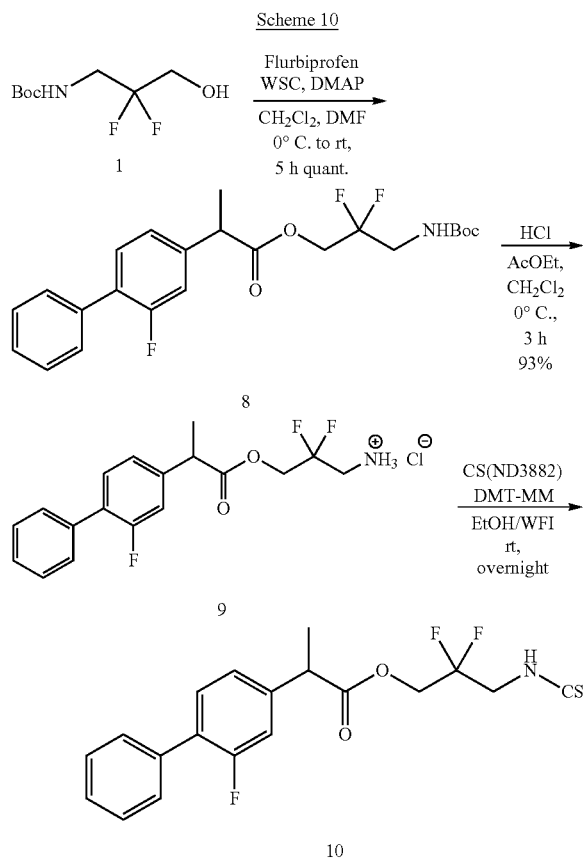

Scheme 10

10-1. Condensation Reaction Between the Compound 1 and Flurbiprofen 100 mg (1.0 eq., 0.47 mmol) of the compound 1 was dissolved in 10 mL of DCM, and added with 122 mg (1.05 eq., 0.50 mmol) of flurbiprofen and 17 mg (0.3 eq., 0.14 mmol) of DMAP. Then, under ice cooling, 182 mg (2.0 eq., 0.95 mmol) of WSC was added followed by stirring overnight at room temperature. After confirming by TLC the disappearance of the reacting materials, the reaction solution was quenched with a saturated aqueous solution of $NH_4Cl$ under ice cooling and liquid fractionation extraction was performed 3 times by using DCM and water. The collected organic layer was washed in order with a saturated aqueous solution of $NH_4Cl$, a saturated aqueous solution of $NaHCO_3$, and a saturated aqueous solution of NaCl. After drying over magnesium sulfate, it was concentrated under reduced pressure by using an evaporator in water bath at 40° C., and the desired compound 8 was obtained in an amount of 211 mg (yield: quant.).

10-2. De-Boc Reaction of the Compound 8

210 mg of the compound 8 was dissolved in 7 mL of DCM, and under ice cooling, added with 3 mL of 4 M HCl/AcOEt, and stirred for 2.5 hours. After confirming by TLC the disappearance of the reacting materials, it was concentrated under reduced pressure by using an evaporator in water bath at 40° C. The residues were washed with diethyl ether, and as a result, the desired introduction precursor 9 was obtained in an amount of 167 mg (yield of 93%).

$^1$H-NMR signal assignment is given in the following.

$^1$H-NMR (500 MHz, $CD_3OD$) δ1.20 (3H, d), 3.51 (2H, m), 3.99 (1H, q), 4.53 (1H, dt), 7.19-7.56 (8H, m).

10-3. Introduction of the Introduction Precursor 9 to CS (Injected with 0.3 Eq.)

596 mg of CS (weight average molecular weight of about 20 kDa) was dissolved in 12 mL of WFI and 12 mL of EtOH and added with 133 mg (0.3 eq., 0.39 mmol) of the introduction precursor 9 and 167 mg (0.3 eq., 0.39 mmol) of DMT-MM followed by stirring overnight. Then, 750 mg of NaCl was added and the solution was added dropwise to 50 mL of 95% EtOH/WFI to form precipitate. The supernatant was discarded and washing with 90% EtOH/WFI and 95% EtOH/WFI was performed 2 times for each. The obtained precipitate was dried overnight under reduced pressure, and as a result, 649 mg of the target product 10 was obtained. As a result of obtaining the introduction ratio by $^1$H-NMR, it was found to be 33%.

<Example 11> Synthesis of CS (H)-Ketoprofen (Hereinbelow, Also Referred to as KP-CS)

Synthesis of CS (H)-ketoprofen is shown in Scheme 11.

By using the aminopropanol 11 as a spacer and protecting the amino group with Boc, it was subjected to condensation with ketoprofen to give the compound 13. Subsequently, the Boc group was removed under an acidic condition for conversion into the introduction precursor 14 as an amine hydrochloride salt. By performing the introduction to CS, the conjugate 15 was obtained.

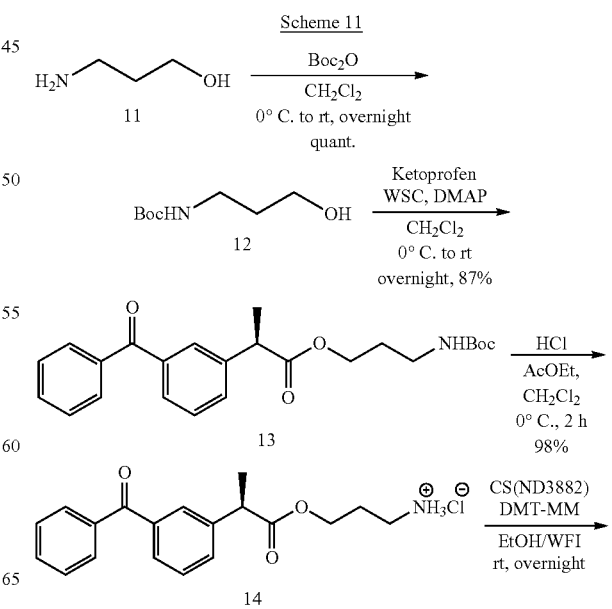

Scheme 11

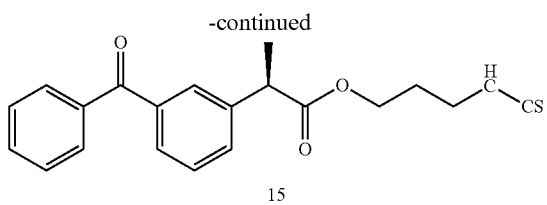

15

11-1. Boc Protection of the Compound 11

5 g (1.0 eq., 66.6 mmol) of the compound 11 was dissolved in 120 mL of DCM, and under ice cooling, it was added with 14.5 g (1.0 eq., 66.6 mmol) of $Boc_2O$. It was then stirred overnight at room temperature. After confirming by TLC the disappearance of the reacting materials, the reaction solution was concentrated under reduced pressure by using an evaporator in water bath at 40° C. As a result, the desired compound 12 was obtained in an amount of 11.7 g (yield: quant.).

$^1$H-NMR signal assignment is given in the following.
$^1$H-NMR (500 MHz, $CDCl_3$) δ1.45 (9H, s), 1.65 (2H, m), 2.94 (1H, br), 3.30 (2H, m), 3.66 (2H, m), 4.76 (1H, br).

11-2. Condensation Reaction Between the Compound 12 and Ketoprofen 1.07 g (1.0 eq., 6.09 mmol) of the compound 12 was dissolved in 12 mL of DCM, and added with 1.55 g (1.0 eq., 6.09 mmol) of ketoprofen and 74 mg (0.1 eq., 0.61 mmol) of DMAP. Then, under ice cooling, 2.34 g (2.0 eq., 12.2 mmol) of WSC was added followed by stirring overnight at room temperature. After confirming by TLC the disappearance of the reacting materials, liquid fractionation extraction was performed 3 times by using ethyl acetate and water. The collected organic layer was washed in order with 5% aqueous solution of citric acid, 5% aqueous solution of $NaHCO_3$, and a saturated aqueous solution of NaCl. After drying over magnesium sulfate, it was concentrated under reduced pressure by using an evaporator in water bath at 40° C., and the desired compound 13 was obtained in an amount of 2.18 g (yield of 87%).

$^1$H-NMR signal assignment is given in the following.
1H-NMR (500 MHz, $CDCl_3$) δ1.45 (9H, s), 1.54 (3H, d), 1.77 (2H, m), 3.11 (2H, m), 3.80 (1H, q), 4.14 (2H, m), 4.69 (1H, br), 7.42-7.83 (9H, m).

11-3. De-Boc Reaction of the Compound 13

2.18 g of the compound 13 was dissolved in 70 mL of DCM, and under ice cooling, added with 30 mL of 4 M HCl/AcOEt, and stirred for 2 hours. After confirming by TLC the disappearance of the reacting materials, it was concentrated under reduced pressure by using an evaporator in water bath at 40° C. The residues were washed with diethyl ether, and as a result, the desired introduction precursor 14 was obtained in an amount of 1.81 g (yield of 98%).

$^1$H-NMR signal assignment is given in the following.
$^1$H-NMR (500 MHz, $CD_3OD$) δ1.53 (3H, d), 1.95 (2H, m), 2.91 (2H, t), 3.91 (1H, q), 4.19 (2H, t), 7.51-7.78 (9H, m).

11-4. Introduction of the Introduction Precursor 14 to CS (Injected with 0.3 Eq.)

2.5 g of CS (weight average molecular weight of about 20 kDa) was dissolved in 50 mL of WFI and 50 mL of EtOH and added with 518 mg (0.3 eq., 1.66 mmol) of the introduction precursor 14 and 699 mg (0.3 eq., 1.66 mmol) of DMT-MM followed by stirring overnight. Then, 2.5 g of NaCl was added and 95% EtOH was added right before cloudiness. The solution was added dropwise to 150 mL of 95% EtOH/WFI to form precipitate. The supernatant was discarded and washing with 90% EtOH/WFI and 95% EtOH/WFI was performed 2 times for each. The obtained precipitate was dried overnight under reduced pressure, and as a result, 2.6 g of the target product 7 was obtained. As a result of obtaining the introduction ratio by $^1$H-NMR, it was found to be 26%.

<Example 12> Synthesis of CS (F)-Ketoprofen (Hereinbelow, Also Referred to as KP-(F)-CS)

Synthesis of CS (F)-ketoprofen is shown in Scheme 12.
According to condensation of the compound 16 with ketoprofen, the compound 17 was obtained. Subsequently, the Boc group was removed under an acidic condition for conversion into the introduction precursor 18 as an amine hydrochloride salt. By performing the introduction to CS, the conjugate 19 was obtained.

Scheme 12

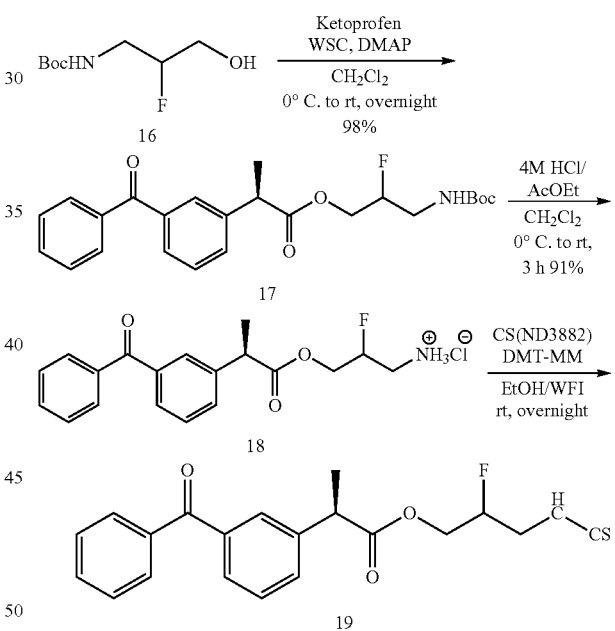

12-1. Condensation Reaction Between the Compound 16 and Ketoprofen 100 mg (1.0 eq., 0.52 mmol) of the compound 16 was dissolved in 5 mL of DCM, and added with 138 mg (1.05 eq., 0.54 mmol) of ketoprofen and 31 mg (0.5 eq., 0.26 mmol) of DMAP. Then, under ice cooling, 199 mg (2.0 eq., 1.04 mmol) of WSC was added followed by stirring overnight at room temperature. After confirming by TLC the disappearance of the reacting materials, the reaction solution was quenched with a saturated aqueous solution of $NH_4Cl$ under ice cooling and liquid fractionation extraction was performed 3 times by using DCM and water. The collected organic layer was washed in order with a saturated aqueous solution of NH₄Cl, a saturated aqueous solution of NaHCO₃, and a saturated aqueous solution of NaCl. After drying over magnesium sulfate, it was concentrated under reduced pressure by using an evaporator in water bath at 40° C., and the desired compound 17 was obtained in an amount of 218 mg (yield of 98%).

¹H-NMR signal assignment is given in the following.
¹H-NMR (500 MHz, CDCl₃) δ6.43 (9H, s), 1.54 (3H, d), 3.25-3.41 (2H, m), 3.85 (1H, q), 4.18-4.33 (2H, m), 4.78 (1H, br), 7.42-7.81 (9H, m).

12-2. De-Boc Reaction of the Compound 17

237 mg of the compound 17 was dissolved in 7 mL of DCM, and under ice cooling, added with 3 mL of 4 M HCl/AcOEt, and stirred for 2 hours and again for 1 hour at room temperature. After confirming by TLC the disappearance of the reacting materials, it was concentrated under reduced pressure by using an evaporator in water bath at 40° C. The residues were washed with diethyl ether, and as a result, the desired introduction precursor 18 was obtained in an amount of 169 mg (yield of 91%).

¹H-NMR signal assignment is given in the following.
¹H-NMR (500 MHz, CD₃OD) δ1.50 (3H, d), 3.10-3.28 (2H, m), 3.96 (1H, q), 4.26-4.47 (2H, m), 4.92 (1H, m), 7.40-7.80 (9H, m).

12-3. Introduction of the Introduction Precursor 18 to CS (Injected with 0.3 Eq.)

760 mg of CS (weight average molecular weight of about 20 kDa) was dissolved in 15 mL of WFI and 15 mL of EtOH and added with 166 mg (0.3 eq., 0.45 mmol) of the introduction precursor 18 and 213 mg (0.3 eq., 0.45 mmol) of DMT-MM followed by stirring overnight. Then, 760 mg of NaCl was added and the solution was added dropwise to 90 mL of 90% EtOH/WFI to form precipitate. The supernatant was discarded and washing with 90% EtOH/WFI and EtOH was performed 2 times for each. The obtained precipitate was dried overnight under reduced pressure, and as a result, 750 mg of the target product 19 was obtained. As a result of obtaining the introduction ratio by ¹H-NMR, it was found to be 30%.

<Example 13> Synthesis of CS (F,F)-Mefenamic Acid

Synthesis of CS (F,F)-mefenamic acid is shown in Scheme 13.

According to condensation of the compound 1 with mefenamic acid, the compound 20 was obtained. Subsequently, the Boc group was removed under an acidic condition for conversion into the introduction precursor 21 as an amine hydrochloride salt. By performing the introduction to CS, the conjugate 22 was obtained.

Scheme 13

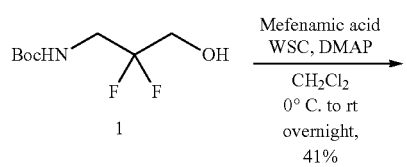

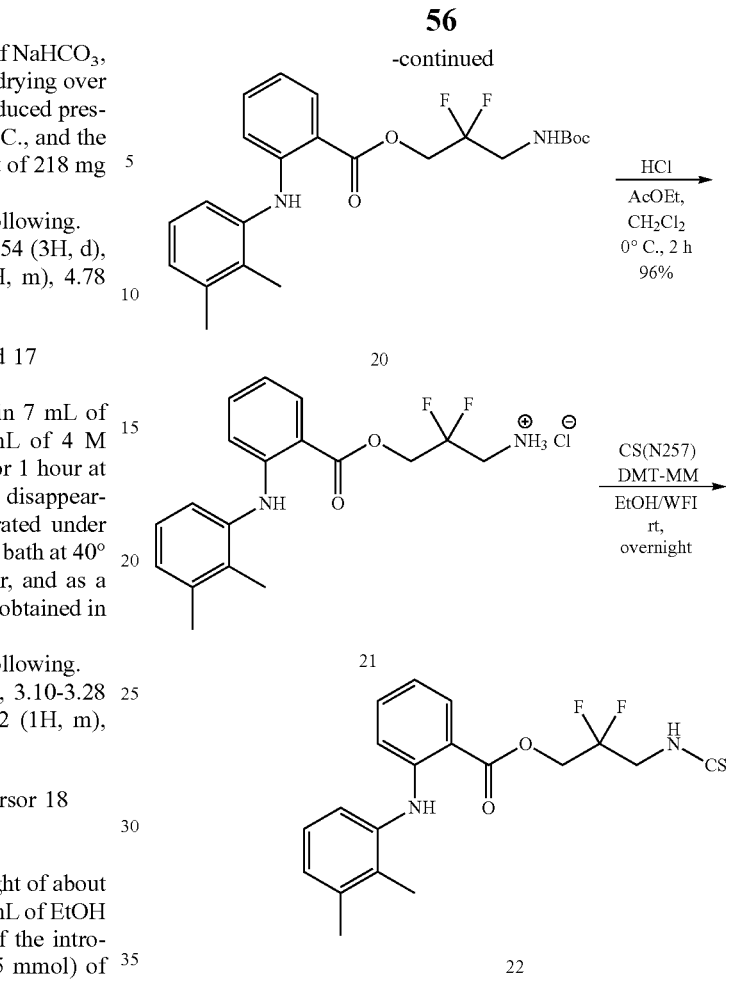

13-1. Condensation Reaction Between the Compound 1 and Mefenamic Acid 302 mg (1.0 eq., 1.43 mmol) of the compound 1 was dissolved in 15 mL of DCM, and added with 346 mg (1.0 eq., 1.43 mmol) of mefenamic acid and 17 mg (0.1 eq., 0.14 mmol) of DMAP. Then, under ice cooling, 550 mg (2.0 eq., 2.87 mmol) of WSC was added followed by stirring overnight at room temperature. After confirming by TLC the disappearance of the reacting materials, liquid fractionation extraction was performed 3 times by using ethyl acetate and water. The collected organic layer was washed in order with 5% aqueous solution of citric acid, 5% aqueous solution of NaHCO₃, and a saturated aqueous solution of NaCl. After drying over magnesium sulfate, the obtained solution was concentrated under reduced pressure by using an evaporator in water bath at 40° C. It was then purified by silica gel column chromatography (toluene:ethyl acetate=15:1) to obtain the desired compound 20 in an amount of 252 mg (yield of 41%).

¹H-NMR signal assignment is given in the following.
¹H-NMR (500 MHz, CDCl₃) δ1.45 (9H, s), 2.16 (3H, s), 2.33 (3H, s), 3.70 (2H, m), 4.55 (2H, t), 4.91 (1H, br), 6.66 (2H, m), 7.03-7.28 (3H, m), 7.97 (1H, d), 9.02 (1H, s).

13-2. De-Boc Reaction of the Compound 20

235 mg of the compound 20 was dissolved in 1 mL of DCM, and under ice cooling, added with 3 mL of 4 M HCl/AcOEt, and stirred for 2.5 hours. After confirming by TLC the disappearance of the reacting materials, it was concentrated under reduced pressure by using an evaporator in water bath at 40° C. The residues were washed with diethyl ether, and as a result, the desired introduction precursor 21 was obtained in an amount of 192 mg (yield of 96%).

$^1$H-NMR signal assignment is given in the following.

$^1$H-NMR (500 MHz, CD$_3$OD) δ2.14 (3H, s), 2.31 (3H, s), 3.57 (2H, t), 4.63 (2H, t), 6.66 (2H, m), 7.08 (3H, m), 7.91 (1H, d), 8.99 (1H,$).

13-3. Introduction of the Introduction Precursor 21 to CS (Injected with 0.3 Eq.)

863 mg of CS (weight average molecular weight of about 20 kDa) was dissolved in 17 mL of WFI and 17 mL of EtOH and added with 191 mg (0.3 eq., 0.52 mmol) of the introduction precursor 21 and 244 mg (0.3 eq., 0.52 mmol) of DMT-MM followed by stirring overnight. Then, 2.6 g of NaCl was added to form rubber-like precipitate, which was then added with 70 mL of EtOH to have complete precipitate. The obtained precipitate was re-solubilized by adding 50 mL of WFI and 10 mL of EtOH. After that, 40 mL of EtOH, 100 mg of NaCl, and 130 mL of EtOH were added in order thereto. Half of the resulting solution was added to 90% EtOH/WFI (85 mL) followed by addition of 100 mL of EtOH and the remaining half of the reaction solution to form precipitate. The supernatant was discarded and washing with 90% EtOH/WFI and EtOH/WFI was performed 2 times for each. The obtained precipitate was dried overnight under reduced pressure, and as a result, 825 mg of the target product 7 was obtained. As a result of obtaining the introduction ratio by $^1$H-NMR, it was found to be 30%.

<Example 14> Synthesis of CS (F,F)-Loxoprofen

Synthesis of CS (F,F)-loxoprofen is shown in Scheme 14.

According to the following order, the loxoprofen 23 was converted to the trans-OH type compound 26, which is an active form, and the CS conjugate 32 was synthesized in the same order as CS (F,F)-flurbiprofen.

Scheme 14

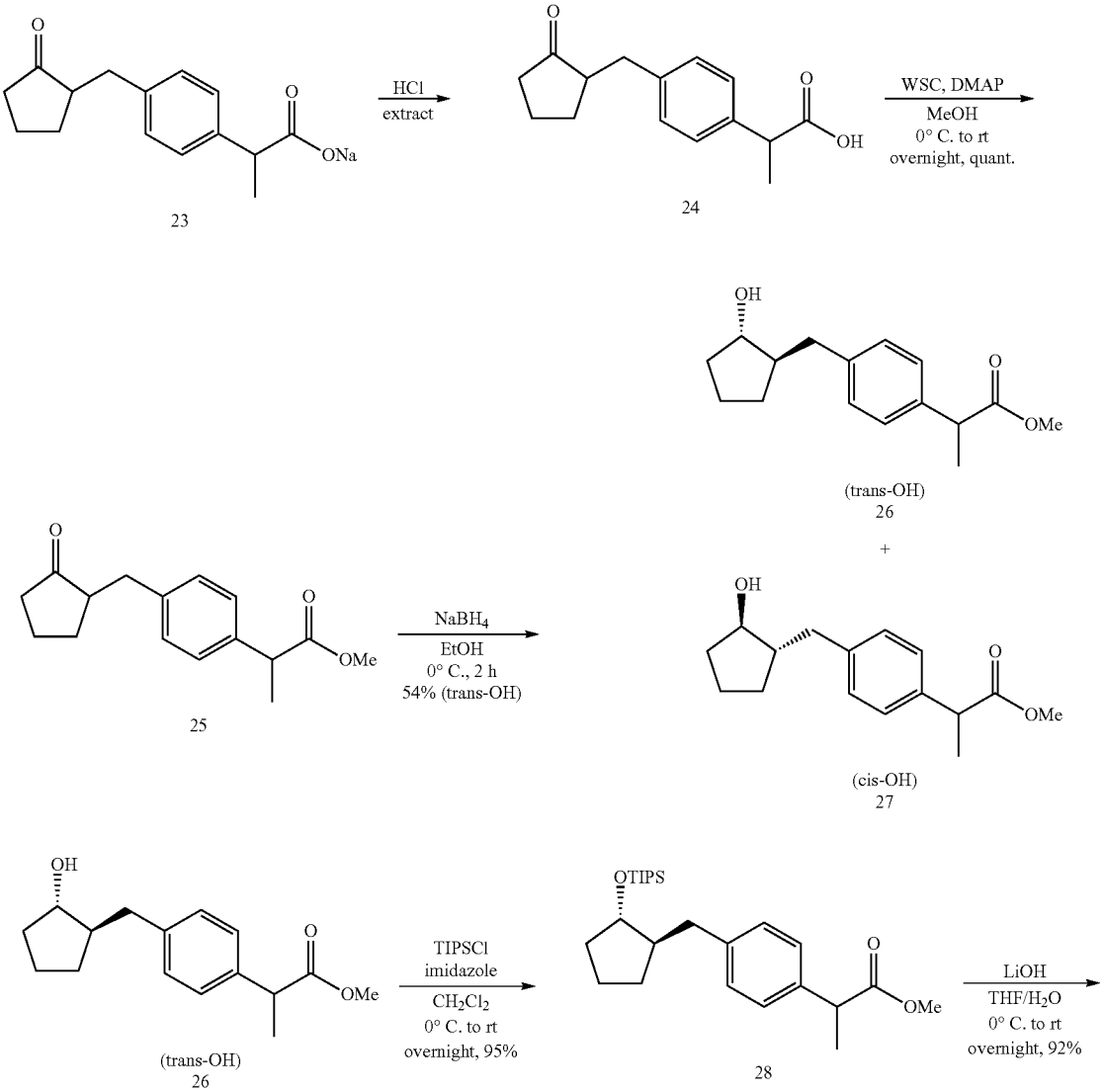

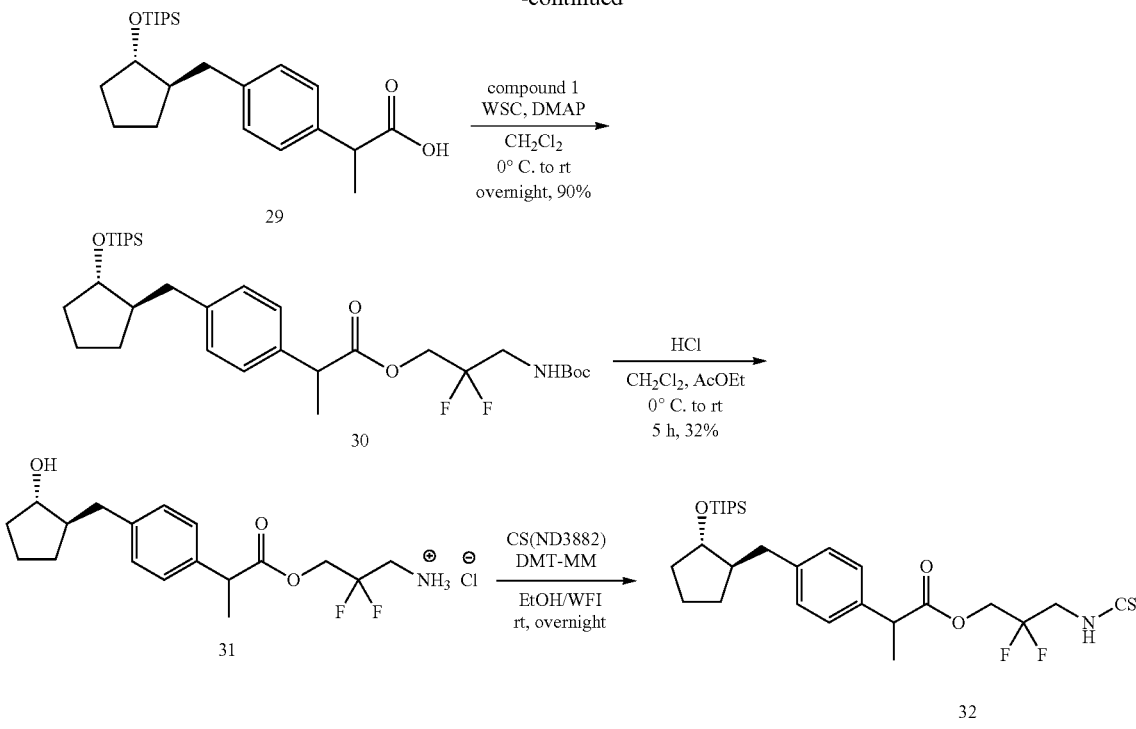

14-1. Conversion of the Compound 23 to the Compound 25

5 g (1.0 eq., 16.4 mmol) of the compound 23 was added with toluene and 1 M HCl and liquid fractionation extraction was performed 3 times. The collected organic layer was washed with a saturated aqueous solution of NaCl. After drying over magnesium sulfate, it was concentrated under reduced pressure by using an evaporator in water bath at 60° C. The obtained compound 24 was directly subjected to the following methyl esterification reaction. Concentrated solution containing the compound 24 was dissolved in 100 mL of MeOH and added with 402 mg (0.2 eq., 3.29 mmol) of DMAP. Then, under ice cooling, it was added with 6.29 g (2.0 eq., 32.9 mmol) of WSC and stirred overnight at room temperature. After confirming by TLC the disappearance of the reacting materials, liquid fractionation extraction was performed 3 times using ethyl acetate and water. The collected organic layer was washed with 5% aqueous solution of citric acid, 5% aqueous solution of NaHCO$_3$, and a saturated aqueous solution of NaCl. After drying over magnesium sulfate, it was concentrated under reduced pressure by using an evaporator in water bath at 40° C. to obtain the desired compound 25 in an amount of 4.27 g (yield: quant.).

$^1$H-NMR signal assignment is given in the following.
$^1$H-NMR (500 MHz, CDCl$_3$) δ1.48 (3H, d), 1.50-1.98 (4H, m), 2.07-2.37 (4H, m), 2.53 (1H, m), 3.66 (3H, s), 3.69 (1H, q), 7.11-7.26 (4H, m).

14-2. Reducing Reaction of the Compound 25

2 g (1.0 eq., 7.71 mmol) of the compound 25 was dissolved in 60 mL of EtOH, and added with 417 mg (3.4 eq., 26.5 mmol) of sodium borohydride followed by stirring for 2 hours. After confirming by TLC the disappearance of the reacting materials, liquid fractionation extraction was performed 3 times by using ethyl acetate and water. The collected organic layer was washed in order with 5% aqueous solution of citric acid, 5% aqueous solution of NaHCO$_3$, and a saturated aqueous solution of NaCl. After drying over magnesium sulfate, it was concentrated under reduced pressure by using an evaporator in water bath at 40° C. to obtain the desired compound 26 in an amount of 1.09 g (yield of 54%).

$^1$H-NMR signal assignment is given in the following.
$^1$H-NMR (500 MHz, DMSO-d$_6$) δ1.14 (1H, m), 1.43 (3H, d), 1.45-1.90 (6H, m), 2.28 (1H, dd), 2.76 (1H, dd), 3.58 (3H, s), 3.65 (1H, m), 3.74 (1H, q), 7.11-7.20 (4H, m).

14-3. Silylation Reaction of the Compound 26

1.09 g (1.0 eq., 4.17 mmol) of the compound 26 was dissolved in 10 mL of DCM and 3 mL of DMF, and under ice cooling, added with 1.78 g (2.2 eq., 12.8 mmol) of triisopropylsilyl chloride and 1.09 g (3.8 eq., 16.0 mmol) of imidazole followed by stirring overnight. After confirming by TLC the disappearance of the reacting materials, the reaction solution was quenched with water under ice cooling and liquid fractionation extraction was performed 3 times by using ethyl acetate and water. The collected organic layer was washed in order with 5% aqueous solution of citric acid, 5% aqueous solution of NaHCO$_3$, and a saturated aqueous solution of NaCl. After drying over magnesium sulfate, it was concentrated under reduced pressure by using an evaporator in water bath at 40° C. It was then purified by silica gel column chromatography (hexane:ethyl acetate=20:1) to obtain the desired compound 28 in an amount of 1.65 g (yield of 95%).

$^1$H-NMR signal assignment is given in the following.
$^1$H-NMR (500 MHz, CDCl$_3$) δ1.00 (21H, m), 1.20 (1H, m), 1.47 (3H, d), 1.51-2.10 (6H, m), 2.29 (1H, dd), 2.78 (1H, dd), 3.65 (3H, s), 3.68 (1H, m), 3.95 (1H, q), 7.11-7.20 (4H, m).

14-4. Hydrolysis Reaction of the Compound 28

1.65 g (1.0 eq., 3.94 mmol) of the compound 27 was dissolved in 45 mL of THF, 15 mL of H$_2$O, and 50 mL of EtOH, and under ice cooling, added with 442 mg (2.6 eq., 10.5 mmol) of lithium hydroxide monohydrate followed by stirring overnight. After confirming by TLC the disappearance of the reacting materials, the reaction solution was quenched with water under ice cooling and liquid fractionation extraction was performed 3 times by using diethyl ether and 1 M HCl. The collected organic layer was washed with a saturated aqueous solution of NaCl. After drying over magnesium sulfate, it was concentrated under reduced pressure by using an evaporator in water bath at 40° C. It was then purified by silica gel column chromatography (chloroform:acetone=3:1) to obtain the desired compound 29 in an amount of 1.47 g (yield of 92%).

$^1$H-NMR signal assignment is given in the following.
$^1$H-NMR (500 MHz, CDCl$_3$) δ1.00 (21H, m), 1.21 (1H, m), 1.49 (3H, d), 1.51-2.10 (6H, m), 2.29 (1H, dd), 2.78 (1H, dd), 3.70 (1H, m), 3.95 (1H, q), 7.11-7.20 (4H, m).

14-5. Condensation Reaction Between the Compound 1 and the Compound 29

306 mg (1.0 Eq., 1.45 Mmol) of the Compound 1 was Dissolved in 6 mL of DCM, and added with 587 mg (1.0 eq., 1.45 mmol) of the compound 28 and 20 mg (0.1 eq., 0.16 mmol) of DMAP. Then, under ice cooling, 576 mg (2.0 eq., 2.90 mmol) of WSC was added followed by stirring overnight at room temperature. After confirming by TLC the disappearance of the reacting materials, liquid fractionation extraction was performed 3 times by using ethyl acetate and water. The collected organic layer was washed in order with 5% aqueous solution of citric acid, 5% aqueous solution of NaHCO$_3$, and a saturated aqueous solution of NaCl. After drying over magnesium sulfate, the obtained solution was concentrated under reduced pressure by using an evaporator in water bath at 40° C. It was then purified by silica gel column chromatography (hexane:ethyl acetate=10:1) to obtain the desired compound 30 in an amount of 781 mg (yield of 90%).

$^1$H-NMR signal assignment is given in the following.
$^1$H-NMR (500 MHz, CDCl$_3$) δ1.00 (21H, m), 1.21 (1H, m), 1.45 (9H, s), 1.51 (3H, d), 1.51-2.10 (6H, m), 2.29 (1H, dd), 2.82 (1H, dd), 3.49 (2H, m), 3.72 (1H, m), 3.95 (1H, q), 4.28 (2H, m), 4.70 (1H, br), 7.11-7.23 (4H, m).

14-6. De-Boc Reaction of the Compound 30

781 mg (1.0 eq., 1.31 mmol) of the compound 30 was dissolved in 2 mL of DCM, and under ice cooling, added with 10 mL of 4 M HCl/AcOEt, and stirred for 5 hours. After confirming by TLC the disappearance of the reacting materials, it was concentrated under reduced pressure by using an evaporator in water bath at 40° C. It was then purified by silica gel column chromatography (chloroform:methanol=1:1) to obtain the desired introduction precursor 31 in an amount of 157 mg (yield of 32%).

$^1$H-NMR signal assignment is given in the following
$^1$H-NMR (500 MHz, CDCl$_3$) δ1.21 (1H, m), 1.51 (3H, d), 1.51-2.12 (6H, m), 2.51 (1H, m), 2.65 (1H, m), 3.07 (2H, m), 3.75 (1H, m), 3.86 (1H, m), 4.20-4.57 (2H, m), 7.11-7.23 (4H, m).

14-7. Introduction of the Introduction Precursor 31 to CS (Injected with 0.3 Eq.)

750 mg of CS (weight average molecular weight of about 20 kDa) was dissolved in 14 mL of WFI and 14 mL of EtOH and added with 156 mg (0.3 eq., 0.41 mmol) of the introduction precursor 31 and 194 mg (0.3 eq., 0.41 mmol) of DMT-MM followed by stirring overnight. Then, 70 mg of NaCl and 13 mL of EtOH were added. Half of the resulting solution was added dropwise to 90% EtOH (24 mL). Subsequently, by addition of 30 mL of EtOH and the remaining half reaction solution, precipitate was formed. The supernatant was discarded and washing with 90% EtOH/WFI and EtOH was performed 2 times for each. The obtained precipitate was dried overnight under reduced pressure, and as a result, 609 mg of the target product 32 was obtained. As a result of obtaining the introduction ratio by $^1$H-NMR, it was found to be 31%.

<Example 15> Preparation of diclofenac(1-amino-2-propanol)-chondroitin sulfate (Hereinbelow, Also Referred to as DF-(Me)-CS)

Preparation of diclofenac-(1-amino-2-propanol)-chondroitin sulfate (i.e., diclofenac-chondroitin sulfate conjugate in which 1-amino-2-propanol is used as a spacer) is shown in Scheme 15.

By using 1-(tert-butoxycarbonyl)amino-2-propanol (1) as a reacting material and brominating the hydroxy group, the compound 2 was obtained. It was then subjected to condensation with sodium diclofenac to give the compound 3. Subsequently, the Boc group was removed under an acidic condition for conversion into the introduction precursor 4 as an amine hydrochloride salt. By performing the introduction to chondroitin sulfate, the conjugate 5 was synthesized.

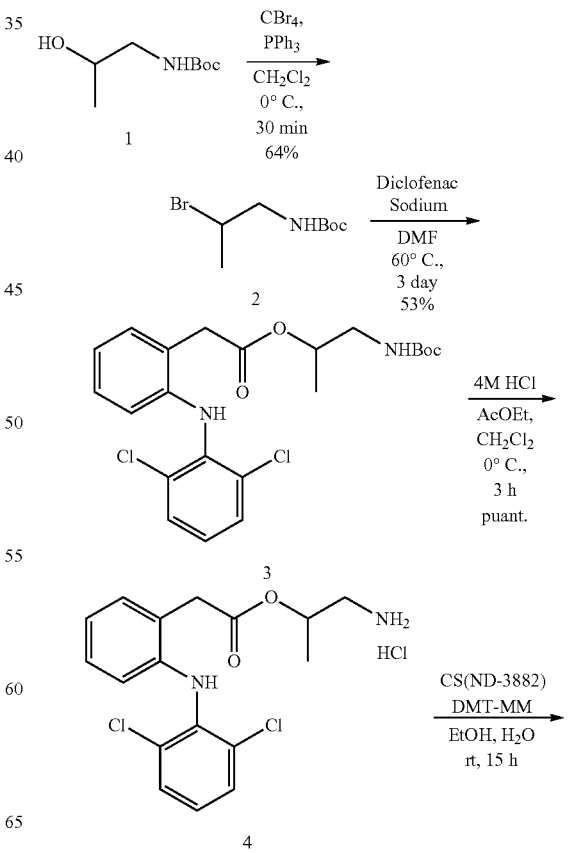

Scheme 15

-continued

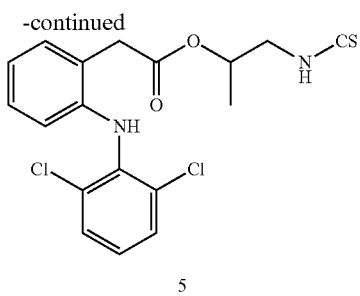

5

15-1. Bromination reaction of 1-(tert-butoxycarbonyl)amino-2-propanol (1)

1000 mg (1.0 eq., 5.71 mmol) of 1-(tert-butoxycarbonyl)amino-2-propanol (1) was dissolved in 10 mL of DCM, and under ice cooling, added with 2852 mg (1.5 eq., 8.60 mmol) of carbon tetrabromide (CBr4) and 2256 mg (1.5 eq., 8.60 mmol) of triphenylphosphine (PPh3) followed by stirring for 30 minutes. After confirming by TLC the disappearance of the reacting materials, ice water was added, stirred for 20 minutes, and liquid fractionation extraction was performed by using ethyl acetate. The organic layer was washed with a saturated aqueous solution of NaCl. After drying over magnesium sulfate, the obtained solution was concentrated under reduced pressure by using an evaporator in water bath at 40° C. The obtained residues were then purified by silica gel column chromatography (hexane:ethyl acetate=10:1) to obtain the compound 2 in an amount of 876 mg (yield of 64%).

$^1$H-NMR signal assignment is given in the following.
$^1$H-NMR (500 MHz, CDCl$_3$) 1.45 (9H, s), 1.68 (3H, d), 3.27-3.33 (1H, m), 3.56 (1H, br), 4.21 (1H, br), 4.96 (1H, br).

15-2. Condensation Reaction Between the Compound 2 and Sodium Diclofenac 876 mg (1.0 eq., 3.68 mmol) of the compound 2 and 1170 mg (1.0 eq., 3.68 mmol) of sodium diclofenac were dissolved in 10 mL of DMF and stirred at 60° C. for three days. Then, liquid fractionation extraction was performed by using ethyl acetate and 5% aqueous solution of sodium bicarbonate. The organic layer was washed with a saturated aqueous solution of NaCl. After drying over magnesium sulfate, the obtained solution was concentrated under reduced pressure by using an evaporator in water bath at 40° C. The obtained residues were then purified by silica gel column chromatography (hexane:ethyl acetate=6:1) to obtain the compound 3 in an amount of 889 mg (yield of 53%).

$^1$H-NMR signal assignment is given in the following.
$^1$H-NMR (500 MHz, CDCl$_3$) 1.25 (3H, d), 1.40 (9H, s), 3.18-3.23 (1H, m), 3.35 (1H, br), 3.79 (1H, d), 3.83 (1H, d), 4.62 (1H, br), 5.02 (1H, br), 6.56 (1H, d), 6.82 (1H, s), 6.94-7.00 (2H, m), 7.12 (1H, t), 7.22 (1H, d), 7.34 (2H, d).

15-3. De-Boc Reaction of the Compound 3

636 mg of the compound 3 was dissolved in 1.5 mL of DCM, and under ice cooling, added with 3 mL of 4 M HCl/AcOEt, and stirred for 3 hours. After confirming by TLC the disappearance of the reacting materials, precipitate was obtained by adding diethyl ether and hexane. Then, the solvent was distilled off under reduced pressure. As a result, the desired introduction precursor 4 was obtained in an amount of 539 mg (yield of 99%).

$^1$H-NMR signal assignment is given in the following
$^1$H-NMR (500 MHz, CDCl3) 1.22 (3H, d), 2.90 (1H, dd), 3.29 (1H, dd), 3.88 (1H, d), 4.01 (1H, d), 5.22 (1H, m), 6.50 (1H, d), 6.71 (1H, s), 6.89-6.97 (2H, m), 7.08 (1H, t), 7.33 (2H, d).

15-4. Introduction of the Introduction Precursor 4 to Chondroitin Sulfate 1500 mg of chondroitin sulfate (weight average molecular weight of about 20 kDa) was dissolved in 24 mL of WFI and 24 mL of EtOH and added with 6 mL of 50% EtOH/WFI solution containing 279 mg (0.24 eq., 0.72 mmol) of the introduction precursor 4 and 6 mL of 50% EtOH/WFI solution containing 338 mg (0.24 eq., 0.72 mmol) of DMT-MM followed by stirring overnight. Then, 0.6 mL of WFI solution containing 150 mg of NaCl was added. By adding 90 mL of 90% EtOH/WFI and 110 mL of EtOH, precipitate was formed. The obtained precipitate was washed in order with 90% EtOH/WFI and EtOH and dried overnight under reduced pressure, and as a result, 1460 mg of the target product 5 was obtained. As a result of obtaining the introduction ratio by $^1$H-NMR, it was found to be 22%.

<Example 16> Preparation of diclofenac(serine ethyl ester)-chondroitin sulfate (Hereinbelow, Also Referred to as DF-(Ser)-CS)

Preparation of diclofenac (serine ethyl ester)-chondroitin sulfate (i.e., diclofenac-chondroitin sulfate conjugate in which serine ethyl ester is used as a spacer) is shown in Scheme 16.
By using Boc-L-serine (1) as a reacting material and performing ethyl esterification of the carboxyl group to have the compound 2, it was then subjected to condensation with sodium diclofenac to give the compound 3. Subsequently, the Boc group was removed under an acidic condition for conversion into the introduction precursor 4 as an amine hydrochloride salt. By performing the introduction to chondroitin sulfate, the conjugate 5 was synthesized.

Scheme 16

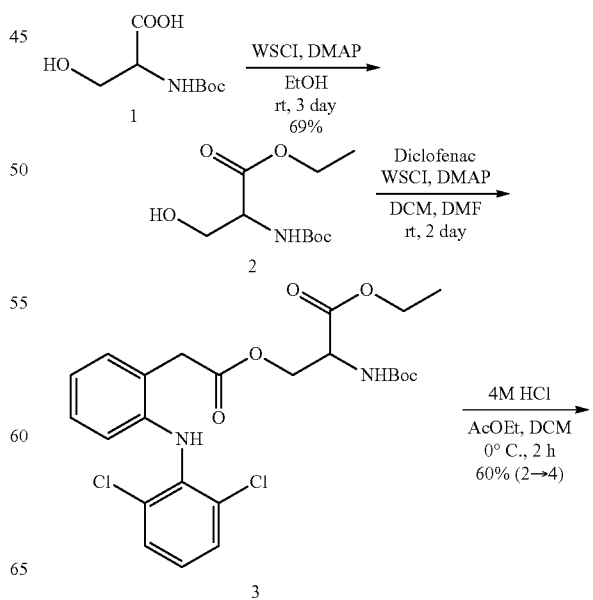

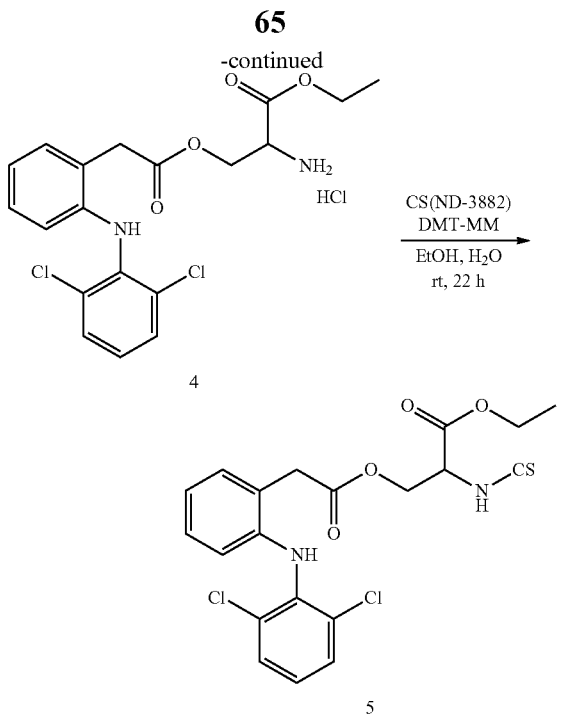

16-1. Ethyl Esterification of Boc-L-Serine (1)

501 mg (1.0 eq., 2.44 mmol) of Boc-L-serine was dissolved in 25 mL of EtOH and, after being added with 941 mg (2.0 eq., 4.91 mmol) of WSC and 34 mg (0.1 eq., 0.28 mmol) of DMAP, it was stirred at room temperature for three days. After concentration of the reaction solution and solubilization in ethyl acetate, liquid fractionation extraction was performed by using 5% aqueous solution of citric acid and 5% aqueous solution of sodium bicarbonate. The organic layer was washed with a saturated aqueous solution of NaCl. After drying over magnesium sulfate, the obtained solution was concentrated under reduced pressure by using an evaporator in water bath at 40° C. As a result, the desired compound 2 was obtained in an amount of 394 mg (yield of 69%).

$^1$H-NMR signal assignment is given in the following.
$^1$H-NMR (500 MHz, CDCl$_3$) δ1.31 (3H, t), 1.46 (9H, s), 3.92-3.97 (2H, m), 4.12 (2H, q), 4.37 (1H, br), 5.42 (1H, br).

16-2. Condensation Reaction Between the Compound 2 and Diclofenac 130 mg (1.0 eq., 0.56 mmol) of the compound 2 and 332 mg (2.0 eq., 1.12 mmol) of diclofenac were dissolved in 5 mL of DCM and 0.5 mL of DMF and, after being added with 15 mg (0.2 eq., 0.12 mmol) of DMAP and 326 mg (3.0 eq., 1.70 mmol) of WSC, it was stirred overnight at room temperature. Furthermore, 165 mg (1.0 eq., 0.56 mmol) of diclofenac and 163 mg (1.5 eq., 0.85 mmol) of WSC were added and stirred overnight at room temperature. The reaction solution was diluted with ethyl acetate, and liquid fractionation extraction was performed by using 5% aqueous solution of citric acid and 5% aqueous solution of sodium bicarbonate. The organic layer was washed with a saturated aqueous solution of NaCl. After drying over magnesium sulfate, the obtained solution was concentrated under reduced pressure by using an evaporator in water bath at 40° C. The obtained residues were then purified by silica gel column chromatography (hexane:ethyl acetate=4:1) to obtain 341 mg of a fraction containing the compound 3.

$^1$H-NMR signal assignment is given in the following.
$^1$H-NMR (500 MHz, CDCl$_3$) δ1.21 (3H, t), 1.46 (9H, s), 3.81 (1H, d), 3.83 (1H, d), 4.11-4.18 (2H, m), 4.40 (1H, dd), 4.52 (1H, dd), 4.58 (1H, bt), 5.29 (1H, br), 6.55 (1H, d), 6.78 (1H, s), 6.94-7.00 (2H, m), 7.12 (1H, t), 7.20 (1H, d), 7.35 (2H, d).

16-3. De-Boc Reaction of the Compound 3

341 mg of the fraction containing the compound 3 was dissolved in 1 mL of DCM, and under ice cooling, added with 3 mL of 4 M HCl/AcOEt, and stirred for 2 hours. After confirming by TLC the disappearance of the reacting materials, precipitate was obtained by adding diethyl ether and hexane. Then, the solvent was distilled off under reduced pressure. As a result, the desired introduction precursor 4 was obtained in an amount of 158 mg (two step yield of the introduction precursor 4:

60% from the compound 2).

$^1$H-NMR signal assignment is given in the following
$^1$H-NMR (500 MHz, CDCl$_3$) δ1.25 (3H, t), 3.86 (1H, d), 3.92 (1H, d), 4.17-4.29 (3H, m), 4.60-4.68 (2H, m), 6.53 (1H, d), 6.96 (1H, t), 7.01 (1H, t), 7.23 (1H, d), 7.36 (2H, d).

16-4. Introduction of the Introduction Precursor 4 to Chondroitin Sulfate 446 mg of chondroitin sulfate (weight average molecular weight of about 20 kDa) was dissolved in 8 mL of WFI and 8 mL of EtOH and added with 2 mL of 50% EtOH/WFI solution containing 95 mg (0.24 eq., 0.21 mmol) of the introduction precursor 4 and 2 mL of 50% EtOH/WFI solution containing 101 mg (0.24 eq., 0.21 mmol) of DMT-MM followed by stirring overnight. Then, 0.2 mL of WFI solution containing 50 mg of NaCl was added. By adding 30 mL of 90% EtOH/WFI and 37 mL of EtOH, precipitate was formed. The obtained precipitate was washed in order with 90% EtOH/WFI and EtOH and dried overnight under reduced pressure, and as a result, 358 mg of the target product 5 was obtained. As a result of obtaining the introduction ratio by $^1$H-NMR, it was found to be 24%.

<Example 17> Preparation of diclofenac(threonine ethyl ester)-chondroitin sulfate (Hereinbelow, Also Referred to as DF-(Thr)-CS)

Preparation of diclofenac (threonine ethyl ester)-chondroitin sulfate (i.e., diclofenac-chondroitin sulfate conjugate in which threonine ethyl ester is used as a spacer) is shown in Scheme 17.

By using Boc-L-threonine (1) as a reacting material and performing ethyl esterification of the carboxyl group to have the compound 2, it was then subjected to condensation with sodium diclofenac to give the compound 3. Subsequently, the Boc group was removed under an acidic condition for conversion into the introduction precursor 4 as an amine hydrochloride salt. By performing the introduction to chondroitin sulfate, the conjugate 5 was synthesized.

67

Scheme 17

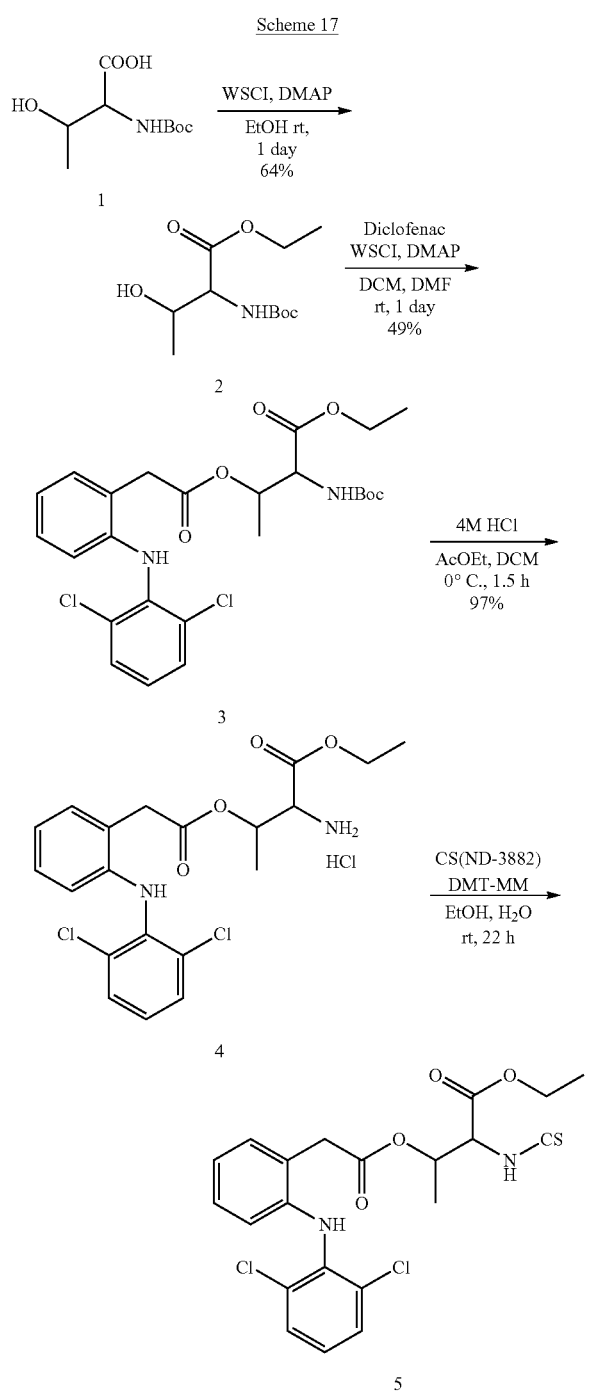

17-1. Ethyl Esterification of Boc-L-Threonine 1

3000 mg (1.0 eq., 13.7 mmol) of Boc-L-threonine was dissolved in 150 mL of EtOH and, after being added with 5274 mg (2.0 eq., 27.5 mmol) of WSC and 166 mg (0.1 eq., 1.36 mmol) of DMAP, it was stirred overnight at room temperature. After concentration of the reaction solution and solubilization in ethyl acetate, liquid fractionation extraction was performed by using 5% aqueous solution of citric acid and 5% aqueous solution of sodium bicarbonate. The organic layer was washed with a saturated aqueous solution

68 of NaCl. After drying over magnesium sulfate, the obtained solution was concentrated under reduced pressure by using an evaporator in water bath at 40° C. As a result, the desired compound 2 was obtained in an amount of 2149 mg (yield of 64%).

$^1$H-NMR signal assignment is given in the following.

$^1$H-NMR (500 MHz, CDCl$_3$) δ1.26 (3H, d), 1.30 (3H, t), 1.46 (9H, s), 1.93 (1H, d), 4.22-4.26 (3H, m), 4.37 (1H, br) 5.28 (1H, br).

17-2. Condensation Reaction Between the Compound 2 and Diclofenac 233 mg (1.0 eq., 0.94 mmol) of the compound 2 and 839 mg (3.0 eq., 2.83 mmol) of diclofenac were dissolved in 9 mL of DCM and 1.5 mL of DMF and, after being added with 36 mg (0.3 eq., 0.29 mmol) of DMAP and 820 mg (4.5 eq., 4.28 mmol) of WSC, it was stirred overnight at room temperature. The reaction solution was diluted with ethyl acetate, and liquid fractionation extraction was performed by using 5% aqueous solution of citric acid and 5% aqueous solution of sodium bicarbonate. The organic layer was washed with a saturated aqueous solution of NaCl. After drying over magnesium sulfate, the obtained solution was concentrated under reduced pressure by using an evaporator in water bath at 40° C. The obtained residues were then purified by silica gel column chromatography (hexane:ethyl acetate=4:1) to obtain the compound 3 in an amount of 242 mg (yield of 49%).

$^1$H-NMR signal assignment is given in the following $^1$H-NMR (500 MHz, CDCl$_3$) δ1.12 (3H, t), 1.34 (3H, d), 1.49 (9H, s), 3.73 (1H, d), 3.79 (1H, d), 3.97-4.04 (2H, m), 4.43 (1H, dd), 5.22 (1H, br), 6.55 (1H, d), 6.80 (1H, s), 6.94-6.98 (2H, m), 7.11 (1H, t), 7.18 (1H, d), 7.34 (2H, d).

17-3. De-Boc Reaction of the Compound 3

242 mg of the compound 3 was dissolved in 0.5 mL of DCM, and under ice cooling, added with 2 mL of 4 M HCl/AcOEt, and stirred for 1.5 hours while slowly increasing the temperature to room temperature. After confirming by TLC the disappearance of the reacting materials, precipitate was obtained by adding diethyl ether and hexane. Then, the solvent was distilled off under reduced pressure. As a result, the desired introduction precursor 4 was obtained in an amount of 206 mg (yield of 97%).

$^1$H-NMR signal assignment is given in the following $^1$H-NMR (500 MHz, CDCl$_3$) δ1.11 (3H, t), 1.65 (3H, d), 3.92 (1H, d), 3.96 (1H, d), 3.98-4.16 (2H, m), 4.17 (1H, s), 5.55-5.60 (1H, m), 6.48 (1H, d), 6.85-6.88 (2H, m), 6.96 (1H, t), 7.06 (1H, d), 7.31-7.32 (3H, m).

17-4. Introduction of the Introduction Precursor 4 to Chondroitin Sulfate 500 mg of chondroitin sulfate (weight average molecular weight of about 20 kDa) was dissolved in 8 mL of WFI and 8 mL of EtOH and added with 2 mL of 50% EtOH/WFI solution containing 111 mg (0.24 eq., 0.24 mmol) of the introduction precursor 4 and 2 mL of 50% EtOH/WFI solution containing 113 mg (0.24 eq., 0.24 mmol) of DMT-MM followed by stirring overnight. Then, 0.2 mL of WFI solution containing 50 mg of NaCl was added. By adding 30 mL of 90% EtOH/WFI and 37 mL of EtOH, precipitate was formed. The obtained precipitate was washed in order with 90% EtOH/WFI and EtOH and dried overnight under reduced pressure, and as a result, 368 mg of the target product 5 was obtained. As a result of obtaining the introduction ratio by ¹H-NMR, it was found to be 24%.

<Example 18> Preparation of diclofenac(1-amino-3,3-dimethylbutan-2-ol)-chondroitin sulfate Preparation of diclofenac (1-amino-3,3-dimethylbutan-2-ol)-chondroitin sulfate (i.e., diclofenac-chondroitin sulfate conjugate in which 1-amino-3,3-dimethylbutan-2-ol is used as a spacer) is shown in Scheme 18.

According to Boc protection of 1-amino-3,3-dimethylbutan-2-ol, the compound 2 was obtained, which was then condensed with diclofenac to obtain the compound 3. Subsequently, the Boc group was removed under an acidic condition for conversion into the introduction precursor 4 as an amine hydrochloride salt. By performing the introduction to chondroitin sulfate, the conjugate 5 was synthesized.

Scheme 18

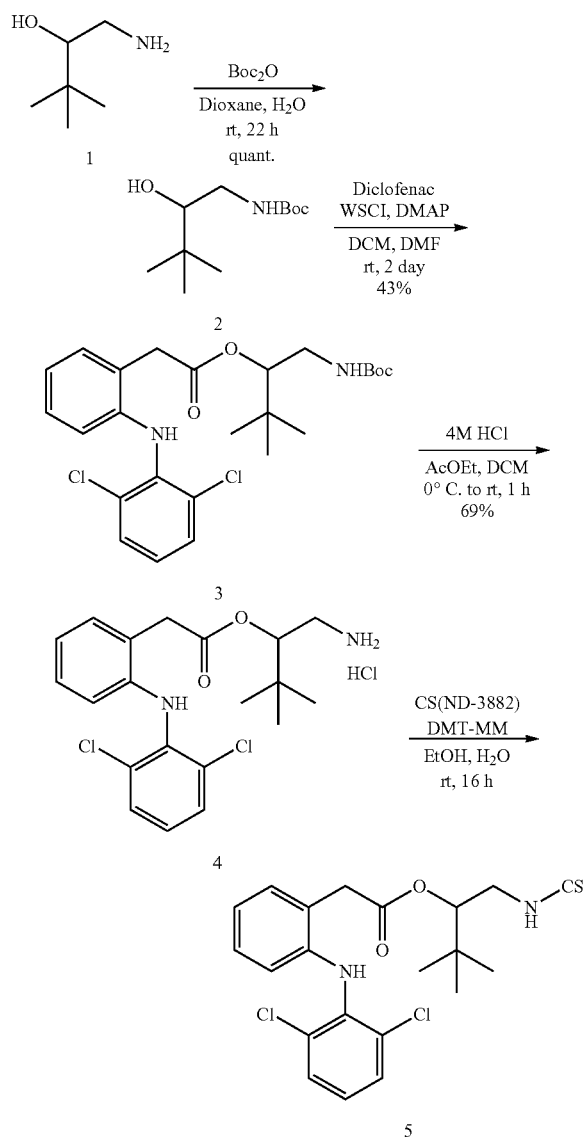

18-1. Boc protection of 1-amino-3,3-dimethylbutan-2-ol 1

2002 mg (1.0 eq., 17.1 mmol) of the 1-amino-3,3-dimethylbutan-2-ol 1 was dissolved in 15 mL of WFI and 10 mL of 1,4-dioxane, after being added with 30 mL of 1,4-dioxane solution containing 3771 mg (1.0 eq., 17.1 mmol) of Boc₂O, it was stirred for 23 hours at room temperature. After confirming by TLC the disappearance of the reacting materials, the reaction solution was concentrated under reduced pressure by using an evaporator in water bath at 40° C. As a result, the desired compound 2 was obtained in an amount of 3663 mg (yield of 99%).

¹H-NMR signal assignment is given in the following.
¹H-NMR (500 MHz, CDCl₃) δ0.93 (9H, s), 1.45 (9H, s), 2.98 (1H, br), 3.31-3.34 (1H, m), 3.38-3.42 (1H, m), 4.88 (1H, br).

18-2. Condensation Reaction Between the Compound 2 and Diclofenac 210 mg (1.0 eq., 0.97 mmol) of the compound 2 and 863 mg (3.0 eq., 2.91 mmol) of diclofenac were dissolved in 9 mL of DCM and 1.5 mL of DMF and, after being added with 39 mg (0.3 eq., 0.32 mmol) of DMAP and 747 mg (4.0 eq., 3.90 mmol) of WSC, it was stirred overnight at room temperature. It was further added with 864 mg (3.0 eq., 2.92 mmol) of diclofenac and 761 mg (4.0 eq., 3.97 mmol) of WSC and stirred overnight at room temperature. The reaction solution was diluted with ethyl acetate, and liquid fractionation extraction was performed by using 5% aqueous solution of citric acid and 5% aqueous solution of sodium bicarbonate. The organic layer was washed with a saturated aqueous solution of NaCl. After drying over magnesium sulfate, the obtained solution was concentrated under reduced pressure by using an evaporator in water bath at 40° C. The obtained residues were then purified by silica gel column chromatography (hexane:ethyl acetate=4:1) to obtain the compound 3 in an amount of 208 mg (yield of 43%).

¹H-NMR signal assignment is given in the following.
¹H-NMR (500 MHz, CDCl₃) δ0.91 (9H, s), 1.35 (9H, s), 3.15-3.21 (1H, m), 3.46-3.50 (1H, m), 3.85 (2H, s), 4.54 (1H, br), 3.81 (1H, d), 6.55 (1H, d), 6.81 (1H, s), 6.94-6.99 (2H, m), 7.11 (1H, t), 7.23 (1H, d), 7.34 (2H, d).

18-3. De-Boc Reaction of the Compound 3

208 mg of the compound 3 was dissolved in 0.5 mL of DCM, and under ice cooling, added with 3 mL of 4 M HCl/AcOEt, and stirred for 1 hour while slowly increasing the temperature to room temperature. After confirming by TLC the disappearance of the reacting materials, precipitate was obtained by adding diethyl ether and hexane. Then, the solvent was distilled off under reduced pressure. As a result, the desired introduction precursor 4 was obtained in an amount of 125 mg (yield of 69%).

¹H-NMR signal assignment is given in the following
¹H-NMR (500 MHz, CDCl₃) δ0.74 (9H, s), 2.82 (1H, t), 3.05 (1H, d), 3.96 (1H, d), 4.10 (1H, d), 5.07 (1H, d), 6.48-6.52 (2H, m), 6.91-6.96 (2H, m), 7.06-7.09 (1H, m), 7.31 (2H, d), 7.39 (1H, d).

18-4. Introduction of the Introduction Precursor 4 to Chondroitin Sulfate 200 mg of chondroitin sulfate (weight average molecular weight of about 20 kDa) was dissolved in 3.2 mL of WFI and 3.2 mL of EtOH and added with 0.8 mL of 50% EtOH/WFI solution containing 41 mg (0.24 eq., 95.7 µmol) of the introduction precursor 4 and 0.8 mL of 50% EtOH/WFI solution containing 45 mg (0.24 eq., 95.7 µmol) of DMT-MM followed by stirring overnight. Then, 80 µL of WFI solution containing 20 mg of NaCl was added. By adding 12 mL of 90% EtOH/WFI and 15 mL of EtOH, precipitate was formed. The obtained precipitate was washed in order with 90% EtOH/WFI and EtOH and dried overnight under reduced pressure, and as a result, 228 mg of the target product 5 was obtained. As a result of obtaining the introduction ratio by $^1$H-NMR, it was found to be 24%.

<Example 19> Preparation of diclofenac(1-amino-2-butanol)-chondroitin sulfate

Preparation of diclofenac (1-amino-2-butanol)-chondroitin sulfate (i.e., diclofenac-chondroitin sulfate conjugate in which 1-amino-2-butanol is used as a spacer) is shown in Scheme 19.

According to Boc protection of 1-amino-2-butanol (1), the compound 2 was obtained, which was then condensed with diclofenac to obtain the compound 3. Subsequently, the Boc group was removed under an acidic condition for conversion into the introduction precursor 4 as an amine hydrochloride salt. By performing the introduction to chondroitin sulfate, the conjugate 5 was synthesized.

Scheme 19

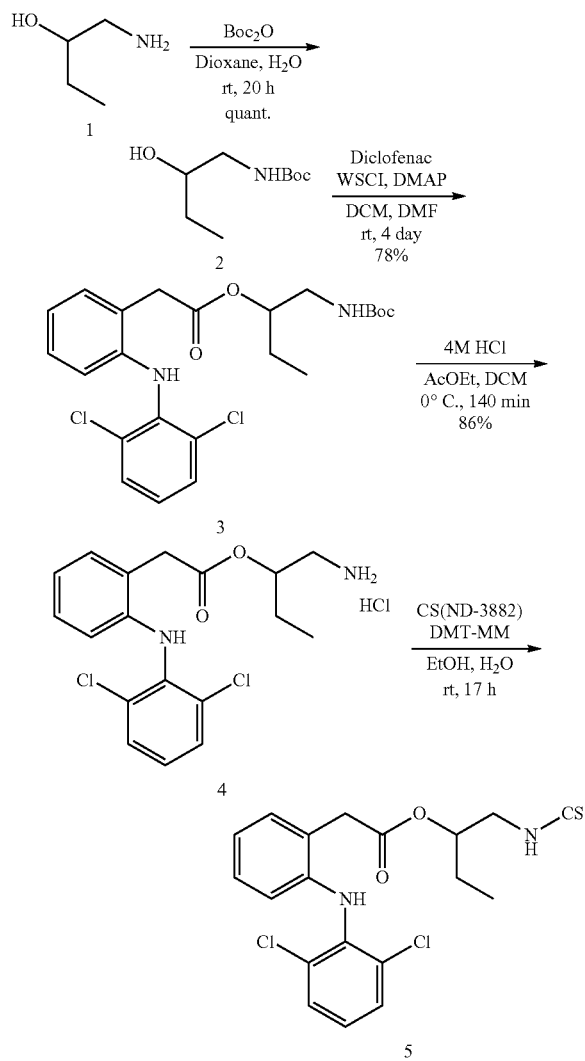

19-1. Boc protection of 1-amino-2-butanol 1

2142 mg (1.0 eq., 24.0 mmol) of the 1-amino-2-butanol (1) was dissolved in 30 mL of WFI and 20 mL of 1,4-dioxane, after being added with 30 mL of 1,4-dioxane solution containing 5244 mg (1.0 eq., 24.0 mmol) of Boc$_2$O, it was stirred for 20 hours at room temperature. After confirming by TLC the disappearance of the reacting materials, the reaction solution was concentrated under reduced pressure by using an evaporator in water bath at 40° C. As a result, the desired compound 2 was obtained in an amount of 4606 mg (yield: quant.).

$^1$H-NMR signal assignment is given in the following.
$^1$H-NMR (500 MHz, CDCl$_3$) δ0.96 (3H, t), 1.42-1.59 (11H, m), 2.99-3.04 (1H, m), 3.30-3.33 (1H, m), 3.70 (1H, br), 4.90 (H, br).

19-2. Condensation Reaction Between the Compound 2 and Diclofenac 330 mg (1.0 eq., 1.74 mmol) of the compound 2 and 1554 mg (3.0 eq., 5.25 mmol) of diclofenac were dissolved in 5 mL of DCM and 1.5 mL of DMF and, after being added with 64 mg (0.3 eq., 0.524 mmol) of DMAP and 1346 mg (4.0 eq., 7.02 mmol) of WSC, it was stirred overnight at room temperature. It was further added with 1552 mg (3.0 eq., 5.24 mmol) of diclofenac and 1327 mg (4.0 eq., 6.92 mmol) of WSC and stirred overnight at room temperature. The reaction solution was diluted with ethyl acetate, and liquid fractionation extraction was performed by using 5% aqueous solution of citric acid and 5% aqueous solution of sodium bicarbonate. The organic layer was washed with a saturated aqueous solution of NaCl. After drying over magnesium sulfate, the obtained solution was concentrated under reduced pressure by using an evaporator in water bath at 40° C. The obtained residues were then purified by silica gel column chromatography (hexane:ethyl acetate=4:1) to obtain the compound 3 in an amount of 633 mg (yield of 78%).

$^1$H-NMR signal assignment is given in the following.
$^1$H-NMR (500 MHz, CDCl$_3$) δ0.88 (3H, t), 1.39 (9H, s), 1.60-1.63 (2H, m), 3.19-3.24 (1H, m), 3.38-3.40 (1H, m), 3.81 (1H, d), 3.85 (1H, d), 4.57 (H, br), 4.88-4.92 (1H, m), 6.56 (1H, d), 6.81 (1H, s), 6.94-7.00 (2H, m), 7.12 (1H, t), 7.24 (1H, d), 7.35 (2H, d).

19-3. De-Boc Reaction of the Compound 3

633 mg of the compound 3 was dissolved in 1 mL of DCM, and under ice cooling, added with 5 mL of 4 M HCl/AcOEt, and stirred for 140 minutes. After confirming by TLC the disappearance of the reacting materials, precipitate was obtained by adding diethyl ether and hexane. Then, the solvent was distilled off under reduced pressure. As a result, the desired introduction precursor 4 was obtained in an amount of 469 mg (yield of 86%).

$^1$H-NMR signal assignment is given in the following.
$^1$H-NMR (500 MHz, CDCl$_3$) δ0.77 (3H, t), 1.39 (9H, s), 2.91 (1H, dd), 3.01 (1H, d), 3.92 (1H, d), 4.02 (1H, d), 5.12 (1H, br), 6.50 (1H, d), 6.67 (1H, s), 6.89-6.97 (2H, m), 7.05-7.09 (1H, m), 7.30-7.33 (3H, m).

19-4. Introduction of the Introduction Precursor 4 to Chondroitin Sulfate 200 mg of chondroitin sulfate (weight average molecular weight of about 20 kDa) was dissolved in 3.2 mL of WFI and 3.2 mL of EtOH and added with 0.8 mL of 50% EtOH/WFI solution containing 39 mg (0.24 eq., 95.6 μmol) of the introduction precursor 4 and 0.8 mL of 50% EtOH/WFI solution containing 45 mg (0.24 eq., 95.5 μmol) of DMT- MM followed by stirring overnight. Then, 80 μL of WFI solution containing 20 mg of NaCl was added. By adding 12 mL of 90% EtOH/WFI and 15 mL of EtOH, precipitate was formed. The obtained precipitate was washed in order with 90% EtOH/WFI and EtOH and dried overnight under reduced pressure, and as a result, 230 mg of the target product 5 was obtained. As a result of obtaining the introduction ratio by ¹H-NMR, it was found to be 24%.

<Example 20> Preparation of diclofenac(2-amino-1-cyclohexylethan-1-ol)-chondroitin sulfate Preparation of diclofenac (2-amino-1-cyclohexylethan-1-ol)-chondroitin sulfate (i.e., diclofenac-chondroitin sulfate conjugate in which 2-amino-1-cyclohexylethan-1-ol is used as a spacer) is shown in Scheme 20.

According to Boc protection of 2-amino-1-cyclohexylethan-1-ol (1), the compound 2 was obtained, which was then condensed with diclofenac to obtain the compound 3. Subsequently, the Boc group was removed under an acidic condition for conversion into the introduction precursor 4 as an amine hydrochloride salt. By performing the introduction to chondroitin sulfate, the conjugate 5 was synthesized.

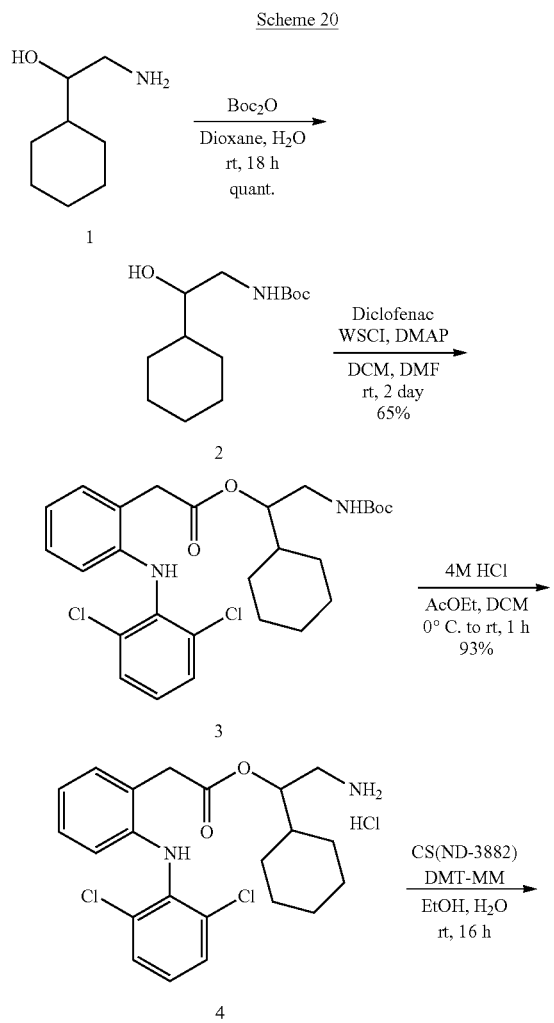

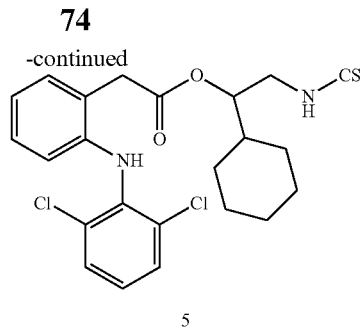

20-1. Boc protection of 2-amino-1-cyclohexylethan-1-ol 1

705 mg (1.0 eq., 4.92 mmol) of the 2-amino-1-cyclohexylethan-1-ol (1) was dissolved in 10 mL of WFI and 15 mL of 1,4-dioxane, after being added with 15 mL of 1,4-dioxane solution containing 1074 mg (1.0 eq., 4.92 mmol) of Boc₂O, it was stirred for 18 hours at room temperature. After confirming by TLC the disappearance of the reacting materials, the reaction solution was concentrated under reduced pressure by using an evaporator in water bath at 40° C. As a result, the desired compound 2 was obtained in an amount of 1189 mg (yield of 99%).

¹H-NMR signal assignment is given in the following.
¹H-NMR (500 MHz, CDCl₃) δ1.19-1.25 (5H, m), 1.36-1.37 (1H, m), 1.45 (9H, s), 1.66-1.68 (2H, m), 1.73-1.78 (2H, m), 1.85 (1H, d), 3.02-3.08 (1H, m), 3.34-3.38 (1H, m), 3.41-3.42 (1H, m), 4.88 (1H, br).

20-2. Condensation Reaction Between the Compound 2 and Diclofenac 291 mg (1.0 eq., 1.20 mmol) of the compound 2 and 1063 mg (3.0 eq., 3.59 mmol) of diclofenac were dissolved in 9 mL of DCM and 1.5 mL of DMF and, after being added with 43 mg (0.3 eq., 0.36 mmol) of DMAP and 921 mg (4.0 eq., 4.81 mmol) of WSC, it was stirred overnight at room temperature. It was further added with 1065 mg (3.0 eq., 3.59 mmol) of diclofenac and 924 mg (4.0 eq., 4.82 mmol) of WSC and stirred overnight at room temperature. The reaction solution was diluted with ethyl acetate, and liquid fractionation extraction was performed by using 5% aqueous solution of citric acid and 5% aqueous solution of sodium bicarbonate. The organic layer was washed with a saturated aqueous solution of NaCl. After drying over magnesium sulfate, the obtained solution was concentrated under reduced pressure by using an evaporator in water bath at 40° C. The obtained residues were then purified by silica gel column chromatography (hexane:ethyl acetate=4:1) to obtain the compound 3 in an amount of 407 mg (yield of 65%).

¹H-NMR signal assignment is given in the following.
¹H-NMR (500 MHz, CDCl₃) 50.96-1.17 (5H, m), 1.38 (9H, s), 1.54-1.69 (6H, m), 3.22-3.27 (1H, m), 3.40-3.43 (1H, m), 3.83 (2H, d), 4.52 (1H, br), 4.80 (1H, t), 6.56 (1H, d), 6.78 (1H, s), 6.94-7.00 (2H, m), 7.12 (1H, t), 7.23 (1H, d), 7.34 (2H, d).

20-3. De-Boc Reaction of the Compound 3

407 mg of the compound 3 was dissolved in 1 mL of DCM, and under ice cooling, added with 4 mL of 4 M HCl/AcOEt, and stirred for 1 hour while gradually increasing the temperature to room temperature. After confirming by TLC the disappearance of the reacting materials, precipitate was obtained by adding diethyl ether and hexane. Then, the solvent was distilled off under reduced pressure. As a result, the desired introduction precursor 4 was obtained in an amount of 125 mg (yield of 93%).

$^1$H-NMR signal assignment is given in the following.

$^1$H-NMR (500 MHz, CDCl$_3$) δ2.93 (1H, t), 3.01 (1H, d), 3.93 (1H, d), 4.03 (1H, d), 5.04 (1H, Br), 6.49 (1H, d), 6.61 (1H, s), 6.90-6.97 (2H, m), 7.06-7.09 (1H, m), 7.31-7.35 (3H, m).

20-4. Introduction of the Introduction Precursor 4 to Chondroitin Sulfate 200 mg of chondroitin sulfate (weight average molecular weight of about 20 kDa) was dissolved in 3.2 mL of WFI and 3.2 mL of EtOH and added with 0.8 mL of 50% EtOH/WFI solution containing 44 mg (0.24 eq., 96.1 μmol) of the introduction precursor 4 and 0.8 mL of 50% EtOH/WFI solution containing 45 mg (0.24 eq., 95.9 μmol) of DMT-MM followed by stirring overnight. Then, 80 μL of WFI solution containing 20 mg of NaCl was added. By adding 12 mL of 90% EtOH/WFI and 15 mL of EtOH, precipitate was formed. The obtained precipitate was washed in order with 90% EtOH/WFI and EtOH and dried overnight under reduced pressure, and as a result, 234 mg of the target product 5 was obtained. As a result of obtaining the introduction ratio by $^1$H-NMR, it was found to be 24%.

<Example 21> Preparation of diclofenac(4-amino-3-hydroxybutyric acid ethyl ester)-chondroitin sulfate Preparation of diclofenac (4-amino-3-hydroxybutyric acid ethyl ester)-chondroitin sulfate (i.e., diclofenac-chondroitin sulfate conjugate in which 4-amino-3-hydroxybutyric acid ethyl ester is used as a spacer) is shown in Scheme 21.

According to ethyl esterification of Boc-4-amino-3-hydroxybutyric acid (1), the compound 2 was obtained, which was then condensed with diclofenac to obtain the compound 3. Subsequently, the Boc group was removed under an acidic condition for conversion into the introduction precursor 4 as an amine hydrochloride salt. By performing the introduction to chondroitin sulfate, the conjugate 5 was synthesized.

Scheme 21

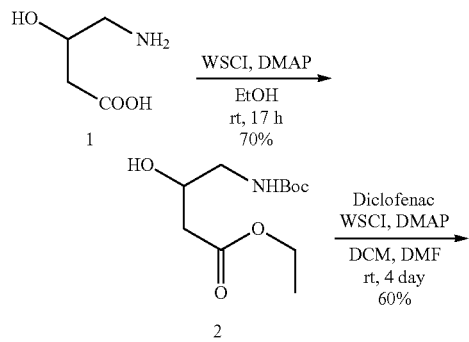

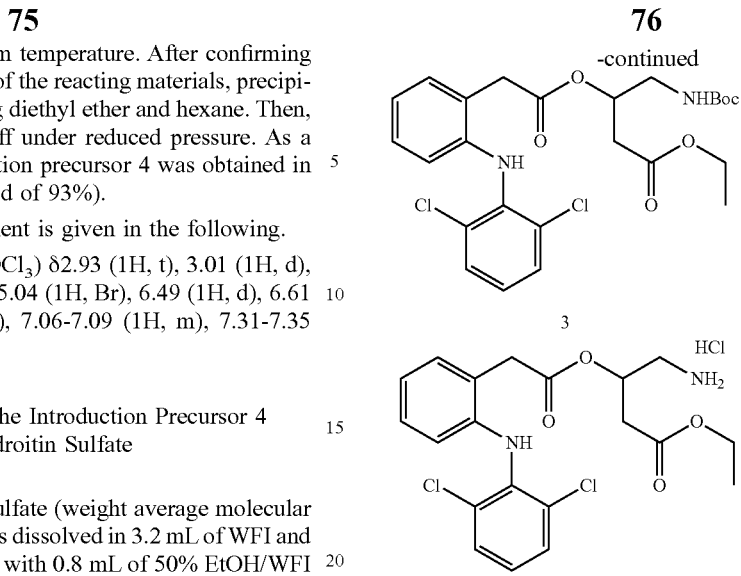

21-1. Ethyl esterification of Boc-4-amino-3-hydroxybutyric acid (1)

503 mg (1.0 eq., 2.29 mmol) of Boc-4-amino-3-hydroxybutyric acid (1) was dissolved in 100 mL of EtOH and, after being added with 880 mg (2.0 eq., 4.59 mmol) of WSC and 28 mg (0.1 eq., 0.23 mmol) of DMAP, it was stirred for 17 hours at room temperature. After concentration of the reaction solution and solubilization in ethyl acetate, liquid fractionation extraction was performed by using 5% aqueous solution of citric acid and 5% aqueous solution of sodium bicarbonate. The organic layer was washed with a saturated aqueous solution of NaCl. After drying over magnesium sulfate, the obtained solution was concentrated under reduced pressure by using an evaporator in water bath at 40° C. The obtained residues were then purified by silica gel column chromatography (hexane:ethyl acetate=1:1) to obtain the desired compound 2 in an amount of 397 mg (yield of 70%).

$^1$H-NMR signal assignment is given in the following.
$^1$H-NMR (500 MHz, CDCl$_3$) δ1.28 (3H, t), 1.45 (9H, s), 2.44-2.53 (2H, m), 3.09-3.15 (1H, m), 3.34 (1H, br), 4.10 (1H, br), 4.18 (2H, dd), 4.95 (1H, br).

21-2. Condensation Reaction Between the Compound 2 and Diclofenac 397 mg (1.0 eq., 1.60 mmol) of the compound 2 and 1425 mg (3.0 eq., 4.81 mmol) of diclofenac were dissolved in 6 mL of DCM and 2.5 mL of DMF and, after being added with 60 mg (0.3 eq., 0.49 mmol) of DMAP and 1227 mg (4.0 eq., 6.40 mmol) of WSC, it was stirred overnight at room temperature. It was further added with 1425 mg (3.0 eq., 4.81 mmol) of diclofenac and 1227 mg (4.0 eq., 6.40 mmol) of WSC and stirred for 3 days, i.e., day and night. The reaction solution was diluted with ethyl acetate, and liquid fractionation extraction was performed by using 5% aqueous solution of citric acid and 5% aqueous solution of sodium bicarbonate. The organic layer was washed with a saturated aqueous solution of NaCl. After drying over magnesium sulfate, the obtained solution was concentrated under reduced pressure by using an evaporator in water bath at 40° C. The obtained residues were then purified by silica gel column chromatography (toluene:acetone=15:1) to obtain the compound 3 in an amount of 503 mg (yield of 60%).

$^{1}$H-NMR signal assignment is given in the following.
$^{1}$H-NMR (500 MHz, CDCl$_3$) δ1.17 (3H, t), 1.40 (9H, s), 2.62-2.65 (2H, m), 3.35-3.41 (2H, m), 3.79 (1H, d), 3.83 (1H, d), 4.02-4.07 (2H, m), 4.64 (1H, br), 5.31-5.34 (1H, m), 6.54 (1H, d), 6.75 (1H, s), 6.93-7.00 (2H, m), 7.12 (1H, t), 7.21 (1H, dd), 7.34 (2H, d).

21-3. De-Boc Reaction of the Compound 3

491 mg of the compound 3 was dissolved in 3 mL of DCM, and under ice cooling, added with 5 mL of 4 M HCl/AcOEt, and stirred for 140 minutes while gradually increasing the temperature to room temperature. After confirming by TLC the disappearance of the reacting materials, precipitate was obtained by adding diethyl ether and hexane. Then, the solvent was distilled off under reduced pressure. As a result, the desired introduction precursor 4 was obtained in an amount of 393 mg (yield of 91%).

$^{1}$H-NMR signal assignment is given in the following.
$^{1}$H-NMR (500 MHz, CDCl$_3$) δ1.11 (3H, t), 2.57 (2H, dt), 3.06 (1H, dd), 3.14 (1H, d), 3.88 (1H, d), 3.93-4.00 (2H, m), 4.02 (1H, d), 4.51 (1H, br), 6.47 (1H, d), 6.58 (1H, s), 6.90 (1H, t), 6.96 (1H, t), 7.06 (1H, t), 7.30-7.32 (3H, m).

21-4. Introduction of the Introduction Precursor 4 to Chondroitin Sulfate 200 mg of chondroitin sulfate (weight average molecular weight of about 20 kDa) was dissolved in 3.2 mL of WFI and 3.2 mL of EtOH and added with 0.8 mL of 50% EtOH/WFI solution containing 38 mg (0.20 eq., 81.2 μmol) of the introduction precursor 4 and 0.8 mL of 50% EtOH/WFI solution containing 45 mg (0.20 eq., 79.7 μmol) of DMT-MM followed by stirring overnight. Then, 100 μL of WFI solution containing 20 mg of NaCl was added. By adding 12 mL of 90% EtOH/WFI and 15 mL of EtOH, precipitate was formed. The obtained precipitate was washed in order with 90% EtOH/WFI and EtOH and dried overnight under reduced pressure, and as a result, 209 mg of the target product 5 was obtained. As a result of obtaining the introduction ratio by $^{1}$H-NMR, it was found to be 20%.

<Example 22> Preparation of diclofenac(1-amino-3,3-dimethylbutan-2-ol)-hyaluronic acid The introduction precursor described in the above 18-3 was introduced to hyaluronic acid.
66 mg of hyaluronic acid was dissolved in 6.55 mL of WFI and 6.55 mL of EtOH, and added with 0.3 mL of 50% EtOH/WFI solution containing 7.1 mg (0.10 eq., 16.3 μmol) of the introduction precursor and 0.3 mL of 50% EtOH/WFI solution containing 7.7 mg (0.10 eq., 16.4 μmol) of DMT-MM followed by stirring overnight. Then, 0.98 mL of 5% aqueous solution of sodium bicarbonate was added. 4 Hours later, neutralization was performed with acetic acid, 0.33 g of NaCl was dissolved, and EtOH was added to form precipitate. The obtained precipitate was washed in order with 90% EtOH/WFI and EtOH and dried overnight under reduced pressure, and as a result, 63 mg of the target product 5 was obtained. As a result of obtaining the introduction ratio by $^{1}$H-NMR, it was found to be 11%.

<Example 23>
Diclofenac(1-amino-2-butanol)-hyaluronic acid

The introduction precursor described in the above 19-3 was introduced to hyaluronic acid.
100 mg of hyaluronic acid (weight average molecular weight of about 900 kDa) was dissolved in 10 mL of WFI and 10 mL of EtOH, and added with 0.5 mL of 50% EtOH/WFI solution containing 10.1 mg (0.10 eq., 25.0 μmol) of the introduction precursor and 0.5 mL of 50% EtOH/WFI solution containing 11.7 mg (0.10 eq., 25.0 μmol) of DMT-MM followed by stirring overnight. Then, 1.5 mL of 5% aqueous solution of sodium bicarbonate was added. 4 Hours later, neutralization was performed with acetic acid, 0.5 g of NaCl was dissolved, and EtOH was added to form precipitate. The obtained precipitate was washed in order with 90% EtOH/WFI and EtOH and dried overnight under reduced pressure, and as a result, 97 mg of the target product 5 was obtained. As a result of obtaining the introduction ratio by $^{1}$H-NMR, it was found to be 12%.

<Example 24> Diclofenac(2-amino-1-cyclohexylethan-1-ol)-hyaluronic acid

The introduction precursor described in the above 20-3 was introduced to hyaluronic acid.
100 mg of hyaluronic acid (weight average molecular weight of about 900 kDa) was dissolved in 10 mL of WFI and 10 mL of EtOH, and added with 0.5 mL of 50% EtOH/WFI solution containing 11.4 mg (0.10 eq., 24.9 μmol) of the introduction precursor and 0.5 mL of 50% EtOH/WFI solution containing 11.7 mg (0.10 eq., 25.0 μmol) of DMT-MM followed by stirring overnight. Then, 1.5 mL of 5% aqueous solution of sodium bicarbonate was added. 4 Hours later, neutralization was performed with acetic acid, 0.5 g of NaCl was dissolved, and EtOH was added to form precipitate. The obtained precipitate was washed in order with 90% EtOH/WFI and EtOH and dried overnight under reduced pressure, and as a result, 98 mg of the target product 5 was obtained. As a result of obtaining the introduction ratio by $^{1}$H-NMR, it was found to be 11%.

<Example 25>
Diclofenac(4-amino-3-hydroxybutyric acid ethyl ester)-hyaluronic acid The introduction precursor described in the above 21-3 was introduced to hyaluronic acid.
200 mg of hyaluronic acid (weight average molecular weight of about 900 kDa) was dissolved in 20 mL of WFI and 20 mL of EtOH, and added with 1 mL of 50% EtOH/WFI solution containing 23.3 mg (0.10 eq., 50.5 μmol) of the introduction precursor and 1 mL of 50% EtOH/WFI solution containing 24.9 mg (0.11 eq., 53.1 μmol) of DMT-MM followed by stirring overnight. Then, 3 mL of 5% aqueous solution of sodium bicarbonate was added. 4 Hours later, neutralization was performed with acetic acid, 1 g of NaCl was dissolved, and EtOH was added to form precipitate. The obtained precipitate was washed in order with 90%

EtOH/WFI and EtOH and dried overnight under reduced pressure, and as a result, 187 mg of the target product 5 was obtained. As a result of obtaining the introduction ratio by $^1$H-NMR, it was found to be 11%.

<Example 26> Diclofenac(1-amino-2-propanol)-hyaluronic acid (Hereinbelow, Also Referred to as DF-(Me)-HA)

The introduction precursor described in the above 15-3 was introduced to hyaluronic acid.

200 mg of hyaluronic acid (weight average molecular weight of about 900 kDa) was dissolved in 20 mL of WFI and 20 mL of EtOH, and added with 1.5 mL of 50% EtOH/WFI solution containing 38.0 mg (0.20 eq., 97.5 µmol) of the introduction precursor and 1.5 mL of 50% EtOH/WFI solution containing 45.4 mg (0.19 eq., 96.7 µmol) of DMT-MM followed by stirring overnight. Then, 3 mL of 5% aqueous solution of sodium bicarbonate was added. 4 Hours later, neutralization was performed with acetic acid, 1 g of NaCl was dissolved, and EtOH was added to form precipitate. The obtained precipitate was washed in order with 90% EtOH/WFI and EtOH and dried overnight under reduced pressure, and as a result, 200 mg of the target product 5 was obtained. As a result of obtaining the introduction ratio by $^1$H-NMR, it was found to be 19%.

<Example 27> Diclofenac(serine ethyl ester)-hyaluronic acid

The introduction precursor described in the above 16-3 was introduced to hyaluronic acid.

200 mg of hyaluronic acid (weight average molecular weight of about 900 kDa) was dissolved in 20 mL of WFI and 20 mL of EtOH, and added with 1.5 mL of 50% EtOH/WFI solution containing 43.4 mg (0.19 eq., 96.9 µmol) of the introduction precursor and 1.5 mL of 50% EtOH/WFI solution containing 45.9 mg (0.20 eq., 97.8 µmol) of DMT-MM followed by stirring overnight. Then, 3 mL of 5% aqueous solution of sodium bicarbonate was added. 4 Hours later, neutralization was performed with acetic acid, 1 g of NaCl was dissolved, and EtOH was added to form precipitate. The obtained precipitate was washed in order with 90% EtOH/WFI and EtOH and dried overnight under reduced pressure, and as a result, 215 mg of the target product 5 was obtained. As a result of obtaining the introduction ratio by $^1$H-NMR, it was found to be 20%.

<Example 28> Diclofenac(threonine ethyl ester)-hyaluronic acid

The introduction precursor described in the above 17-3 was introduced to hyaluronic acid.

200 mg of hyaluronic acid (weight average molecular weight of about 900 kDa) was dissolved in 20 mL of WFI and 20 mL of EtOH, and added with 1.5 mL of 50% EtOH/WFI solution containing 44.7 mg (0.19 eq., 96.8 µmol) of the introduction precursor and 1.5 mL of 50% EtOH/WFI solution containing 45.9 mg (0.20 eq., 97.8 µmol) of DMT-MM followed by stirring overnight. Then, 3 mL of 5% aqueous solution of sodium bicarbonate was added. 4 Hours later, neutralization was performed with acetic acid, 1 g of NaCl was dissolved, and EtOH was added to form precipitate. The obtained precipitate was washed in order with 90% EtOH/WFI and EtOH and dried overnight under reduced pressure, and as a result, 227 mg of the target product 5 was obtained. As a result of obtaining the introduction ratio by $^1$H-NMR, it was found to be 21%.

<Example 29> Preparation of 21-alanyl-betamethasone Introduced Chondroitin Sulfate 29-1. Preparation of 21-Boc-alanyl-betamethasone 0.964 g of Boc-alanine was dissolved in 10 mL of dichloromethane and 15 mL of dimethyl formamide followed by addition of 2 g of betamethasone. After cooling to 0° C., 186.8 mg of N,N-dimethylaminopyridine and 1.27 g of water soluble carbodiimide (WSC) were added followed by stirring overnight at room temperature. After confirming by thin layer chromatography the disappearance of the reacting materials, a saturated aqueous solution of ammonium chloride was added to terminate the reaction. Liquid fractionation extraction was performed by using toluene and water, and the organic layer was washed with a saturated aqueous solution of ammonium chloride, a saturated aqueous solution of sodium hydrogen carbonate, and saturated brine. After drying over anhydrous magnesium sulfate and filtering, the solvent was distilled off under reduced pressure to obtain the desired compound 29-1 (2.72 g, 98%).

29-2. Preparation of 21-alanyl-betamethasone 2.72 g of the compound 29-1 was dissolved in 15 mL of tetrahydrofuran. After cooling to 0° C., 100 mL of 4 M hydrochloric acid/ethyl acetate was added and it was stirred for 3 hours at room temperature. After confirming by thin layer chromatography the disappearance of the reacting materials, the solvent was distilled off under reduced pressure to obtain the compound 29-2 as a desired introduction precursor (1.98 g, 86%).

29-3. Preparation of 21-alanyl-betamethasone Introduced chondroitin sulfate

To 1 g of sodium chondroitin sulfate (weight average molecular weight of about 20 kDa), 15 mL of distilled water was added and stirred for 30 minutes for dissolution. 15 mL of ethanol was slowly added and the solution was homogenously stirred. Thereafter, 185.0 mg of the compound 29-2 was dissolved in 5 mL solution of ethanol/distilled water=1/1 and added thereto. Subsequently, 110.7 mg of 4-(4,6-dimethoxy-1,3,5-triazin-2-yl)-4-methylmorpholinium chloride n-hydrate (DMT-MM) was dissolved in 5 mL of ethanol/distilled water=1/1 solution and added thereto followed by stirring overnight. After adding 1 g of sodium chloride, the reaction solution was added to 200 mL of 90% ethanol/distilled water to form precipitate. After allowing it to stand for a while, the supernatant was removed. Then, 150 mL of 90% ethanol/distilled water was added, stirred and washed for 5 minutes, and allowed again to stand for a while. The same washing was additionally performed two times, and after filtering through a glass filter and drying the obtained precipitate overnight at heating under reduced pressure conditions (40° C., 75 mmHg), the compound 29-3 (0.90 g), which is a desired conjugate, was obtained as a GAG derivative. As a result of measuring $^1$H-NMR, the introduction ratio was found to be 18%.

<Example 30> Preparation of 21-glycyl-betamethasone Introduced Chondroitin Sulfate 30-1. Preparation of 21-Boc-glycyl-betamethasone 1.34 g of Boc-glycine was dissolved in 20 mL of dichloromethane and 20 mL of dimethyl formamide followed by addition of 3 g of betamethasone. After cooling to 0° C., 280.2 mg of N,N-dimethylaminopyridine and 1.91 g of water soluble carbodiimide were added followed by stirring overnight at room temperature. After confirming by thin layer chromatography the disappearance of the reacting materials, a saturated aqueous solution of ammonium chloride was added to terminate the reaction. Liquid fractionation extraction was performed by using toluene and water, and the organic layer was washed with a saturated aqueous solution of ammonium chloride, a saturated aqueous solution of sodium hydrogen carbonate, and saturated brine. After drying over anhydrous magnesium sulfate and filtering, the solvent was distilled off under reduced pressure to obtain the desired compound 30-1 (3.35 g, 82%).

30-2. Preparation of 21-glycyl-betamethasone 3.35 g of the compound 30-1 was dissolved in 20 mL of tetrahydrofuran. After cooling to 0° C., 100 mL of 4 M hydrochloric acid/ethyl acetate was added and it was stirred for 1 hour at room temperature. After confirming by thin layer chromatography the disappearance of the reacting materials, the solvent was distilled off under reduced pressure to obtain the compound 30-2 as a desired introduction precursor (2.69 g, 95%).

30-3. Preparation of 21-glycyl-betamethasone Introduced chondroitin sulfate

To 1 g of sodium chondroitin sulfate (weight average molecular weight of about 20 kDa), 15 mL of distilled water was added and stirred for 30 minutes for dissolution. 15 mL of ethanol was slowly added and the solution was homogenously stirred. Thereafter, 224.3 mg of the compound 30-2 was dissolved in 5 mL solution of ethanol/distilled water=1/1 and added thereto. Subsequently, 110.7 mg of 4-(4,6-dimethoxy-1,3,5-triazin-2-yl)-4-methylmorpholinium chloride n-hydrate was dissolved in 5 mL of ethanol/distilled water=1/1 solution and added thereto followed by stirring overnight. After adding 1 g of sodium chloride, the reaction solution was added to 200 mL of 90% ethanol/distilled water to form precipitate. After allowing it to stand for a while, the supernatant was removed. Then, 150 mL of 90% ethanol/distilled water was added, stirred and washed for 5 minutes, and allowed again to stand for a while. The same washing was additionally performed two times, and after filtering through a glass filter and drying the obtained precipitate overnight at heating under reduced pressure conditions (40° C., 75 mmHg), the compound 30-3 (0.61 g), which is a desired conjugate, was obtained as a GAG derivative. As a result of measuring $^1$H-NMR, the introduction ratio was found to be 20%.

<Example 31> Preparation of 21-isoleucyl-betamethasone Introduced Chondroitin Sulfate 31-1. Preparation of 21-(Boc-isoleucyl)-betamethasone 1.77 g of Boc-isoleucine was dissolved in 20 mL of dichloromethane and 20 mL of dimethyl formamide followed by addition of 3 g of betamethasone. After cooling to 0° C., 280.2 mg of N,N-dimethylaminopyridine and 1.91 g of water soluble carbodiimide were added followed by stirring overnight at room temperature. After confirming by thin layer chromatography the disappearance of the reacting materials, a saturated aqueous solution of ammonium chloride was added to terminate the reaction. Liquid fractionation extraction was performed by using toluene and water, and the organic layer was washed with a saturated aqueous solution of ammonium chloride, a saturated aqueous solution of sodium hydrogen carbonate, and saturated brine. After drying over anhydrous magnesium sulfate and filtering, the solvent was distilled off under reduced pressure to obtain the desired compound 31-1 (3.96 g, 87%).

31-2. Preparation of 21-isoleucyl-betamethasone 3.96 g of the compound 17 was dissolved in 20 mL of tetrahydrofuran. After cooling to 0° C., 100 mL of 4 M hydrochloric acid/ethyl acetate was added and it was stirred for 1 hour at room temperature. After confirming by thin layer chromatography the disappearance of the reacting materials, the solvent was distilled off under reduced pressure to obtain the compound 31-2 as a desired introduction precursor (3.36 g, 99%).

31-3. Preparation of 21-isoleucyl-betamethasone Introduced chondroitin sulfate

To 1 g of sodium chondroitin sulfate (weight average molecular weight of about 20 kDa), 15 mL of distilled water was added and stirred for 30 minutes for dissolution. 15 mL of ethanol was slowly added and the solution was homogenously stirred. Thereafter, 201.9 mg of the compound 31-2 was dissolved in 5 mL solution of ethanol/distilled water=1/1 and added thereto. Subsequently, 110.7 mg of 4-(4,6-dimethoxy-1,3,5-triazin-2-yl)-4-methylmorpholinium chloride n-hydrate was dissolved in 5 mL of ethanol/distilled water=1/1 solution and added thereto followed by stirring overnight. After adding 1 g of sodium chloride, the reaction solution was added to 200 mL of 90% ethanol/distilled water to form precipitate. After allowing it to stand for a while, the supernatant was removed. Then, 150 mL of 90% ethanol/distilled water was added, stirred and washed for 5 minutes, and allowed again to stand for a while. The same washing was additionally performed two times, and after filtering through a glass filter and drying the obtained precipitate overnight at heating under reduced pressure conditions (40° C., 75 mmHg), the compound 31-3 (0.76 g), which is a desired conjugate, was obtained as a polysaccharide derivative. As a result of measuring $^1$H-NMR, the introduction ratio was found to be 15%.

<Example 32> Preparation of diclofenac-(2-aminoethanol)-chondroitin sulfate (Synthesis of DF-CS)

32-1. Preparation of Boc-aminoethyl bromide 2.155 g (10.5 mmol) of 3-bromoethylamine hydrogen bromide salt was dissolved in 20 ml of dichloromethane, and under ice cooling, added with 1.463 ml (10.5 mmol) of triethylamine, further added with 5 ml of dichloromethane solution of Boc$_2$O (2.299 g (10.5 mmol)) followed by stirring. After stirring for 90 minutes at room temperature, ethyl acetate was added, and liquid fractionation washing was performed by using 5% aqueous solution of citric acid, water and saturated brine in order. After dehydrating over sodium sulfate, the solvent was distilled off under reduced pressure. The title compound was obtained in an amount of 2.287 g (97%).

32-2. Synthesis of diclofenac-2-aminoethanol hydrochloride salt

(1) Boc-aminoethanol-diclofenac 5 ml of DMF solution of Boc-aminoethyl bromide (2.287 g (10.2 mmol)) obtained from 32-1 was added with, under ice cooling, 6 ml of DMF solution of sodium diclofenac (3.255 g (10.2 mmol)), and stirred overnight at room temperature. After stirring for 11 hours at 60° C., it was again stirred overnight at room temperature. After adding with ethyl acetate, liquid fractionation washing was performed by using 5% aqueous solution of sodium hydrogen carbonate, water and saturated brine in order. After dehydrating over sodium sulfate, ethyl acetate was distilled off under reduced pressure. The residues were purified by silica gel column chromatography (toluene:ethyl acetate=20:1, 0.5% triethylamine) to obtain the title compound in an amount of 2.675 g (60%).

(2) Diclofenac-2-aminoethanol hydrochloride salt 2.108 g (4.80 mmol) of Boc-aminoethanol-diclofenac which has been obtained from above (1) was dissolved in 5 mL of dichloromethane, and under ice cooling, added with 20 mL of 4 M hydrochloric acid/ethyl acetate followed by stirring for 2.5 hours. By adding diethyl ether and hexane, precipitate was formed. The precipitate was dried under reduced pressure. The title compound was obtained in an amount of 1.775 g (98%).

32-3-1. Preparation of diclofenac-(2-aminoethanol)-chondroitin sulfate (synthesis of DF-CS)

1000 mg of chondroitin sulfate (weight average molecular weight of about 20 kDa) was dissolved in 100 ml of WFI and 100 ml of EtOH. Then, 186 mg (0.25 eq., 0.50 mmol) of diclofenac-2-aminoethanol hydrochloride salt and 232 mg (0.25 eq., 0.50 mmol) of DMT-MM were added followed by stirring overnight. After that, 750 mg of $NaHCO_3$ was added thereto followed by confirming pH 9, the stirring was terminated and it was allowed to stand for 3 hours. Then, 400 µl of acetic acid and 3 g of NaCl were added in order, stirred for 30 minutes, and 200 ml of 90% EtOH/WFI was added to form precipitate. Finally, the supernatant of the suspension was discarded and washing with 90% EtOH/WFI was performed twice. The obtained precipitate was dried overnight under reduced pressure. As a result, 1.08 g of diclofenac-(2-aminoethanol)-chondroitin sulfate (DF-CS) was obtained. As a result of measuring NMR, the introduction ratio was found to be 25%.

32-3-2. Preparation of diclofenac-(2-aminoethanol)-hyaluronic acid (synthesis of DF-HA)

1000 mg of hyaluronic acid (weight average molecular weight of about 900 kDa) was added with 100 ml of WFI followed by stirring for 3 hours for solubilization. Then, 100 ml of EtOH was added and stirred again for 30 minutes. Subsequently, 5 ml of 50% EtOH solution containing 178 mg (0.19 eq., 0.47 mmol) of diclofenac-(2-aminoethanol) hydrochloride salt and 5 ml of 50% EtOH solution of 222 mg (0.19 eq., 0.47 mmol) of DMT-MM were added thereto followed by stirring overnight. After that, 15 ml of aqueous solution of 750 mg $NaHCO_3$ was added and stirred followed by confirming pH 9, the stirring was terminated and it was allowed to stand for 3 hours. Then, 400 µl of acetic acid and 3 g of NaCl were added in order, stirred for 30 minutes, and 465 ml of 90% EtOH/WFI was added to form precipitate. Finally, the supernatant of the suspension was discarded and washing with 90% EtOH/WFI was performed twice and washing with 95% EtOH/WFI and EtOH was performed once for each. The obtained precipitate was dried overnight under reduced pressure. As a result, 1.04 g of diclofenac-(2-aminoethanol)-hyaluronic acid (DF-HA) was obtained. As a result of obtaining the introduction ratio by a carbazole sulfate method, it was found to be 17%.

<Example 33> Synthesis of CS-Fenbufen

Synthesis of CS-fenbufen is shown in the following scheme. By performing condensation of the compound 32 and fenbufen, the compound 33 was obtained.

Then, by removing the protecting group, it was converted to the introduction precursor 34 as an amine hydrochloride salt. According to introduction to CS, the conjugate 35 was obtained.

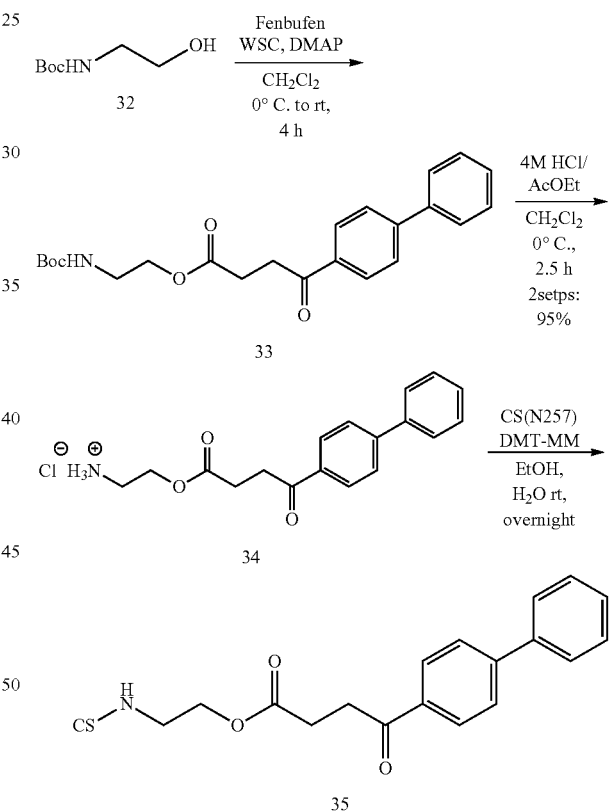

33-1. Condensation Reaction Between the Compound 32 and Fenbufen 653 mg (1.0 eq., 4.01 mmol) of the compound 32 was dissolved in 8 mL of DCM, and added with 1.02 g (1.0 eq., 4.01 mmol) of fenbufen and 98 mg (0.2 eq., 0.80 mmol) of DMAP. After that, under ice cooling, 846 mg (1.1 eq., 4.41 mmol) of WSC was added followed by stirring overnight at room temperature. After confirming an appearance of a new spot by TLC, the reaction solution was quenched, under ice cooling, by using a saturated aqueous solution of NH₄Cl, and liquid fractionation extraction was performed 3 times by using DCM and water. The collected organic layer was washed in order with 5% aqueous solution of citric acid, saturated aqueous solution of NaHCO₃, a saturated aqueous solution of NaCl. After drying over magnesium sulfate, the obtained solution was concentrated under reduced pressure by using an evaporator in water bath at 40° C. to obtain the desired compound 33.

¹H-NMR signal assignment is given in the following.

¹H-NMR (500 MHz, CDCl₃) δ1.45 (9H, s), 2.80 (2H, t), 3.37 (2H, t), 3.41 (2H, m), 4.19 (2H, m), 4.99 (1H, br), 7.38-8.09 (9H, m).

33-2. De-Boc Reaction of the Compound 33

1.5 g of the compound 33 was dissolved in 10 mL of DCM, and under ice cooling, added with 40 mL of 4 M HCl/AcOEt, and stirred for 2.5 hours. After confirming by TLC the disappearance of the reacting materials, it was concentrated under reduced pressure by using an evaporator in water bath at 40° C. As a result of washing the residues with hexane, the desired introduction precursor 34 was obtained in an amount of 1.27 g (two step yield of 95%).

¹H-NMR signal assignment is given in the following.

¹H-NMR (500 MHz, CD₃OD) δ2.84 (2H, t), 3.28 (2H, t), 3.47 (2H, m), 4.37 (2H, m), 7.38-8.09 (9H, m).

33-3. Introduction of the Introduction Precursor 34 to CS 1 g of CS (weight average molecular weight of about 40 kDa) was dissolved in 100 mL of WFI and 100 mL of EtOH and added with 200 mg (0.3 eq., 0.596 mmol) of the introduction precursor 34 and 280 mg (0.3 eq., 0.596 mmol) of DMT-MM followed by stirring overnight. Then, NaHCO₃ solution (750 mg/15 mL) was added followed by stirring for 1 hour. By adding 400 μL of acetic acid, 3 g of NaCl, and 200 mL of 90% EtOH/WFI, precipitate was formed. Subsequently, the supernatant of the suspension was discarded and washing with 90% EtOH/WFI and EtOH was performed two times. The obtained precipitate was dried overnight under reduced pressure, and as a result, 1.07 g of the conjugate 35 was obtained as a target product. As a result of obtaining the introduction ratio by a carbazole sulfate method, it was found to be 17%.

<Example 34> Synthesis of CS-Felbinac

Synthesis of CS-felbinac is shown in the following scheme. By performing condensation of the compound 32 and felbinac, the compound 36 was obtained. Then, by removing the protecting group, it was converted to the introduction precursor 37 as an amine hydrochloride salt. According to introduction to CS, the conjugate 38 was obtained.

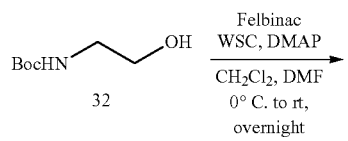

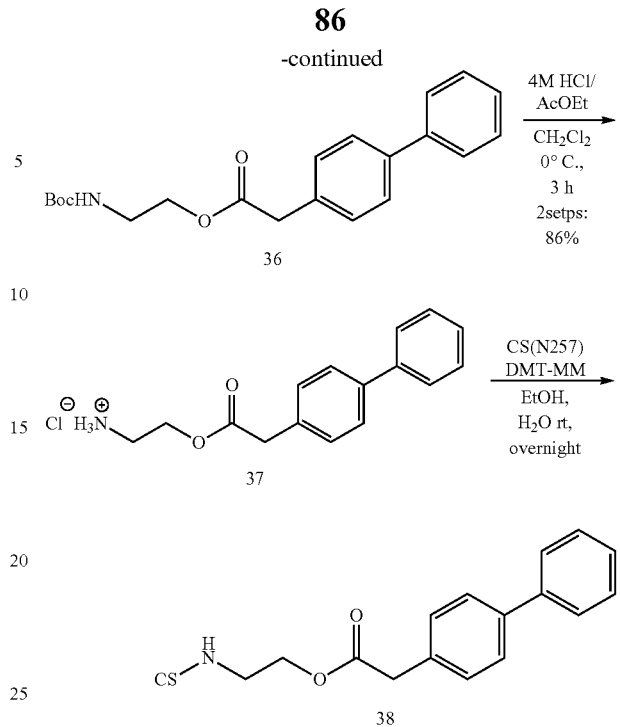

34-1. Condensation Reaction Between the Compound 32 and Felbinac 1 g (1.0 eq., 6.13 mmol) of the compound 32 was dissolved in 15 mL of DCM and 10 mL of DMF, and added with 1.3 g (1.0 eq., 6.13 mmol) of felbinac and 225 mg (0.3 eq., 1.84 mmol) of DMAP. After that, under ice cooling, 1.29 g (1.1 eq., 6.75 mmol) of WSC was added followed by stirring overnight at room temperature. After confirming an appearance of a new spot by TLC, the reaction solution was quenched, under ice cooling, by using a saturated aqueous solution of NH₄Cl, and liquid fractionation extraction was performed 3 times by using DCM and water. The collected organic layer was washed in order with 1 M hydrochloric acid, a saturated aqueous solution of NaHCO₃, a saturated aqueous solution of NaCl. After drying over magnesium sulfate, the obtained solution was concentrated under reduced pressure by using an evaporator in water bath at 40° C. to obtain the desired compound 36 in an amount of 2.2 g (yield of 98%).

¹H-NMR signal assignment is given in the following.

¹H-NMR (500 MHz, CDCl₃) δ1.45 (9H, s), 3.39 (2H, t), 3.69 (2H, s), 4.18 (2H, t), 4.70 (1H, br), 7.33-7.59 (9H, m).

34-2. De-Boc Reaction of the Compound 36

2 g of the compound 36 was dissolved in 7 mL of DCM, and under ice cooling, added with 17 mL of 4 M HCl/AcOEt, and stirred for 3 hours. After confirming by TLC the disappearance of the reacting materials, it was concentrated under reduced pressure by using an evaporator in water bath at 40° C. As a result of washing the residues with hexane, the desired introduction precursor 37 was obtained in an amount of 1.45 g (yield of 88%).

¹H-NMR signal assignment is given in the following.

¹H-NMR (500 MHz, CD₃OD) δ3.28 (2H, t), 3.81 (2H, s), 4.38 (2H, t), 7.33-7.64 (9H, m)

34-3. Introduction of the Introduction Precursor 37 to CS 1 g of CS (weight average molecular weight of about 40 kDa) was dissolved in 100 mL of WFI and 100 mL of EtOH and added with 174 mg (0.3 eq., 0.596 mmol) of the introduction precursor 37 and 280 mg (0.3 eq., 0.596 mmol) of DMT-MM followed by stirring overnight. Then, $NaHCO_3$ solution (750 mg/15 mL) was added followed by stirring for 1 hour. By adding in order 400 μL of acetic acid, 3 g of NaCl, and 200 mL of 90% EtOH/WFI, precipitate was formed. Subsequently, the supernatant of the suspension was discarded and washing with 90% EtOH/WFI and EtOH was performed two times. The obtained precipitate was dried overnight under reduced pressure, and as a result, 1.08 g of the conjugate 38 was obtained as a target product. As a result of obtaining the introduction ratio by a carbazole sulfate method, it was found to be 15%.

<Example 35> Preparation of bezafibrate(aminoethanol)-chondroitin sulfate Preparation of bezafibrate (aminoethanol)-chondroitin sulfate (i.e., bezafibrate-chondroitin sulfate conjugate in which aminoethanol is used as a spacer) is shown in the following scheme. According to condensation of Boc-aminoethanol with bezafibrate followed by removal of the Boc group under an acidic condition, conversion into the introduction precursor 4 as an amine hydrochloride salt was achieved. By performing the introduction to chondroitin sulfate, the conjugate 5 was synthesized.

35-1. Condensation Between Boc-Aminoethanol and Bezafibrate 174 mg (1.0 eq., 0.93 mmol) of the compound 2 and 336 mg (1.0 eq., 0.93 mmol) of bezafibrate were dissolved in 1.5 mL of DCM and 1.5 mL of DMF, and added with a solution in which 11 mg (0.1 eq., 0.09 mmol) of DMAP and 275 mg (1.5 eq., 1.43 mmol) of WSC are dissolved in 1.5 mL of DCM followed by stirring overnight at room temperature. Furthermore, by adding a solution in which 335 mg (1.0 eq., 0.93 mmol) of bezafibrate and 285 mg (1.5 eq., 1.49 mmol) of WSC are dissolved in 1.0 mL of DCM followed by stirring overnight at room temperature. The reaction solution was diluted with ethyl acetate and liquid fractionation extraction was performed by using 5% aqueous solution of citric acid and 5% aqueous solution of sodium bicarbonate. The organic layer was washed with a saturated aqueous solution of NaCl. After drying over magnesium sulfate, the obtained solution was concentrated under reduced pressure by using an evaporator in water bath at 40° C. The obtained residues were purified by silica gel column chromatography (hexane:ethyl acetate=1:1) to obtain the compound 3 in an amount of 477 mg (yield of 88%).

$^1$H-NMR signal assignment is given in the following.

$^1$H-NMR (500 MHz, $CDCl_3$) δ1.40 (9H, s), 1.62 (6H,$), 2.87 (2H, t), 3.27 (2H, br), 3.66 (2H, br), 4.20 (2H, br), 4.41 (1H, br), 6.13 (1H, br), 6.80 (2H, br), 7.09 (2H, br), 7.37 (2H, br), 7.62 (2H, br).

35-2. De-Boc Reaction of the Compound 3

477 mg of the compound 3 was dissolved in 1 mL of DCM, and under ice cooling, added with 4 mL of 4 M

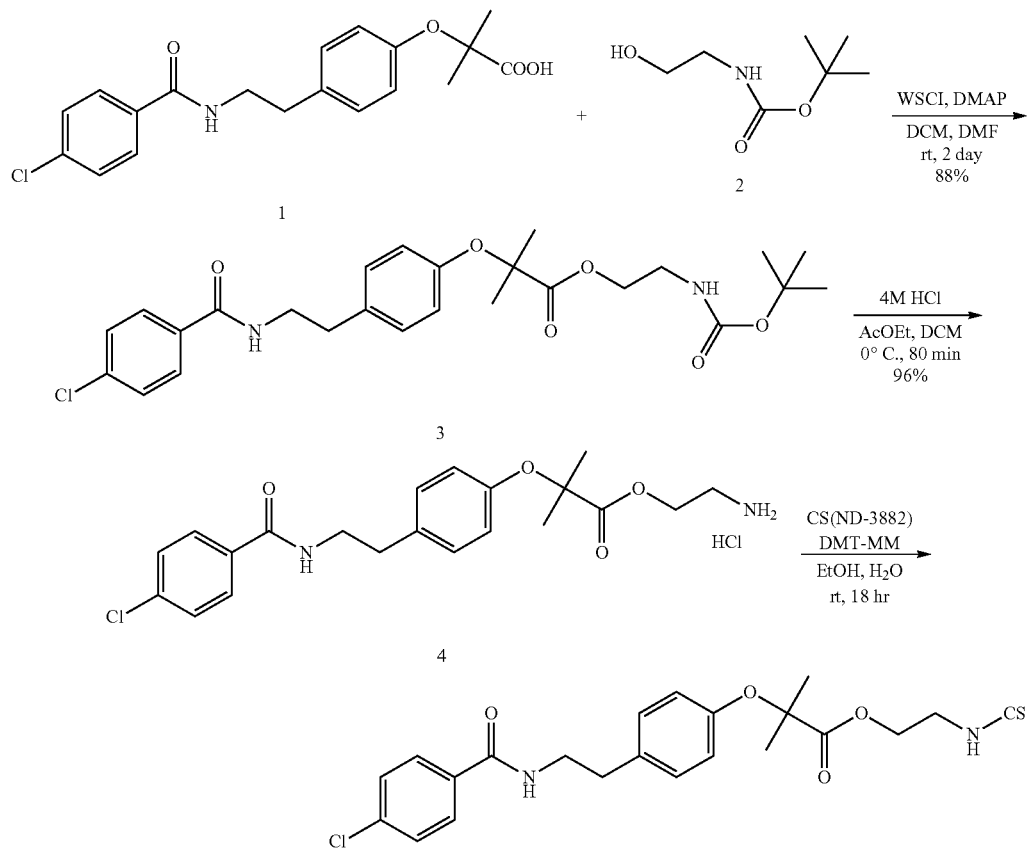

HCl/AcOEt, and stirred for 80 minutes. After confirming by TLC the disappearance of the reacting materials, precipitate was obtained by adding diethyl ether. As a result of washing the residues with diethyl ether, the desired introduction precursor 4 was obtained in an amount of 401 mg (yield of 96%).

$^1$H-NMR signal assignment is given in the following.

$^1$H-NMR (500 MHz, CD$_3$OD) δ1.58 (6H, s), 2.85 (2H, t), 3.20 (2H, t), 3.55 (2H, t), 4.34 (2H, t), 6.82 (2H, dd), 7.17 (2H, dd), 7.46 (2H, dd), 7.74 (2H, dd).

35-3. Introduction of the Introduction Precursor 4 to Chondroitin Sulfate 200 mg of chondroitin sulfate (weight average molecular weight of about 20 kDa) was dissolved in 3.2 mL of WFI and added with a solution in which 35 mg (0.20 eq., 79.8 μmol) of the introduction precursor 4 and 39 mg (0.20 eq., 82.1 μmol) of DMT-MM are dissolved in 4.0 mL of EtOH and 0.8 mL of WFI followed by stirring for 18 hours. Then, 100 μL of 20% NaCl solution was added followed by addition of 12 mL of 90% EtOH/WFI and 15 mL of EtOH to form precipitate. The obtained precipitate was washed in order with 90% EtOH/WFI and EtOH and dried overnight under reduced pressure, and as a result, 208 mg of the target product 5 (compound 35-1) was obtained. As a result of measuring $^1$H-NMR, the introduction ratio was found to be 22%.

35-4. Preparation of bezafibrate(aminoethanol)-hyaluronic acid

The introduction precursor 4 described in Examples 35 was introduced to hyaluronic acid.

200 mg of hyaluronic acid (weight average molecular weight of about 900 kDa) was dissolved in 20 mL of WFI and 20 mL of EtOH and added with 1 mL 50% EtOH/WFI solution containing the introduction precursor (22.1 mg (0.10 eq., 50.1 μmol) and 1 mL 50% EtOH/WFI solution containing DMT-MM (24.8 mg (0.10 eq., 52.9 μmol)) followed by stirring overnight. After that, 3 mL of 5% aqueous solution of sodium bicarbonate was added. 4 Hours later, it was neutralized with acetic acid. By dissolving 1 g of NaCl and adding EtOH thereto, precipitate was formed. The obtained precipitate was washed in order with 90% EtOH/WFI and EtOH and dried overnight under reduced pressure, and as a result, 190 mg of the target product 5 (compound 35-2) was obtained. As a result of measuring $^1$H-NMR, the introduction ratio was found to be 13%.

<Example 36> Preparation of bezafibrate(2-amino-1-cyclohexylethan-1-ol)-chondroitin sulfate Preparation of bezafibrate (2-amino-1-cyclohexylethan-1-ol)-chondroitin sulfate (i.e., bezafibrate-chondroitin sulfate conjugate in which 2-amino-1-cyclohexylethan-1-ol is used as a spacer) is shown in the following scheme. According to condensation of bocylated product of 2-amino-1-cyclohexylethan-1-ol with bezafibrate followed by removal of the Boc group under an acidic condition, conversion into the introduction precursor 4 as an amine hydrochloride salt was achieved. By performing the introduction to chondroitin sulfate, the conjugate 5 was synthesized.

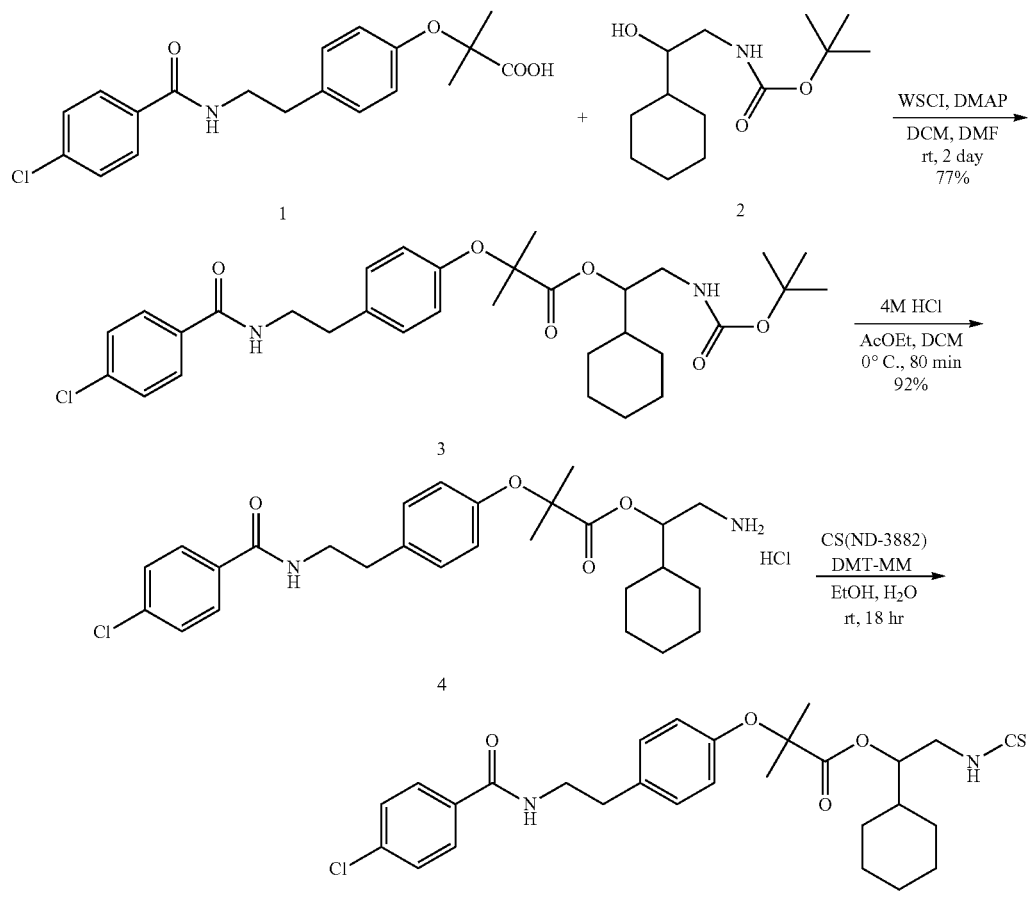

36-1. Condensation Between Bocylated Product of 2-amino-1-cyclohexylethan-1-ol and bezafibrate 201 mg (1.0 eq., 0.83 mmol) of the compound 2 and 300 mg (1.0 eq., 0.83 mmol) of bezafibrate were dissolved in 1.5 mL of DCM and 1.5 mL of DMF, and added with a solution in which 10 mg (0.1 eq., 0.08 mmol) of DMAP and 244 mg (1.5 eq., 1.27 mmol) of WSC are dissolved in 1.5 mL of DCM followed stirring overnight at room temperature. Furthermore, after adding a solution in which 301 mg (1.0 eq., 0.83 mmol) of bezafibrate and 245 mg (1.5 eq., 1.28 mmol) of WSC are dissolved in 1.0 mL of DCM, it was stirred overnight at room temperature. The reaction solution was diluted with ethyl acetate and liquid fractionation extraction was performed by using 5% aqueous solution of citric acid and 5% aqueous solution of sodium bicarbonate. The organic layer was washed with a saturated aqueous solution of NaCl. After drying over magnesium sulfate, the obtained solution was concentrated under reduced pressure by using an evaporator in water bath at 40° C. The obtained residues were purified by silica gel column chromatography (toluene:ethyl acetate=3:1) to obtain the compound 3 in an amount of 375 mg (yield of 77%).

$^1$H-NMR signal assignment is given in the following.
$^1$H-NMR (500 MHz, CDCl$_3$) δ0.94-1.17 (5H, m), 1.41 (9H, br), 2.86 (2H, br), 3.13-3.19 (3H, m), 3.63-3.68 (2H, m), 4.32 (1H,$), 4.79 (1H, m), 6.15 (1H,$), 6.78-6.83 (2H, m), 7.09 (2H, d), 7.37 (2H, d), 7.62-7.77 (2H, m)

36-2. De-Boc Reaction of the Compound 3

375 mg of the compound 3 was dissolved in 1 mL of DCM, and under ice cooling, added with 4 mL of 4 M HCl/AcOEt, and stirred for 80 minutes. After confirming by TLC the disappearance of the reacting materials, precipitate was obtained by adding diethyl ether. As a result of washing the residues with diethyl ether, the desired introduction precursor 4 was obtained in an amount of 309 mg (yield of 92%).

$^1$H-NMR signal assignment is given in the following.
$^1$H-NMR (500 MHz, CD$_3$OD) δ0.97-1.03 (6H, m), 1.61-1.71 (6H, m), 2.85 (2H, t), 3.10 (2H, m), 3.48-3.58 (3H, m), 4.83-4.91 (1H, m), 6.84 (2H, d), 7.17 (2H, d), 7.46 (2H, dd), 7.75 (2H, dd)

36-3. Introduction of the Introduction Precursor 4 to Chondroitin Sulfate 200 mg of chondroitin sulfate (weight average molecular weight of about 20 kDa) was dissolved in 3.2 mL of WFI and added with a solution in which 42 mg (0.20 eq., 79.7 µmol) of the introduction precursor 4 and 38 mg (0.20 eq., 81.0 µmol) of DMT-MM are dissolved in 4.0 mL of EtOH and 0.8 mL of WFI followed by stirring for 18 hours. Then, 100 µL of 20% NaCl solution was added followed by addition of 12 mL of 90% EtOH/WFI and 15 mL of EtOH to form precipitate. The obtained precipitate was washed in order with 90% EtOH/WFI and EtOH and dried overnight under reduced pressure, and as a result, 215 mg of the target product 5 (compound 36-1) was obtained. As a result of measuring $^1$H-NMR, the introduction ratio was found to be 20%.

36-4. Preparation of bezafibrate(2-amino-1-cyclohexylethan-1-ol)-hyaluronic acid The introduction precursor 4 described in Examples 36 was introduced to hyaluronic acid.

200 mg of hyaluronic acid (weight average molecular weight of about 900 kDa) was dissolved in 20 mL of WFI and 20 mL of EtOH and added with 1 mL of 50% EtOH/WFI solution containing the introduction precursor (26.3 mg (0.10 eq., 50.2 µmol)) and 1 mL of 50% EtOH/WFI solution containing DMT-MM (23.7 mg (0.10 eq., 50.5 µmol)) followed by stirring overnight. After that, 3 mL of 5% aqueous solution of sodium bicarbonate was added. 4 Hours later, it was neutralized with acetic acid. By dissolving 1 g of NaCl and adding EtOH thereto, precipitate was formed. The obtained precipitate was washed in order with 90% EtOH/WFI and EtOH and dried overnight under reduced pressure, and as a result, 192 mg of the target product 5 (compound 36-2) was obtained. As a result of measuring $^1$H-NMR, the introduction ratio was found to be 13%.

<Test Example A1> In Vitro Release Test of Betamethasone (X)-Chondroitin Sulfate (X=F, Cl, Br, H)

According to the following conditions, an in vitro release test (drug release test) was performed with the betamethasone-chondroitin sulfate (conjugate) which has been synthesized Example 1 to Example 4.

(1) By using sodium dihydrogen phosphate dihydrate (NaH$_2$PO$_4$.2H$_2$O) and disodium hydrogen phosphate dodecahydrate (Na$_2$HPO$_4$.12H$_2$O), a solution with pH 5.3, 6.3, 7.0, 7.5, 8.1, or 9.2 was prepared.

(2) Conjugate was dissolved such that each solution prepared in the above (1) is at 0.05%.

(3) After the storage at 36° C. and sampling every day, the peak area ratio of the conjugate and a single compound of betamethasone was determined by HPLC (SEC: size exclusion chromatography).

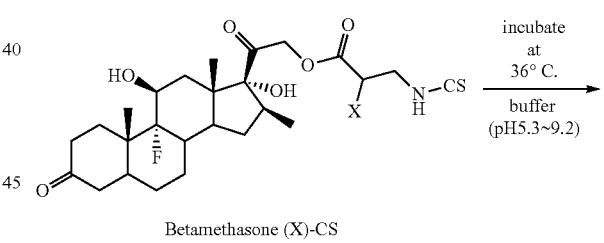

Betamethasone (X)-CS

X = F: Betamethasone(F)-CS
Cl: Betamethasone(Cl)-CS
Br: Betamethasone(Br)-CS
H: Betamethasone-CS

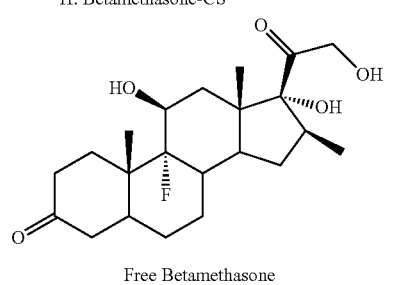

Free Betamethasone

A1-1. Preparation of Solution for Release Test

Each of sodium dihydrogen phosphate dihydrate (NaH$_2$PO$_4$.2H$_2$O) (780 mg (5.0 mmol)) and disodium hydrogen phosphate dodecahydrate (Na$_2$HPO$_4$.12H$_2$O) (1.79 g (5.0 mmol)) was dissolved in WFI (500 mL) to give a NaH$_2$PO$_4$ solution and a Na$_2$HPO$_4$ solution. Those two solutions were admixed with each other at the following ratio and used as release test solutions A to F.

TABLE 3

|  | A | B | C | D | E | F |
| --- | --- | --- | --- | --- | --- | --- |
| NaH$_2$PO$_4$ Solution | 100 mL | 90 mL | 60 mL | 40 mL | 10 mL | 0 mL |
| Na$_2$HPO$_4$ Solution | 0 mL | 10 mL | 40 mL | 60 mL | 90 mL | 100 mL |
| pH | 5.3 | 6.3 | 7.0 | 7.5 | 8.1 | 9.2 |

A1-2. Betamethasone-Chondroitin Sulfate (Betamethasone (H)-Chondroitin Sulfate) Release Test Betamethasone-chondroitin sulfate (5 mg) was dissolved in each of the release test solutions A to F (10 mL), stored in a HPLC autosampler at 36° C., and subjected once a day to size exclusion chromatography (SEC). The measurement was made from Day 0 (initial value) to Day 6 after dissolution.

Conditions for HPLC are as follows.

analysis time: 40 minutes flow rate: 0.5 mL/min gradient: isoclatic solvent: acetonitrile (for HPLC):physiological saline=1:2 detection: by using a photodiode array (PDA), ratio of betamethasone-chondroitin sulfate and dissociated betamethasone at the maximum absorption wavelength (240 nm) of betamethasone was measured as an area %.

temperature: 36° C.

TABLE 4

|  | A (pH 5.3) | B (pH 6.3) | C (pH 7.0) | D (pH 7.5) | E (pH 8.1) | F (pH 9.2) |
| --- | --- | --- | --- | --- | --- | --- |
| day 0 | 0.0% | 0.0% | 0.1% | 0.1% | 0.4% | 2.3% |
| day 1 | 0.0% | 0.1% | 0.3% | 0.9% | 4.2% | 15.6% |
| day 2 | 0.0% | 0.1% | 0.5% | 2.0% | 7.4% | 25.9% |
| day 3 | 0.0% | 0.3% | 0.9% | 2.9% | 10.4% | 30.4% |
| day 4 | 0.2% | 0.3% | 1.2% | 3.9% | 13.5% | 35.3% |
| day 5 | 0.2% | 0.2% | 1.4% | 4.9% | 16.4% | 39.5% |
| day 6 | 0.3% | 0.5% | 1.7% | 6.0% | 18.7% | 42.8% |

A1-3. Betamethasone (F)-Chondroitin Sulfate Release Test

Betamethasone (F)-chondroitin sulfate (5 mg) was dissolved in each of the release test solutions A to F (10 mL), stored in a HPLC autosampler at 36° C., and subjected once a day to SEC measurement. The measurement was made from Day 0 (initial value) to Day 6 after dissolution. The HPLC conditions are the same as A1-2.

TABLE 5

|  | A (pH 5.3) | B (pH 6.3) | C (pH 7.0) | D (pH 7.5) | E (pH 8.1) | F (pH 9.2) |
| --- | --- | --- | --- | --- | --- | --- |
| day 0 | 1.2% | 2.0% | 9.1% | 9.5% | 25.0% | 67.3% |
| day 1 | 21.3% | 13.9% | 23.8% | 44.8% | 76.9% | 80.3% |
| day 2 | 22.7% | 23.2% | 33.2% | 66.3% | 90.5% | 95.1% |
| day 3 | 29.9% | 31.8% | 50.5% | 78.1% | 94.5% | 95.7% |
| day 4 | 35.6% | 39.0% | 59.5% | 85.3% | 95.6% | 96.3% |
| day 5 | 39.7% | 45.6% | 66.8% | 89.8% | 96.3% | 96.7% |
| day 6 | 46.5% | 52.1% | 72.7% | 92.8% | 96.6% | 96.7% |

A1-4. Betamethasone (Cl)-Chondroitin Sulfate Release Test

Betamethasone (Cl)-chondroitin sulfate (5 mg) was dissolved in each of the release test solutions A to F (10 mL), stored in a HPLC autosampler at 36° C., and subjected once a day to SEC measurement. The measurement was made from Day 0 (initial value) to Day 6 after dissolution. The HPLC conditions are the same as A1-2.

TABLE 6

|  | A (pH 5.3) | B (pH 6.3) | C (pH 7.0) | D (pH 7.5) | E (PH 8.1) | F (pH 9.2) |
| --- | --- | --- | --- | --- | --- | --- |
| day 0 | 0.5% | 1.8% | 0.9% | 4.6% | 14.2% | 52.1% |
| day 1 | 14.4% | 13.0% | 17.1% | 36.0% | 63.0% | 79.4% |
| day 2 | 21.0% | 20.5% | 28.2% | 52.9% | 73.5% | 82.1% |
| day 3 | 29.4% | 25.7% | 36.2% | 62.2% | 77.4% | 83.6% |
| day 4 | 33.5% | 29.5% | 41.7% | 66.8% | 79.8% | 85.5% |
| day 5 | 35.5% | 34.2% | 41.0% | 72.4% | 81.2% | 85.8% |
| day 6 | 37.3% | 36.2% | 43.8% | 74.3% | 82.2% | 86.0% |

A1-5. Betamethasone (Br)-Chondroitin Sulfate Release Test

Betamethasone (Br)-chondroitin sulfate (2 mg) was dissolved in each of the release test solutions A to F (4 mL), stored in a HPLC autosampler at 36° C., and subjected once a day to SEC measurement. The measurement was made from Day 0 (initial value) to Day 6 after dissolution. The HPLC conditions are the same as A1-2.

TABLE 7

|  | A (pH 5.3) | B (pH 6.3) | C (pH 7.0) | D (pH 7.5) | E (pH 8.1) | F (pH 9.2) |
| --- | --- | --- | --- | --- | --- | --- |
| day 0 | 2.0% | 6.9% | 7.7% | 7.8% | 14.9% | 28.1% |
| day 1 | 29.2% | 25.5% | 20.1% | 32.5% | 48.2% | 60.7% |
| day 2 | 35.1% | 28.0% | 26.0% | 42.1% | 57.7% | 70.9% |
| day 3 | 37.4% | 29.5% | 29.4% | 47.3% | 63.5% | 77.2% |
| day 4 | — | 34.0% | 33.7% | 52.9% | 67.8% | 80.7% |
| day 5 | 39.9% | 31.8% | 33.7% | 54.9% | 71.6% | 84.3% |
| day 6 | 40.8% | 32.7% | 35.6% | 57.9% | 74.8% | 87.1% |

A1-6. Comparison of Betamethasone (X)-Chondroitin Sulfate Release Rate

Comparison of the release rate of each conjugate in solution C (pH 7.0) and solution D (pH 7.5) is described below.

TABLE 8

| pH 7.0 | F | Cl | Br | H |
|---|---|---|---|---|
| day 0 | 9.1% | 0.9% | 7.7% | 0.1% |
| day 1 | 23.8% | 17.1% | 20.1% | 0.3% |
| day 2 | 33.2% | 28.2% | 26.0% | 0.5% |
| day 3 | 50.5% | 36.2% | 29.4% | 0.9% |
| day 4 | 59.5% | 41.7% | 33.7% | 1.2% |
| day 5 | 66.8% | 41.0% | 33.7% | 1.4% |
| day 6 | 72.7% | 43.8% | 35.6% | 1.7% |

TABLE 9

| pH 7.5 | F | Cl | Br | H |
|---|---|---|---|---|
| day 0 | 9.5% | 4.6% | 7.8% | 0.1% |
| day 1 | 44.8% | 36.0% | 32.5% | 0.9% |
| day 2 | 66.3% | 52.9% | 42.1% | 2.0% |
| day 3 | 78.1% | 62.2% | 47.3% | 2.9% |
| day 4 | 85.3% | 66.8% | 52.9% | 3.9% |
| day 5 | 89.8% | 72.4% | 54.9% | 4.9% |
| day 6 | 92.8% | 74.3% | 57.9% | 6.0% |

As it is shown in Tables 8 and 9, when the substituent group on the α position carbon of carboxylic acid is a halogen atom, the release rate is in the order of fluorine>chlorine>bromine>>hydrogen, exhibiting the result that is relevant to the strength of electronegativity (fluorine>chlorine>bromine>>hydrogen).

<Test Example A2> In Vitro Release Test (X=H, Cl, F, F, F) of CS (X)-Fenbufen and Felbinac In vitro release test was performed at the following conditions for each conjugate 31, 36, 45 which has been synthesized in Examples 5 to 7, CS-fenbufen (i.e., conjugate in which CS and fenbufen are coupled with unsubstituted aminoethanol therebetween) synthesized in Example 33, and CS-felbinac (i.e., conjugate in which CS and felbinac are coupled with unsubstituted aminoethanol therebetween) synthesized in Example 34.

(1) By using $NaH_2PO_4 \cdot 2H_2O$ and $Na_2HPO_4 \cdot 12H_2O$, each solution with pH 5.3, 6.3, 7.0, 7.5, 8.1, or 9.2 was prepared.

(2) Conjugate was dissolved to 0.05% in each solution prepared in above (1).

(3) After the storage for 36° C. and sampling every day, the peak area ratio of the conjugate, a single compound of fenbufen, and a single agent of felbinac was determined by HPLC (SEC: size exclusion chromatography).

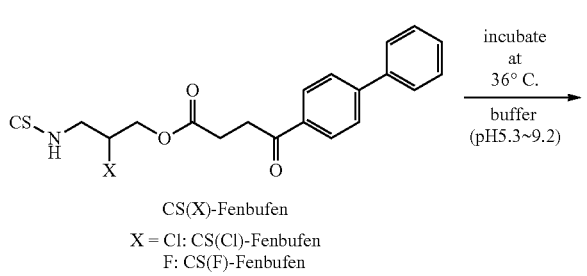

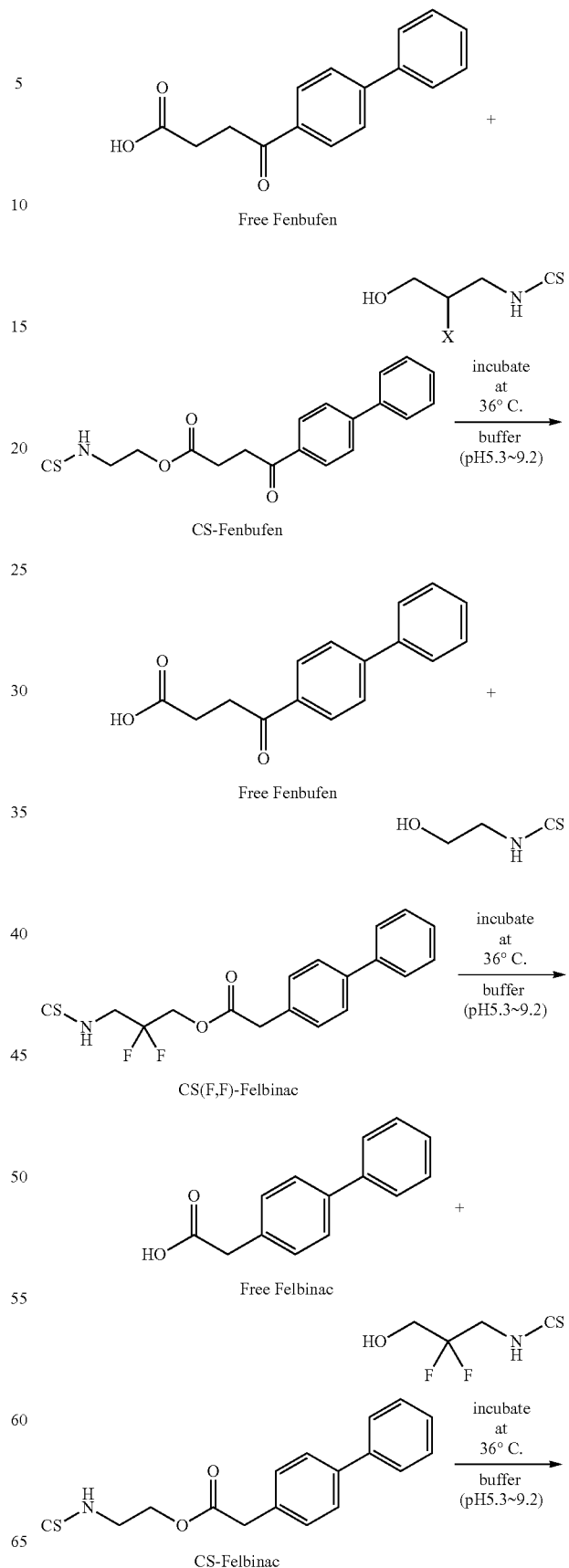

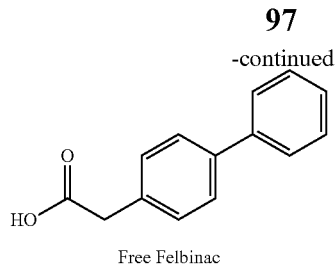

Free Felbinac

A2-1. Preparation of Solution for Release Test

Each of sodium dihydrogen phosphate dihydrate ($NaH_2PO_4.2H_2O$) (780 mg (5.0 mmol)) and disodium hydrogen phosphate dodecahydrate ($Na_2HPO_4.12H_2O$) (1.79 g (5.0 mmol)) was dissolved in WFI (500 mL) to give a $NaH_2PO_4$ solution and a $Na_2HPO_4$ solution. Those two solutions were admixed with each other at the following ratio and used as release test solutions A to F.

TABLE 10

|  | A | B | C | D | E | F |
|---|---|---|---|---|---|---|
| $NaH_2PO_4$ Solution | 100 mL | 90 mL | 60 mL | 40 mL | 10 mL | 0 mL |
| $Na_2HPO_4$ Solution | 0 mL | 10 mL | 40 mL | 60 mL | 90 mL | 100 mL |
| pH | 5.2 | 6.1 | 6.9 | 7.5 | 8.0 | 9.2 |

A2-2. CS-Fenbufen and CS-Felbinac Release Test

CS-fenbufen and CS-felbinac (about 5 mg for each) were dissolved in each of the release test solutions A to F to have concentration of 0.05%, stored in a HPLC autosampler at 36° C., and subjected once a day to SEC measurement. The dissociation ratio (%) of fenbufen and felbinac was measured from Day 0 (initial value) to Day 6 or Day 7 after dissolution. The dissociation ratio of fenbufen is described in Table 11. The dissociation ratio of felbinac is described in Table 12.
Conditions for HPLC are as follows.
analysis time: 40 minutes
flow rate: 0.5 mL/min
gradient: isoclatic
solvent: acetonitrile (for HPLC):physiological saline=1:2
detection: by using a PDA, ratio of CS-conjugate and dissociated drug at each maximum absorption wavelength (fenbufen: 285 nm, felbinac: 253 nm) was measured as an area %.
temperature: 36° C.

TABLE 11

| Felbinac dissociation ratio | | | | | | |
|---|---|---|---|---|---|---|
|  | A (pH 5.2) | B (pH 6.1) | C (pH 6.9) | D (pH 7.5) | E (pH 8.0) | F (pH 9.2) |
| day 0 | 0.0% | 0.0% | 0.0% | 0.0% | 0.2% | 3.6% |
| day 1 | 0.2% | 0.2% | 0.3% | 0.7% | 2.1% | 18.6% |
| day 2 | 0.3% | 0.3% | 0.5% | 1.2% | 3.9% | 32.4% |
| day 3 | 0.4% | 0.3% | 0.6% | 1.6% | 5.6% | 41.9% |
| day 4 | 0.5% | 0.4% | 0.8% | 2.1% | 7.1% | 44.6% |
| day 5 | 0.6% | 0.4% | 0.9% | 2.6% | 8.7% | 49.9% |
| day 6 | 0.6% | 0.4% | 1.0% | 2.9% | 9.9% | 53.6% |
| day 7 | 0.6% | 0.4% | 1.1% | 3.4% | 11.4% | 57.3% |

TABLE 12

| Felbinac dissociation ratio | | | | | | |
|---|---|---|---|---|---|---|
|  | A (pH5.2) | B (pH6.1) | C (pH6.9) | D (pH7.5) | E (pH8.0) | F (pH9.2) |
| day 0 | 0.0% | 0.0% | 0.0% | 0.0% | 0.2% | 3.6% |
| day 1 | 0.2% | 0.2% | 0.3% | 0.7% | 2.1% | 18.6% |
| day 2 | 0.3% | 0.3% | 0.5% | 1.2% | 3.9% | 32.4% |
| day 3 | 0.4% | 0.3% | 0.6% | 1.6% | 5.6% | 41.9% |
| day 4 | 0.5% | 0.4% | 0.8% | 2.1% | 7.1% | 44.6% |
| day 5 | 0.6% | 0.4% | 0.9% | 2.6% | 8.7% | 49.9% |
| day 6 | 0.6% | 0.4% | 1.0% | 2.9% | 9.9% | 53.6% |
| day 7 | 0.6% | 0.4% | 1.1% | 3.4% | 11.4% | 57.3% |

A2-3. CS (Cl)-Fenbufen Release Test

CS (Cl)-fenbufen (about 3 mg) was dissolved in each of the release test solution A to F to have concentration of 0.05%, stored in a HPLC autosampler at 36° C., and subjected once a day to SEC measurement. The dissociation ratio (%) of fenbufen was measured from Day 0 (initial value) to Day 6 after dissolution. The HPLC conditions are the same as A2-2. The results are shown in the following table.

TABLE 13

|  | A (pH5.2) | B (pH6.1) | C (pH6.9) | D (pH7.5) | E (pH8.0) | F (pH9.2) |
|---|---|---|---|---|---|---|
| day 0 | 0.1% | 0.1% | 0.2% | 0.4% | 0.8% | 5.7% |
| day 1 | 0.1% | 0.2% | 0.4% | 0.9% | 2.7% | 18.5% |
| day 2 | 0.1% | 0.2% | 0.7% | 1.5% | 2.7% | 28.1% |
| day 3 | 0.0% | 0.0% | 0.7% | 1.9% | 2.8% | 35.5% |
| day 4 | 0.0% | 0.1% | 0.4% | 2.4% | 3.2% | 41.0% |
| day 5 | 0.1% | 0.2% | 0.6% | 3.0% | 3.7% | 45.8% |
| day 6 | 0.1% | 0.2% | 0.7% | 3.6% | 4.4% | 50.2% |

A2-4. CS (F)-Fenbufen Release Test

CS (F)-fenbufen (about 10 mg) was dissolved in each of the release test solutions A to F to have concentration of 0.05%, stored in a HPLC autosampler at 36° C., and subjected once a day to SEC measurement. The dissociation ratio (%) of fenbufen was measured from Day 0 (initial value) to Day 6 after dissolution. The HPLC conditions are the same as A2-2. The results are shown in the following table.

TABLE 14

|  | A (pH5.2) | B (pH6.1) | C (pH6.9) | D (pH7.5) | E (pH8.0) | F (pH9.2) |
|---|---|---|---|---|---|---|
| day 0 | 0.0% | 0.0% | 0.0% | 0.4% | 1.2% | 8.8% |
| day 1 | 0.0% | 0.2% | 0.4% | 1.2% | 3.2% | 20.7% |
| day 2 | 0.2% | 0.3% | 1.0% | 1.9% | 5.1% | 30.0% |
| day 3 | 0.3% | 0.5% | 1.4% | 2.5% | 7.1% | 36.8% |
| day 4 | 0.4% | 0.7% | 1.7% | 3.3% | 9.0% | 43.0% |
| day 5 | 0.3% | 0.8% | 1.8% | 3.8% | 8.4% | 48.5% |
| day 6 | 0.3% | 0.7% | 1.8% | 4.3% | 6.1% | 53.0% |

A2-5. CS (F,F)-felbinac release test

CS (F,F)-felbinac (about 10 mg) was dissolved in each of the release test solutions A to F to have concentration of 0.05%, stored in a HPLC autosampler at 36° C., and subjected once a day to SEC measurement. The dissociation ratio (%) of felbinac was measured from Day 0 (initial value) to Day 7 after dissolution. The HPLC conditions are the same as A2-2. The results are shown in the following table.

TABLE 15

|   | A (pH5.2) | B (pH6.1) | C (pH6.9) | D (pH7.5) | E (pH8.0) | F (pH9.2) |
|---|---|---|---|---|---|---|
| day 0 | 0.0% | 0.0% | 0.0% | 1.1% | 3.3% | 15.9% |
| day 1 | 1.2% | 0.8% | 1.9% | 5.0% | 14.5% | 54.6% |
| day 2 | 0.9% | 0.9% | 2.5% | 7.2% | 23.5% | 68.5% |
| day 3 | 1.0% | 1.2% | 3.8% | 10.7% | 33.7% | 80.4% |
| day 4 | 1.2% | 1.6% | 5.1% | 14.1% | 42.4% | 87.4% |
| day 5 | 1.9% | 1.8% | 6.0% | 17.1% | 44.8% | 88.7% |
| day 6 | 2.1% | 2.1% | 7.1% | 20.3% | 50.5% | 91.2% |
| day 7 | 2.5% | 2.5% | 8.4% | 23.8% | 56.3% | 93.3% |

A2-6. Comparison of Release Rate Among CS-Fenbufen Conjugates

Regarding the results obtained from above, comparison of the dissociation ratio of CS-fenbufen, CS (Cl)-fenbufen and CS (F)-fenbufen at pH 6.9 and pH 7.5 is described in the following table.

TABLE 16

| pH6.9 | F | Cl | H | pH7.5 | F | Cl | H |
|---|---|---|---|---|---|---|---|
| day 0 | 0.0% | 0.2% | 0.2% | day 0 | 0.4% | 0.4% | 0.2% |
| day 1 | 0.4% | 0.4% | 0.2% | day 1 | 1.2% | 0.9% | 0.4% |
| day 2 | 1.0% | 0.7% | 0.2% | day 2 | 1.9% | 1.5% | 0.5% |
| day 3 | 1.4% | 0.7% | 0.2% | day 3 | 2.5% | 1.9% | 0.6% |
| day 4 | 1.7% | 0.4% | 0.3% | day 4 | 3.3% | 2.4% | 0.7% |
| day 5 | 1.8% | 0.6% | 0.3% | day 5 | 3.8% | 3.0% | 0.8% |
| day 6 | 1.8% | 0.7% | 0.3% | day 6 | 4.3% | 3.6% | 0.9% |

A2-7. Comparison of Release Rate Among CS-Felbinac Conjugates

Regarding the results obtained from above, comparison of the dissociation ratio of CS-felbinac and CS (F,F)-felbinac at pH 6.9 and pH 7.5 is described in the following table.

TABLE 17

| pH 6.9 | H | F, F | pH 7.5 | H | F, F |
|---|---|---|---|---|---|
| day 0 | 0.0% | 0.0% | day 0 | 0.0% | 1.1% |
| day 1 | 0.3% | 1.9% | day 1 | 0.7% | 5.0% |
| day 2 | 0.5% | 2.5% | day 2 | 1.2% | 7.2% |
| day 3 | 0.6% | 3.8% | day 3 | 1.6% | 10.7% |
| day 4 | 0.8% | 5.1% | day 4 | 2.1% | 14.1% |
| day 5 | 0.9% | 6.0% | day 5 | 2.6% | 17.1% |
| day 6 | 1.0% | 7.1% | day 6 | 2.9% | 20.3% |
| day 7 | 1.1% | 8.4% | day 7 | 3.4% | 23.8% |

<Test Example A3> Release Test for Conjugates Obtained from Examples 8 to 14

A3-1. Preparation of Solution for Release Test

Each of sodium dihydrogen phosphate dihydrate ($NaH_2PO_4 \cdot 2H_2O$) (780 mg (5.0 mmol)) and disodium hydrogen phosphate dodecahydrate ($Na_2HPO_4 \cdot 12H_2O$) (1.79 g (5.0 mmol)) was dissolved in WFI (500 mL) to give a $NaH_2PO_4$ solution and a $Na_2HPO_4$ solution. Those two solutions were admixed with each other at the following ratio and used as release test solutions A to F.

TABLE 18

|   | A | B | C | D | E | F |
|---|---|---|---|---|---|---|
| $NaH_2PO_4$ Solution | 100 mL | 90 mL | 60 mL | 40 mL | 10 mL | 0 mL |
| $Na_2HPO_4$ Solution | 0 mL | 10 mL | 40 mL | 60 mL | 90 mL | 100 mL |
| pH | 5.2 | 6.1 | 6.9 | 7.5 | 8.0 | 9.2 |

A3-2. Release Test for Each Conjugate

Each conjugate (about 5 mg) was dissolved in each of the release test solutions A to F to have concentration of 0.05%, stored in a HPLC autosampler at 36° C., and subjected once a day to SEC measurement. Measurement was made from Day 0 (initial value) to Day 7 after dissolution. The results are shown in the following table. In the table, "–" means no determination.

Meanwhile, Conditions for HPLC are as follows.

analysis time: 40 minutes flow rate: 0.5 mL/min gradient: isoclatic solvent: acetonitrile (for HPLC):physiological saline=1:2 detection: by using a PDA, ratio of the drug contained in CS-conjugate and dissociated drug at each maximum absorption wavelength was measured as an area %.

temperature: 36° C.

TABLE 19

| CS(F, F)-Indomethacin | | | | | |
|---|---|---|---|---|---|
| A (pH5.3) | B (pH6.2) | C (pH6.9) | D (pH7.5) | E (pH8.1) | F (pH9.1) |
| day 0 | 0.0% | 0.0% | 0.7% | 1.4% | 3.5% | 17.3% |
| day 1 | 0.0% | 0.7% | 1.7% | 2.9% | 11.4% | 40.9% |
| day 2 | 0.0% | 1.2% | 2.6% | 6.1% | 19.8% | 52.7% |
| day 3 | 0.4% | 0.7% | 3.6% | 10.3% | 25.1% | 61.1% |
| day 4 | 0.8% | 1.0% | 3.5% | 12.5% | 30.2% | 66.6% |
| day 5 | 1.7% | 1.8% | 7.2% | 14.9% | 34.5% | 70.1% |
| day 6 | 1.6% | 2.0% | 8.1% | 17.0% | 38.5% | 73.5% |
| day 7 | 1.9% | 2.2% | 9.0% | 19.2% | 42.0% | 76.0% |

TABLE 20

| CS(F, F)-Flurbiprofen | | | | | |
|---|---|---|---|---|---|
| A (pH5.3) | B (pH6.2) | C (pH6.9) | D (pH7.5) | E (pH8.1) | F (pH9.1) |
| day 0 | 0.0% | 0.0% | 0.0% | 0.3% | 3.0% | 23.8% |
| day 1 | 0.0% | 0.0% | 1.4% | 3.8% | 10.5% | 45.1% |
| day 2 | 0.1% | 0.2% | 2.2% | 6.6% | 18.6% | 64.7% |
| day 3 | 0.1% | 0.3% | 3.2% | 9.2% | 26.1% | 75.8% |
| day 4 | 0.1% | 0.4% | 3.6% | 10.7% | 28.3% | 78.5% |
| day 5 | 0.2% | 0.4% | 4.1% | 12.4% | 32.3% | 82.5% |
| day 6 | 0.3% | 0.7% | 5.5% | 14.8% | 37.8% | 86.8% |
| day 7 | 0.4% | — | 6.3% | 16.9% | 42.2% | 89.1% |

TABLE 21

CS(H)-Ketoprofen

| | A (pH5.3) | B (pH6.2) | C (pH6.9) | D (pH7.5) | E (pH8.1) | F (pH9.1) |
|---|---|---|---|---|---|---|
| day 0 | 0.0% | 0.0% | 0.0% | 0.0% | 0.0% | 0.4% |
| day 1 | 0.0% | 0.0% | 0.0% | 0.0% | 0.3% | 3.6% |
| day 2 | 0.0% | 0.0% | 0.0% | 0.1% | 0.6% | 6.3% |
| day 3 | 0.0% | 0.0% | 0.0% | 0.2% | 0.9% | 8.6% |
| day 4 | 0.0% | 0.0% | 0.0% | 0.3% | 1.2% | 10.0% |
| day 5 | 0.0% | 0.0% | 0.1% | 0.4% | 1.6% | 12.1% |
| day 6 | 0.1% | 0.2% | 0.1% | 0.6% | 1.9% | 14.0% |
| day 7 | 0.2% | 0.2% | 0.2% | 0.7% | 2.7% | 14.0% |

TABLE 22

CS(F)-Ketoprofen

| | A (pH5.3) | B (pH6.2) | C (pH6.9) | D (pH7.5) | E (pH8.1) | F (pH9.1) |
|---|---|---|---|---|---|---|
| day 0 | 0.2% | 0.2% | 0.2% | 0.3% | 0.7% | 5.5% |
| day 1 | 0.1% | 0.2% | 0.3% | 0.8% | 2.4% | 14.5% |
| day 2 | 0.1% | 0.2% | 0.5% | 1.3% | 4.9% | 23.3% |
| day 3 | 0.1% | 0.2% | 0.6% | 1.9% | 6.8% | 28.7% |
| day 4 | 0.1% | 0.2% | 0.8% | 2.9% | 8.7% | 32.3% |
| day 5 | 0.2% | 0.2% | 1.0% | 3.7% | 10.7% | 35.8% |
| day 6 | 0.2% | 0.3% | 1.3% | 4.4% | 12.9% | 38.9% |
| day 7 | 0.2% | 0.3% | 1.4% | 4.8% | 13.6% | 41.9% |

TABLE 23

CS(F, F)-Ketoprofen

| | A (pH5.3) | B (pH6.2) | C (pH6.9) | D (pH7.5) | E (pH8.1) | F (pH9.1) |
|---|---|---|---|---|---|---|
| day 0 | 0.1% | 0.0% | 0.3% | 0.7% | 2.8% | 19.0% |
| day 1 | 0.1% | 0.2% | 0.8% | 2.4% | 8.7% | 41.6% |
| day 2 | 0.2% | 0.3% | 1.3% | 4.7% | 14.7% | 56.7% |
| day 3 | 0.2% | 0.4% | 1.8% | 6.5% | 19.3% | 59.1% |
| day 4 | 0.3% | 0.6% | 2.5% | 8.3% | 24.0% | 64.4% |
| day 5 | 0.4% | 0.7% | 3.5% | 10.3% | 28.5% | 68.9% |
| day 6 | 0.5% | 0.9% | 4.2% | 12.2% | 32.6% | 72.8% |
| day 7 | 0.5% | 1.0% | 4.6% | 13.5% | 36.3% | 77.0% |

TABLE 24

CS(F, F)-Mefenamic acid

| | A (pH5.3) | B (pH6.2) | C (pH6.9) | D (pH7.5) | E (pH8.1) | F (pH9.1) |
|---|---|---|---|---|---|---|
| day 0 | 0.0% | 0.0% | 0.0% | 0.0% | 0.0% | 0.6% |
| day 1 | 0.0% | 0.0% | 0.0% | 0.0% | 0.5% | 3.4% |
| day 2 | 0.0% | 0.0% | 0.0% | 0.0% | 0.8% | 5.9% |
| day 3 | 0.0% | 0.0% | 0.0% | 0.4% | 1.1% | 6.8% |
| day 4 | 0.0% | 0.0% | 0.0% | 0.5% | 1.4% | 8.4% |
| day 5 | 0.0% | 0.0% | 0.0% | 0.6% | 1.7% | 9.3% |
| day 6 | 0.0% | 0.0% | 0.0% | 0.7% | 2.1% | 10.4% |
| day 7 | 0.0% | 0.0% | 0.0% | 0.7% | 2.3% | 11.1% |

TABLE 25

CS(F, F)-Loxoprofen (trans-OH)

| | A (pH5.3) | B (pH6.2) | C (pH6.9) | D (pH7.5) | E (pH8.1) | F (pH9.1) |
|---|---|---|---|---|---|---|
| day 0 | 0.0% | 0.0% | 0.0% | 0.0% | 0.6% | 0.7% |
| day 1 | 0.0% | 0.0% | 0.7% | 1.3% | 3.7% | 15.9% |
| day 2 | 0.0% | 0.0% | 0.9% | 2.3% | 6.5% | 27.6% |
| day 3 | 0.0% | 0.0% | 1.2% | 3.2% | 9.2% | 35.5% |
| day 4 | 0.0% | 0.0% | 1.5% | 4.6% | 12.2% | 41.7% |
| day 5 | 0.0% | 1.0% | 2.1% | 5.5% | 14.7% | 42.2% |
| day 6 | 0.8% | 1.1% | 2.4% | 6.6% | 17.1% | 46.7% |
| day 7 | 1.1% | 1.2% | 3.1% | 7.6% | 19.6% | 50.3% |

A3-3. Comparison of Release Rate Among CS-Ketoprofen Conjugates

Regarding the results obtained from above, comparison of the dissociation ratio of CS (H)-ketoprofen, CS (F)-ketoprofen, and CS (F,F)-ketoprofen at pH 6.9 and pH 7.5 is described in the following table.

TABLE 26

| pH6.9 | H | F | F, F | pH7.5 | H | F | F, F |
|---|---|---|---|---|---|---|---|
| day 0 | 0.0% | 0.2% | 0.3% | day 0 | 0.0% | 0.3% | 0.7% |
| day 1 | 0.0% | 0.3% | 0.8% | day 1 | 0.0% | 0.8% | 2.4% |
| day 2 | 0.0% | 0.5% | 1.3% | day 2 | 0.1% | 1.3% | 4.7% |
| day 3 | 0.0% | 0.6% | 1.8% | day 3 | 0.2% | 1.9% | 6.5% |
| day 4 | 0.0% | 0.8% | 2.5% | day 4 | 0.3% | 2.9% | 8.3% |
| day 5 | 0.1% | 1.0% | 3.5% | day 5 | 0.4% | 3.7% | 10.3% |
| day 6 | 0.1% | 1.3% | 4.2% | day 6 | 0.6% | 4.4% | 12.2% |
| day 7 | 0.2% | 1.4% | 4.6% | day 7 | 0.7% | 4.8% | 13.5% |

<Test Example A4> Release Test for Conjugates Obtained from Examples 15 to 17

The release test was performed at the following conditions for each conjugate of diclofenac (1-amino-2-propanol)-chondroitin sulfate (A4-1), diclofenac (serine ethyl ester)-chondroitin sulfate (A4-2), and diclofenac (threonine ethyl ester)-chondroitin sulfate (A4-3), which have been synthesized above.

Each conjugate was dissolved at 0.1% concentration in 20 mM sodium phosphate buffer solution (pH 7.0) and aliquoted. The amount of the dissociated diclofenac component which is present in an initial state (storage: Day 0) immediately after the dissolution, and the amount of diclofenac ester which has been forced to dissociate by using a base were subjected to quantitative analysis based on ODS-HPLC. Other aliquot was stored at 36° C. immediately after the dissolution, and after Day 1, 2, 4, or 8, the decomposition amount of diclofenac ester was similarly subjected to quantitative analysis. From the ratio between the obtained amount of the dissociated diclofenac component at each time point and the amount of dissociated diclofenac component resulting from forced dissociation, the dissociation ratio (%) was calculated.

For a pre-treatment of a HPLC sample, OASIS HLB was used, and a fraction eluted by acetonitrile was analyzed. The results are shown in the following table.

HPLC conditions are as follows.
  column: TSGgel ODS-100Z (4.6×150),
  flow rate: 1 mL/min
  temperature: 35° C.
  gradient: acetonitrile/20 mM sodium phosphate=0.40 (0 min)-0.68 (21 min)

TABLE 27

|       | A4-1 | A4-2  | A4-3  |
|-------|------|-------|-------|
| day 0 | 0.0% | 0.0%  | 0.1%  |
| day 1 | 0.7% | 10.9% | 2.0%  |
| day 2 | 1.1% | 16.9% | 4.0%  |
| day 4 | 1.8% | 31.9% | 7.2%  |
| day 8 | 3.0% | 42.2% | 10.5% |

<Test Example A5> Release Test for Conjugates Obtained from Examples 18 to 21

The release test was performed at the same conditions as the above Test example A4 for diclofenac (1-amino-3,3-dimethylbutan-2-ol)-chondroitin sulfate (A5-1), diclofenac (1-amino-2-butanol)-chondroitin sulfate (A5-2), diclofenac (2-amino-1-cyclohexylethan-1-ol)-chondroitin sulfate (A5-3), and diclofenac (4-amino-3-hydroxybutyric acid ethyl ester)-chondroitin sulfate (A5-4), which have been synthesized above. The results are shown in the following table.

TABLE 28

|       | A5-1 | A5-2 | A5-3 | A5-4 |
|-------|------|------|------|------|
| day 0 | 0.0% | 0.0% | 0.0% | 0.1% |
| day 1 | 0.0% | 0.1% | 0.1% | 0.4% |
| day 2 | 0.1% | 0.3% | 0.1% | 0.9% |
| day 4 | 0.1% | 0.6% | 0.2% | 1.7% |
| day 8 | 0.2% | 1.0% | 0.4% | 3.3% |

<Test Example A6> Release Test for Conjugates Obtained from Examples 22 to 25

The release test was performed at the same conditions as the above Test example A4 for diclofenac (1-amino-3,3-dimethylbutan-2-ol)-hyaluronic acid (A6-1), diclofenac (1-amino-2-butanol)-hyaluronic acid (A6-2), diclofenac (2-amino-1-cyclohexylethan-1-ol)-hyaluronic acid (A6-3), and diclofenac (4-amino-3-hydroxybutyric acid ethyl ester)-hyaluronic acid (A6-4), which have been synthesized above. The results are shown in the following table.

TABLE 29

|       | A6-1 | A6-2 | A6-3 | A6-4  |
|-------|------|------|------|-------|
| day 0 | 0.0% | 0.0% | 0.0% | 0.2%  |
| day 1 | 0.1% | 0.6% | 0.2% | 1.7%  |
| day 2 | 0.2% | 1.2% | 0.4% | 3.2%  |
| day 4 | 0.4% | 2.2% | 0.7% | 6.2%  |
| day 8 | 0.8% | 4.5% | 1.6% | 13.0% |

<Test Example A7> Release Test for Conjugates Obtained from Examples 26 to 28

The release test was performed at the following conditions for diclofenac (1-amino-2-propanol)-hyaluronic acid, diclofenac (serine ethyl ester)-hyaluronic acid, and diclofenac (threonine ethyl ester)-hyaluronic acid, which have been synthesized above.

Each conjugate was dissolved at 1% concentration in sodium citrate buffer solution (pH 5.1) and aliquoted. The amount of the dissociated diclofenac component which is present in a solution in an initial state (storage: Day 0) immediately after the dissolution was subjected to quantitative analysis based on ODS-HPLC. Other aliquot was stored at 40° C. immediately after the dissolution, and 4 weeks later, the decomposition amount of diclofenac ester was similarly subjected to quantitative analysis to calculate the content of dissociated diclofenac component in a solution. The results are shown in the following table. Meanwhile, the method for pre-treatment of HPLC sample is described below.

Methanol (1 mL) was added to the stored solution (1 g). After dilution and addition of acetonitrile to 20 mL, the hyaluronic acid component was allowed to precipitate. The obtained supernatant was used as a HPLC sample.

HPLC conditions are as follows.
column: TSGgel ODS-100Z (4.6 mm×150 mm)
flow rate: 1 mL/min
temperature: 35° C.
gradient: acetonitrile/20 mM sodium phosphate=0.40 (0 min)-0.68 (21 min)

TABLE 30

|  | Content of dissociated diclofenac (w/w %) | |
|---|---|---|
| Conjugate | Immediately after dissolution | 40° C., After 4 weeks |
| Diclofenac (1-amino-2-propanol)-hyaluronic acid | 0.00 | 0.00 |
| Diclofenac (serine ethyl ester)-hyaluronic acid | 0.05 | 0.72 |
| Diclofenac (threonine ethyl ester)-hyaluronic acid | 0.00 | 0.19 |

<Test Example A8> Release Test for Conjugates Obtained from Examples 29 to 31

(Change in dissociation characteristics caused by different spacer)

The compounds 29-3, 30-3 and 31-3 were dissolved in a buffer solution at each pH to have 5 mg/10 mL (0.05 w/w %) and heated for 1 week in an incubator at 36° C. Then, the drug dissociation ratio (%) during the incubation was evaluated in the same manner as Test example A1. The evaluation results are shown below.

TABLE 31

|     | Compound 29-3 | | Compound 30-3 | | Compound 31-3 | |
|-----|-------|-------|-------|-------|-------|-------|
| day | pH7.4 | pH8.0 | pH7.4 | pH8.0 | pH7.4 | pH8.0 |
| 0   | 0.4   | 1.7   | 1.1   | 4.3   | 0.5   | 0.0   |
| 1   | 2.0   | 6.3   | 5.7   | 14.4  | 0.2   | 0.5   |
| 2   | 3.6   | 10.9  | 9.3   | 23.5  | 0.2   | 0.7   |
| 3   | 5.3   | 16.1  | 11.0  | 29.3  | 0.2   | 1.1   |
| 4   | 8.7   | 21.7  | 15.4  | 37.8  | 1.5   | 2.8   |
| 5   | 11.0  | 26.1  | 19.6  | 44.7  | 2.1   | 3.8   |
| 6   | 12.2  | 28.3  | 22.1  | 48.7  | 1.9   | 4.3   |
| 7   | 11.5  | 29.3  | 22.0  | 50.6  | 0.6   | 2.8   |

<Test Example A9> Release Test for Conjugates Obtained from Examples 26 and 32

The release test was performed at the following conditions for diclofenac (1-amino-2-propanol)-hyaluronic acid and diclofenac-(2-aminoethanol)-hyaluronic acid, which have been synthesized above.

Each conjugate was dissolved at 1% concentration in sodium citrate buffer solution (pH 5.1) and aliquoted. The amount of the dissociated diclofenac component which is present in a solution in an initial state (storage: Day 0) immediately after the dissolution was subjected to quantitative analysis based on ODS-HPLC. Other aliquot was stored at 60° C., 40° C., or 25° C. immediately after the dissolution, the decomposition amount of diclofenac ester was similarly subjected to quantitative analysis after lapse of the each designated time. From the ratio between the obtained amount of the dissociated diclofenac component at each time point and the amount of dissociated diclofenac component resulting from forced dissociation, the dissociation ratio (%) was calculated. For a pre-treatment of a HPLC sample, OASIS HLB was used, and a fraction eluted by acetonitrile was analyzed. HPLC conditions are as follows.
column: TSGgel ODS-100Z (4.6 mm×150 mm)
flow rate: 1 mL/min
temperature: 35° C.
gradient: acetonitrile/20 mM sodium phosphate=0.40 (0 min) to 0.68 (21 min)

60° C.

TABLE 32

| day | Diclofenac-(2-aminoethanol)-hyaluronic acid | Diclofenac (1-amino-2-propanol)-hyaluronic acid |
|---|---|---|
| day 0 | 1.3% | 0.0% |
| day 7 | 8.1% | 1.9% |
| day 14 | 12.7% | 3.3% |
| day 21 | 16.4% | 4.6% |

40° C.

TABLE 33

| month | Diclofenac-(2-aminoethanol)-hyaluronic acid | Diclofenac (1-amino-2-propanol)-hyaluronic acid |
|---|---|---|
| 0 m | 1.3% | 0.0% |
| 4 m | 13.5% | 3.5% |
| 6 m | 18.2% | 5.2% |
| 9 m | 23.7% | 7.4% |
| 12 m | 28.2% | 9.3% |

25° C.

TABLE 34

| year | Diclofenac-(2-aminoethanol)-hyaluronic acid | Diclofenac (1-amino-2-propanol)-hyaluronic acid |
|---|---|---|
| 0 y | 1.3% | 0.0% |
| 0.5 y | 6.2% | 1.4% |
| 1 y | 10.9% | 2.7% |

Test Example A10

The release test was performed at the following conditions for bezafibrate (2-aminoethanol)-chondroitin sulfate and bezafibrate (2-amino-1-cyclohexylethan-1-ol)-chondroitin sulfate, which have been synthesized in Examples 35 and 36.

Each conjugate was dissolved at 0.1% concentration in 20 mM sodium phosphate buffer solution (pH 7.0) and aliquoted. The amount of the dissociated bezafibrate which is present in an initial state (storage: Day 0) immediately after the dissolution, and the amount of bezafibrate ester which has been forced to dissociate by using a base were subjected to quantitative analysis based on ODS-HPLC. Other aliquot was stored at 36° C. immediately after the dissolution, and after Day 1, 4, 8, 16, or 24 the decomposition amount of bezafibrate ester was similarly subjected to quantitative analysis. From the ratio between the obtained amount of the dissociated bezafibrate component at each time point and the amount of dissociated bezafibrate component resulting from forced dissociation, the dissociation ratio (%) was calculated. For a pre-treatment of a HPLC sample, OASIS HLB was used, and a fraction eluted by acetonitrile was analyzed.
HPLC conditions are as follows.
column: TSGgel ODS-100Z (4.6 mm×150 mm)
flow rate: 1 mL/min
temperature: 35° C.
gradient: acetonitrile/20 mM sodium phosphate=0.46

TABLE 35

| day | Bezafibrate (2-aminoethanol)-chondroitin sulfate | Bezafibrate (2-amino-1-cyclohexylethan-1-ol)-chondroitin sulfate |
|---|---|---|
| day 0 | 0.00% | 0.00% |
| day 1 | 0.12% | 0.00% |
| day 4 | 0.46% | 0.03% |
| day 8 | 0.57% | 0.03% |
| day 16 | 2.11% | 0.06% |
| day 24 | 3.33% | 0.07% |

<Test Example B1> Test for Measuring Various Betamethasone Coupled Chondroitin Sulfates Remained in Pulmonary Tissue of Normal Rat after Intratracheal Administration 1) System for Test As a system for test, BN/CrlCrlj rat (Charles River Laboratories International, Inc., 5-week old) was used.

2) Test Substance

As a test substance, various halogen-introduced betamethasone coupled chondroitin sulfates (F introduced: betamethasone (F)-CS, Beta-F-CS; Cl introduced: betamethasone (Cl)-CS, Beta-Cl-CS) and halogen-nonintroduced betamethasone coupled chondroitin sulfate (betamethasone (H)-CS, Beta-H-CS) were used after preparing them to have betamethasone concentration of 3 mg/mL by using phosphate buffered saline (PBS). Furthermore, a reference substance in which betamethasone phosphate is suspended to 3 mg/mL by using PBS was prepared.

3) Administration of Test Substance

For administration of each test substance, the test system was fixed dorsally under general anesthesia, and by using a sonde for intratracheal administration (MicroSprayer® Aerosolizer Model IA-1B, manufactured by Penn-Century), intratracheal administration was performed with volume of 100 μL. As general anesthesia, inhalation of isoflurane (Forane (registered trade mark), Dainippon Pharmaceutical Co., Ltd., concentration of 3.0%, flow rate of 2.0 L/min) filled in a small animal anesthetizer (TK-4, manufactured by BioMachinery Co., Ltd.) was used.

4) Measurement of Betamethasone Content in Pulmonary Tissue

At Hour 4, 24, 48, 72 and 168 after administration of a test substance, the pulmonary tissue was collected by using scissors and forceps under pentobarbital anesthesia. Meanwhile, three samples were taken for each evaluation time point. The obtained pulmonary tissue was collected in a polypropylene tube followed by measurement of the weight. An aqueous solution of ammonium formate (pH 6.0):methanol (3:2, v/v) were added at ratio of 40× (1 g:40 mL), and by using a hiscotron homogenizer, it was homogenated for about 1 minute under ice cooling. The obtained pulmonary tissue homogenate was used as a measurement sample. The obtained measurement sample was stored (−20° C.) under freeze until the measurement. Betamethasone content in pulmonary tissue was measured by liquid chromatography tandem mass spectrometry (LC-MS/MS) after extraction of the measurement sample with chloroform.methanol.

5) Parameters of Drug Kinetics

From the obtained betamethasone content in pulmonary tissue, parameters of drug kinetics were calculated. Each parameter of drug kinetics was calculated from a change in average content in pulmonary tissue. If there was an animal showing the measurement value of less than lower limit of quantification (<10 ng/g), the average content in pulmonary tissue was calculated by having the value of 0 (zero) for it. The time t (hr) for calculating $AUC_{0-t}$ was the final time point at which the quantification can be made. Meanwhile, for calculation of the parameters of drug kinetics, Non-compartmental analysis model analysis by WinNonlin Professional Ver 5.2.1 was used.

6) Results

The results are shown in FIG. 1 and the following table. When intratracheall administration of betamethasone coupled chondroitin sulfate was performed for a normal rat, for local administration, exposure of betamethasone was observed until 168 hours after the administration, which is the final evaluation point. Beta-F-CS exhibited the highest exposure amount until 168 hours after the administration. Meanwhile, a single agent of betamethasone exhibited the exposure only until 48 hours after the administration (lower limit for quantification: 10 ng/g). The elimination half life of the betamethasone after intratracheal administration of betamethasone coupled chondroitin sulfate was 29.5 to 128.0 hours. Meanwhile, the elimination half life of the betamethasone content in pulmonary tissue after intratracheal administration of single agent of betamethasone was 8.7 hours.

<Test Example B2> Whole Body Exposure Study after Intratracheal Administration of Various Betamethasone Coupled Chondroitin Sulfates in Normal Rat Whole body exposure after intratracheal administration of various betamethasone coupled chondroitin sulfates was evaluated based on plasma concentration of each rat which has been administered with each test substance in Test example B1.

1) Measurement of Plasma Concentration of Betamethasone

After the administration of a test substance, blood (300 µL) was collected, at Hour 0.5, 1, 2, 4, 8, 24, 48, 72 and 168, from a neck vein by using a terumo syringe attached with 27 G needle treated with heparin, and the blood was collected in a PP container (1.5 mL, manufactured by Assist). After that, the blood was rapidly centrifuged (1800×g, 4° C., 15 min) The obtained plasma (100 µL) was transferred to a PP container (1.5 mL, manufactured by Assist), added with 900 µL of an aqueous solution of ammonium formate (pH 6.0):methanol (1:2, v/v), and stirred. The resultant was used as a measurement sample and stored under freezing (−20° C.) until the measurement. The plasma concentration of betamethasone was measured by LC-MS/MS after extraction with chloroform.methanol.

2) Parameters of Drug Kinetics

From the obtained plasma concentration of betamethasone, parameters of drug kinetics were calculated. Each parameter of drug kinetics was calculated from a change in average content in plasma. If there was an animal showing the measurement value of less than lower limit of quantification (<5 ng/mL), the average content in plasma was calculated by having the value of 0 (zero) for it. Meanwhile, for calculation of the parameters of drug kinetics, Non-compartmental analysis model analysis by WinNonlin Professional Ver 5.2.1 was used.

3) Results

Figure 2:
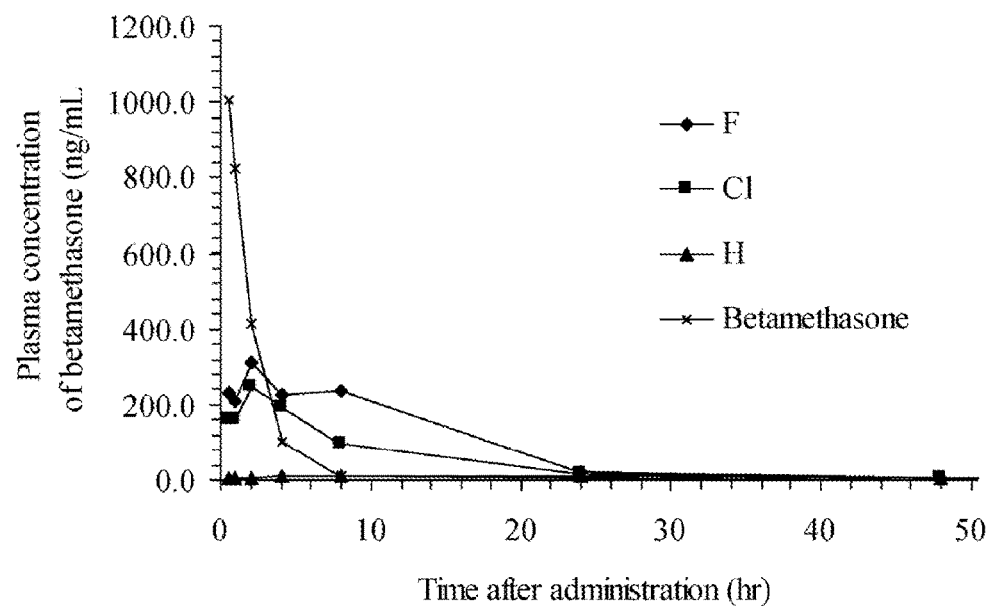
FIG. 2 is a graph illustrating the change of drug concentration in plasma after administration of a GAG derivative.

The results are shown in FIG. 2 and the following table. When a normal rat was given with betamethasone coupled chondroitin sulfate by intratracheal administration, the highest plasma concentration of betamethasone was lower than the value obtained from the administration of a single agent of betamethasone (i.e., about ⅓ to 1/100).

TABLE 36

| Test substance (dosage) | $C_{max}$ (ng/g) | $T_{max}$ (h$_r$) | $AUC_{0-t}$ (ng · h/g) | $AUC_{0-\infty}$ (ng · h/g) | $T_{1/2}$ (h$_r$) |
|---|---|---|---|---|---|
| Beta-F-CS (2.6 mg/body) | 7153 | 4 | 230999 | 237112 | 35.7 |
| Beta-Cl-CS (3.2 mg/body) | 6687 | 4 | 125919 | 127058 | 29.5 |
| Beta-H-CS (2.5 mg/body) | 218 | 4 | 19295 | 31988 | 128.0 |
| Betamethasone (0.3 mg/body) | 1189 | 4 | 21371 | 21797 | 8.7 |

TABLE 37

| Test substance (dosage) | $C_{max}$ (ng/g) | $T_{max}$ (hr) | $T_{1/2}$ (hr) |
|---|---|---|---|
| Beta-F-CS (2.6 mg/body) | 310.0 | 2 | 6.9 |
| Beta-Cl-CS (3.2 mg/body) | 248.0 | 2 | 7.8 |
| Beta-H-CS (2.5 mg/body) | 10.1 | 4 | 146.9 |
| Betamethasone (0.3 mg/body) | 1008.0 | 0.5 | 1.1 |

<Test Example B3> Determination of Effect of Nonsteroidal Anti-Inflammatory Drug Coupled Chondroitin Sulfates in Rat Model of Muscle Pain Induced by Silver Nitrate B3-1. Object The object was to evaluate the chondroitin sulfate derivatives which have been introduced with a nonsteroidal anti-inflammatory drug (NSAID), and the analgesic effect of the ketoprofen coupled chondroitin sulfate (KP-(F,F)-CS), indomethacin coupled chondroitin sulfate (IM-(F,F)-CS), felbinac coupled chondroitin sulfate (FB-(F,F)-CS) and diclofenac coupled chondroitin sulfate (DF-CS) was evaluated in the model.

B3-2. Methods

As an inflammatory agent, 0.1 mol/L silver nitrate solution was filtered through a 0.22 μm filter and used. As general anesthesia, inhalation of isoflurane (concentration of 3.0%, flow rate of 2.0 L/min) filled in a small animal anesthetizer (TK-4, manufactured by BioMachinery Co., Ltd.) was used.

A rat (Crj: SD line (SPF), male, 5-week old) was fixed dorsally under general anesthesia, and a broad region around the left gastrocnemius muscle was shaved using a shaver. The area for injection was sprayed with 70% alcohol for sterilization, and by using an injection tube applied with needle for subcutaneous insulin administration (MYJECTOR (registered trade mark), TERUMO CORPORATION), 0.1 mol/L silver nitrate solution was injected (volume of 100 μL/site) for intramuscular administration into the left gastrocnemius muscle of a rat. Accordingly, a rat model of muscle pain disorder caused by silver nitrate was prepared.

The following were prepared as a test substance in which phosphate buffered saline (PBS) is used as a solvent.
Test Substance:
(1) PBS (Control)
(2) 1% (w/v %) diclofenac coupled chondroitin sulfate (DF-CS)
(3) 5% (w/v %) fluorine introduced indomethacin coupled chondroitin sulfate (IM-(F,F)-CS)
(4) 5% (w/v %) fluorine introduced ketoprofen coupled chondroitin sulfate (KP-(F,F)-CS)
(5) 5% (w/v %) fluorine introduced felbinac coupled chondroitin sulfate (FB-(F,F)-CS)

At Hour 24 after the administration of 0.1 mol/L silver nitrate solution, the rats were divided into 5 groups, and each group was administered with either the test substance or PBS. As for the administration method, like the pain-causing substance, under inhalation of isoflurane, the region around the gastrocnemius muscle was sprayed with 70% alcohol for sterilization, and by using an injection tube applied with 29 G needle for subcutaneous insulin administration, it was injected (volume of 100 μL/site) for intramuscular administration into the left gastrocnemius muscle of a rat.

At Hour 24, 48 and 72 after the administration of the test substance, the walking behavior of each animal was observed by a naked eye under blinded conditions, and then 4-level scoring was made according to the following criteria. The results are shown in FIG. 3.

Figure 3:
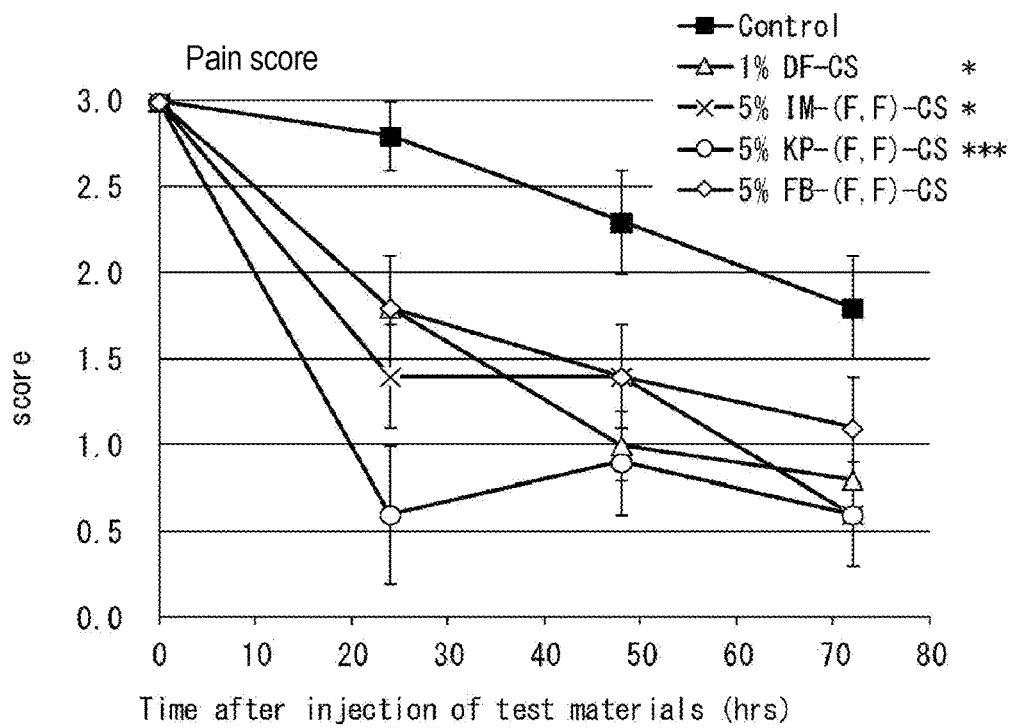
FIG. 3 is a graph illustrating the effect of a NSAID-introduced GAG derivative on pain score in a rat model of muscle pain disorder which is caused by silver nitrate.

In FIG. 3, the results are shown as the average pain score±standard error (number of samples for each group=8). Furthermore, *** and * represent, in the parametric Tukey test, ***$p<0.001$ and *$p<0.05$ (vs Control), respectively.

(Criteria)
Score 0: Normal
Score 1: Mild claudication
Score 2: Severe claudication
Score 3: Walking on three legs Furthermore, the rat after the score evaluation at Hour 24, 48 and 72 after the administration of a test substance was hold in a cotton glove under blinded conditions, and pressed on the temporal skin in the left medial gastrocnemius muscle by using a device for measuring analgesic effect in rat (Randall-Selitto method, Muromachi Kikai Co., Ltd.) attached with blunt-end probe. The length of move of the weight at which a pain-related behavior like avoidance is shown was read to one decimal place. This operation was repeated three times in total, and the median value was taken as the muscle pressure pain threshold. The results are shown in FIG. 4.

Figure 4:
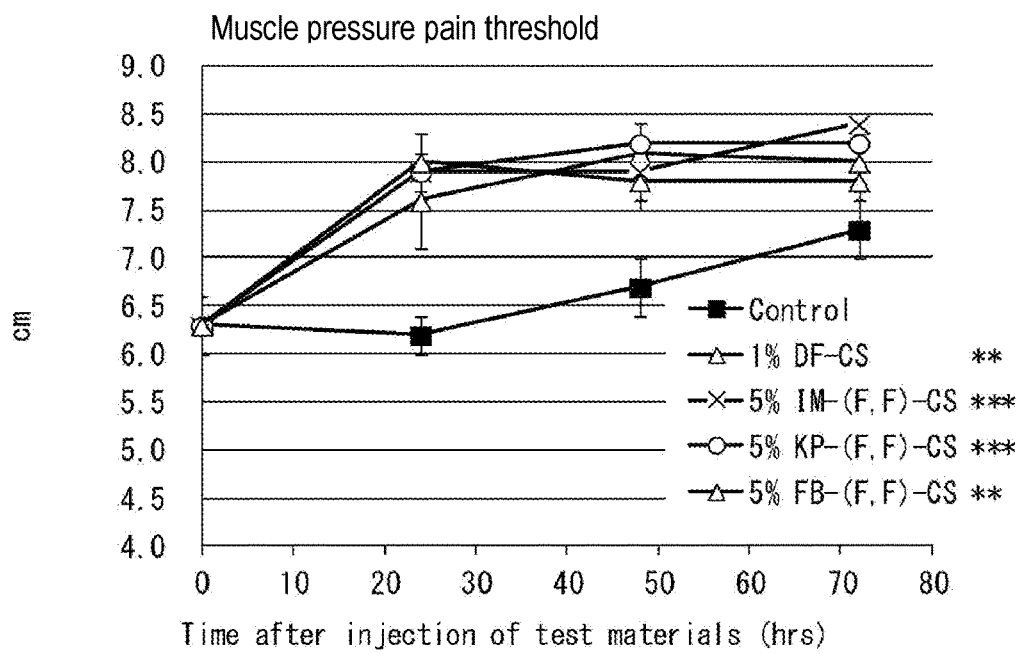
FIG. 4 is a graph illustrating the effect of a NSAID-introduced GAG derivative on muscle pressure pain threshold in a rat model of muscle pain disorder which is caused by silver nitrate.

In FIG. 4, the results are shown as the average stimulation pressure±standard error (number of samples for each group=8). Furthermore, *** and * represent, in the parametric Tukey test, ***$p<0.001$ and *$p<0.05$ (vs Control), respectively.

B3-4. Results

From FIG. 3, it was found that, by 1% DF-CS, 5% IM-(F,F)-CS, and 5% KP-(F,F)-CS, the pain score was improved in a significant sense compared to the control group. Meanwhile, although no difference in a significant sense was observed from 5% FB-(F,F)-CS compared to the control group, the score was lower than the control group at any evaluation point.

Furthermore, from FIG. 4, it was found that, by 1% DF-CS, 5% IM-(F,F)-CS, 5% KP-(F,F)-CS, and 5% FB-(F,F)-CS, the muscle pressure pain threshold value was increased in a significant sense compared to the control group. There was no clear difference observed among those compounds.

<Test Example B4> Determination of Effect of Ketoprofen Coupled Chondroitin Sulfate in Rat Model of Muscle Pain Induced by Silver Nitrate B4-1. Object The object was to evaluate the influence of a difference in release rate on efficacy by comparing analgesic effect of ketoprofen coupled chondroitin sulfates (KP-CS, KP-(F)-CS and KP-(F,F)-CS) which have a different spacer coupling mode.

B4-2. Methods

The test was performed according to the experimental order of the above Test example B3, and the evaluation of the following test substances was used.
Test Substance:
(1) PBS (Control)
(2) 5% (w/v %) ketoprofen coupled chondroitin sulfate solution (KP-CS)
(3) 5% (w/v %) fluorine introduced ketoprofen coupled chondroitin sulfate solution (KP-(F)-CS)
(4) 5% (w/v %) fluorine introduced ketoprofen coupled chondroitin sulfate solution (KP-(F,F)-CS)

Similarly to the above Test example B3, the walking behavior of each animal was observed by a naked eye under blinded conditions, and then 4-level scoring was made according to the following criteria. The results are shown in FIG. 5.

Figure 5:
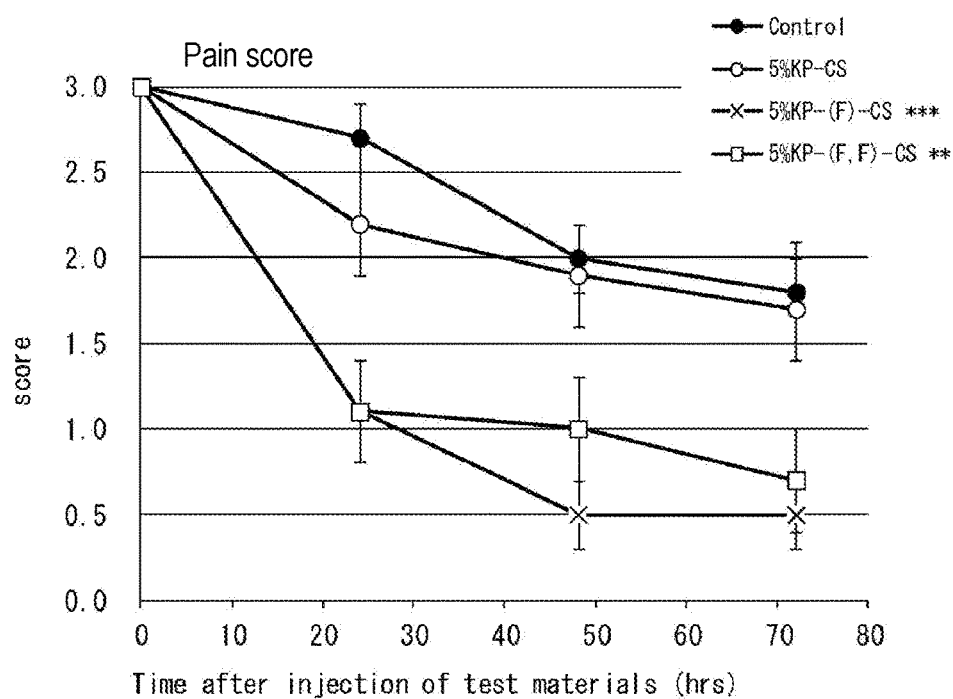
FIG. 5 is a graph illustrating the effect of a ketoprofen coupled chondroitin sulfate on pain score in a rat model of muscle pain disorder which is caused by silver nitrate.

In FIG. 5, the results are shown as the average pain score±standard error (number of samples for each group=10). Furthermore, * and  represent, in the parametric Dunnett test, *$p<0.001$ and $p<0.01$ (vs Control), respectively.

(Criteria)
Score 0: Normal
Score 1: Mild claudication
Score 2: Severe claudication
Score 3: Walking on three legs Similar to the above Test example B3, the rat was pressed by using a device for measuring analgesic effect in rat under blinded conditions and the muscle pain threshold was evaluated. The results are shown in FIG. 6.

Figure 6:
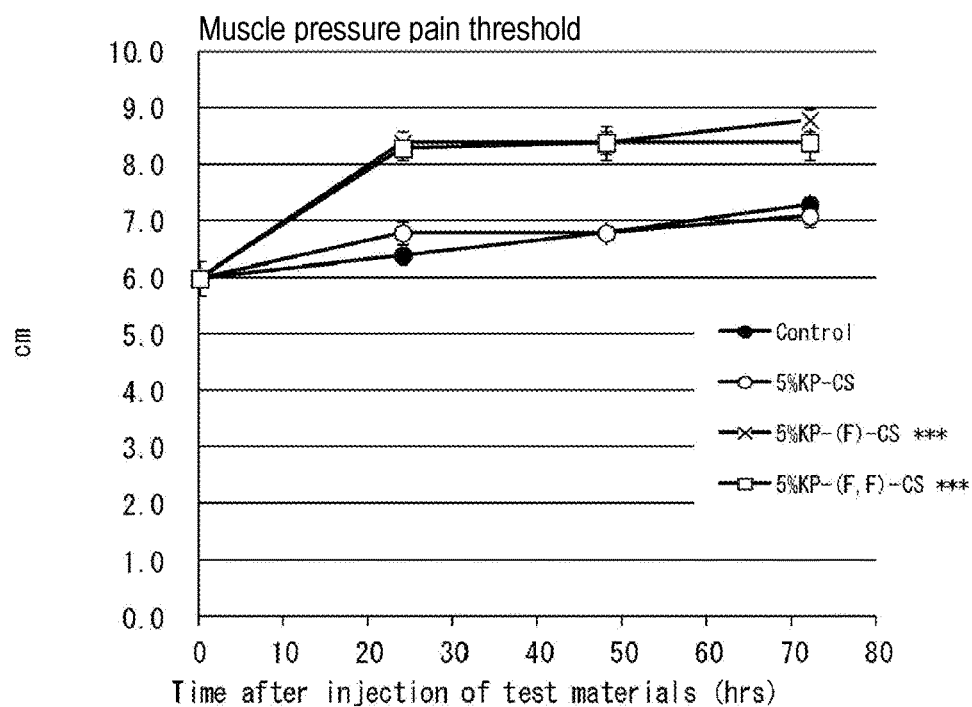
FIG. 6 is a graph illustrating the effect of a ketoprofen coupled chondroitin sulfate on muscle pressure pain threshold in a rat model of muscle pain disorder which is caused by silver nitrate.

In FIG. 6, the results are shown as the average stimulation pressure±standard error (number of samples for each group=10). Furthermore, * represents, in the parametric Dunnett test, *$p<0.001$ (vs Control).

B4-3. Results

From FIG. 5, it was found that, in the KP-(F)-CS and KP-(F,F)-CS groups, the pain score was improved in a significant sense compared to the control group. Meanwhile, KP-CS group showed a slightly lower score value on Day 1 after the administration. However, the effect was weak and there was no difference in a significant sense observed compared to the control group.

Furthermore, from FIG. 6, it was found that, in the KP-(F)-CS and KP-(F,F)-CS groups, the muscle pressure pain threshold value was increased in a significant sense compared to the control group. There was no clear difference observed between those groups. Meanwhile, there was no significant difference with the KP-CS group and the control group, and they exhibited almost the same profile to each other for 3 days after the administration.

B4-4. Conclusion

Any one of 5% KP-(F)-CS and 5% KP-(F,F)-CS exhibited an analgesic effect for 3 days. Meanwhile, 5% KP-CS did not exhibit an effect of improving pain score or an effect of increasing a pressure pain threshold value. According to a separate in vitro release test, it was confirmed that the KP release is fast in the order of KP-(F,F)-CS>KP-(F)-CS>KP-CS, and thus it was believed that the KP released from the coupled product exhibits an analgesic effect.

<Test Example B5> Determination of Effect of Diclofenac Coupled Hyaluronic Acids Having Different Coupling Mode in Rat Model of Muscle Pain Induced by Silver Nitrate

B5-1. Object

According to the object of determining the influence of a difference in coupling mode of hyaluronic acid derivative, to which the nonsteroidal anti-inflammatory drug (NSAID) has been introduced, on efficacy, the analgesic effect of diclofenac coupled hyaluronic acid (diclofenac-aminoethanol-hyaluronic acid: DF-HA), diclofenac coupled hyaluronic acid introduced with a sterically hindered group (diclofenac-(1-amino-2-propanol)-hyaluronic acid: DF-(Me)-HA) was evaluated.

B5-2. Methods

As an inflammatory agent, 0.1 mol/L silver nitrate solution was filtered through a 0.22 μm filter and used. As general anesthesia, inhalation of isoflurane (concentration of 3.0%, flow rate of 2.0 L/min) filled in a small animal anesthetizer (TK-4, manufactured by BioMachinery Co., Ltd.) was used.

A rat (Crj: SD line (SPF), male, 5-week old) was fixed dorsally under general anesthesia, and a broad region around the left gastrocnemius muscle was shaved using a shaver. The area for injection was sprayed with 70% alcohol for sterilization, and by using an injection tube applied with needle for subcutaneous insulin administration (MYJECTOR (registered trade mark), TERUMO CORPORATION), 0.1 mol/L silver nitrate solution was injected (volume of 100 μL/site) for intramuscular administration into the left gastrocnemius muscle of a rat. Accordingly, a rat model of muscle pain disorder caused by silver nitrate was prepared.

The following were prepared as a test substance in which citric acid buffer is used as a solvent.

Test Substance:
(1) citric acid buffer (Control)
(2) 1% (w/v %) diclofenac coupled hyaluronic acid (DF-HA)
(3) 1% (w/v %) diclofenac coupled hyaluronic acid introduced with a sterically hindered group (DF-(Me)-HA)

At Hour 24 after the administration of 0.1 mol/L silver nitrate solution, the rats were divided into 3 groups, and each group was administered with either the test substance or citric acid buffer solution. As for the administration method, like the pain-causing substance, under inhalation of isoflurane, the region around the gastrocnemius muscle was sprayed with 70% alcohol for sterilization, and by using an injection tube applied with 29 G needle for subcutaneous insulin administration, it was injected (volume of 100 μL/site) for intramuscular administration into the left gastrocnemius muscle of a rat.

At Hour 24, 48 and 72 after the administration of the test substance, the walking behavior of each animal was observed by a naked eye under blinded conditions, and then 4-level scoring was made according to the following criteria. The results are shown in FIG. 7.

Figure 7:
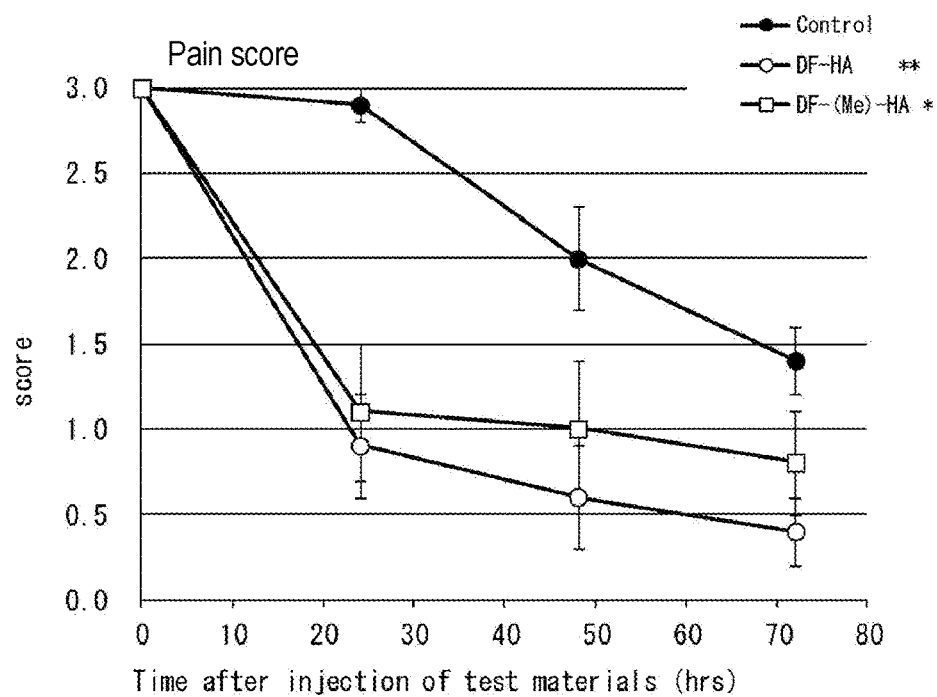
FIG. 7 is a graph illustrating the effect of a diclofenac coupled hyaluronic acid on pain score in a rat model of muscle pain disorder which is caused by silver nitrate.

In FIG. 7, the results are shown as the average pain score±standard error (number of samples for each group=8). Furthermore, ** and * represent, in the parametric Tukey test, **$p<0.01$ and *$p<0.05$ (vs Control), respectively.

(Criteria)
Score 0: Normal
Score 1: Mild claudication
Score 2: Severe claudication
Score 3: Walking on three legs Furthermore, the rat after the score evaluation at Hour 24, 48 and 72 after the administration of a test substance was hold in a cotton glove under blinded conditions, and pressed on the temporal skin in the left medial gastrocnemius muscle by using a device for measuring analgesic effect in rat (Randall-Selitto method, Muromachi Kikai Co., Ltd.) attached with blunt-end probe. The length of move of the weight at which a pain-related behavior like avoidance is shown was read to one decimal place. This operation was repeated three times in total, and the median value was taken as the muscle pressure pain threshold value. The results are shown in FIG. 8.

Figure 8:
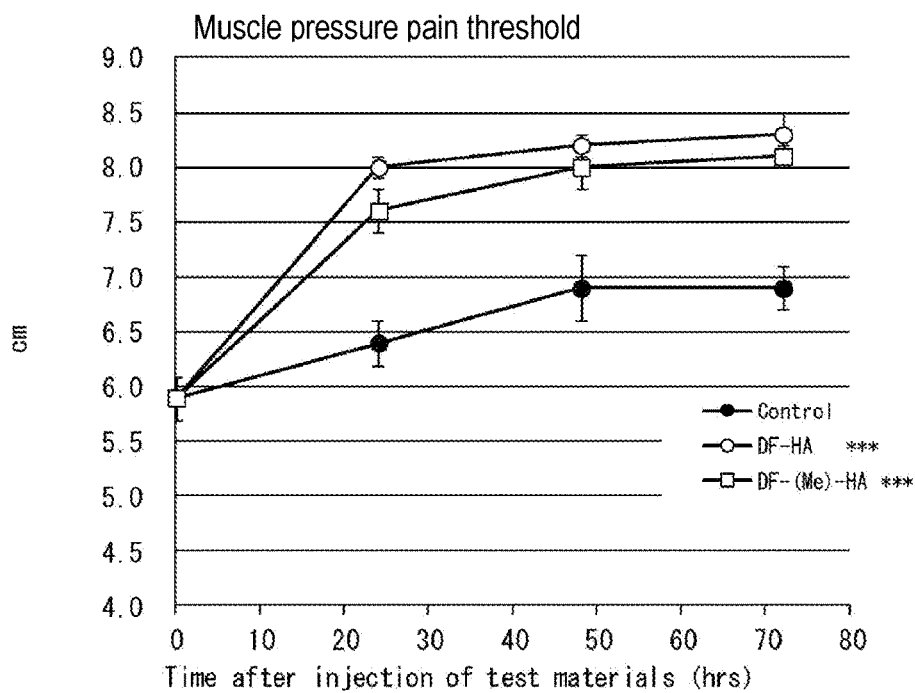
FIG. 8 is a graph illustrating the effect of a diclofenac coupled hyaluronic acid on muscle pressure pain threshold in a rat model of muscle pain disorder which is caused by silver nitrate.

In FIG. 8, the results are shown as the average stimulation pressure±standard error (number of samples for each group=8). Furthermore, * represents, in the parametric Tukey test, *p<0.001 (vs Control).

B5-3. Results

From FIG. 7, it was found that, in the 1% DF-HA and 1% DF-(Me)-HA, the pain score was improved in a significant sense compared to the control group. No clear difference in a significant sense was observed between the compounds.

Furthermore, from FIG. 8, it was found that, by any one of 1% DF-HA and 1% DF-(Me)-HA, the muscle pressure pain threshold value was increased in a significant sense compared to the control group. No clear difference was observed between those compounds, and they behaved almost identically for 3 days after the administration.

B5-4. Conclusion

The analgesic effect was shown for 3 days by any one of 1% DF-HA and 1% DF-(Me)-HA. No difference in a significant sense was observed between the compounds, and it is believed that the analgesic effect for 3 days after the administration is also the same.

<Test Example B6> Determination of Effect of Diclofenac Coupled Hyaluronic Acid in Rat Model of Muscle Pain Disorder that is Caused by Carrageenan

B6-1. Object

According to the object of determining the long-acting analgesic effect of intramuscular administration of diclofenac coupled sodium hyaluronate (DF-HA), the analgesic effect of DF-HA 10 days after the administration was evaluated using the above model.

B6-2. Methods

The following were prepared as a test substance in which citric acid buffer is used as a solvent.
Test Substance:
(1) citric acid buffer (Control)
(2) 1% (w/v %) diclofenac coupled hyaluronic acid (DF-HA)

As an inflammatory agent, 10 mg/mL carrageenan solution was used. As general anesthesia, inhalation of isoflurane (concentration of 3.0%, flow rate of 2.0 L/min) filled in a small animal anesthetizer (TK-4, manufactured by BioMachinery Co., Ltd.) was used.

A rat (Crj: SD line (SPF), male, 8-week old) was fixed dorsally under general anesthesia, and a broad region around the left gastrocnemius muscle was shaved using a shaver. The area for injection was sprayed with 70% alcohol for sterilization, and by using an injection tube applied with needle for subcutaneous insulin administration (MYJECTOR (registered trade mark), TERUMO CORPORATION), each test solution was injected (volume of 100 μL/site) for intramuscular administration into the left medial gastrocnemius muscle of a rat.

10 Days after administering the test substance, each group was administered with 10 mg/mL carrageenan solution. As for the administration method, like the test substance, under inhalation of isoflurane, the region around the gastrocnemius muscle was sprayed with 70% alcohol for sterilization, and by using an injection tube applied with 29 G needle for subcutaneous insulin administration, it was injected (volume of 100 μL/site) for intramuscular administration into the left gastrocnemius muscle of a rat.

At Hour 3 after the administration of the carrageenan solution, the stimulation pressure evaluation was performed for the administration site by using a PAM device (manufactured by Bio Research Center) which measures an analgesic effect. Specifically, after applying pressure stimulation on an administration site (temporal region in medial gastrocnemius muscle), the stimulation pressure (N (Newton)) at which the rat shows an avoidance response (i.e., paw withdrawal, crying, jerks and shaking, or the like) as a result of applying the pressure stimulation on the temporal region in gastrocnemius muscle was measured. The results are shown in FIG. 9.

Figure 9:
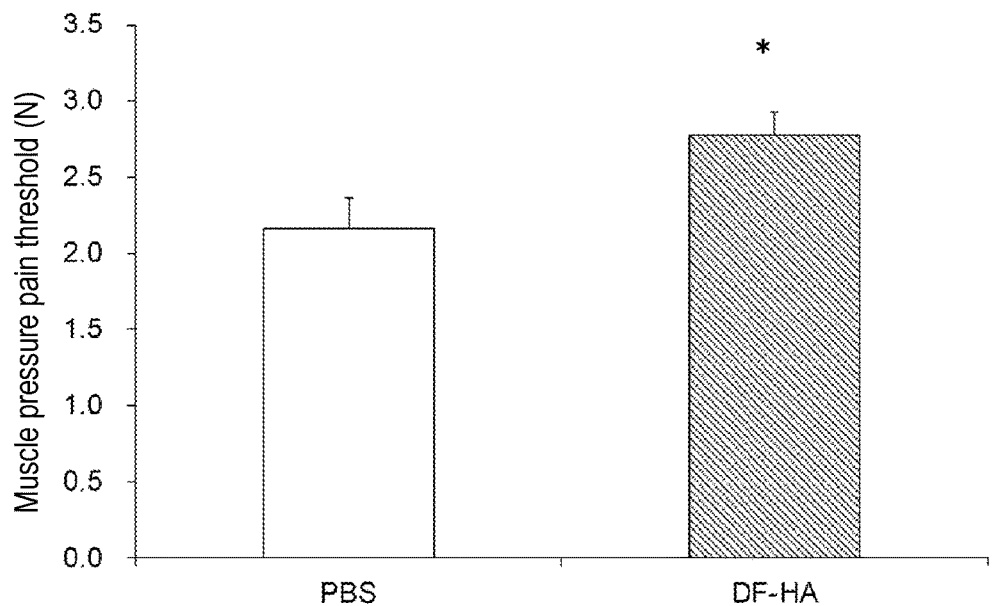
FIG. 9 is a graph illustrating the effect of a diclofenac coupled hyaluronic acid on muscle pressure pain threshold in a rat model of muscle disorder which is caused by carrageenan.

In FIG. 9, the results are shown as the average stimulation pressure±standard error (number of samples for each group=7). Furthermore, * represents, in the t test, *p<0.05 (vs Control).

B6-3. Results

From FIG. 9, it was found that, by 1% DF-HA which has been applied 10 days ago by intramuscular administration, the muscle pressure pain threshold value was increased in a significant sense compared to the control group.

B6-4. Conclusion

It was concluded that the analgesic effect is exhibited for 10 days by 1% DF-HA which has been applied by intramuscular administration.

<Test Example B7> Determination of Effect of Diclofenac Coupled Sodium Hyaluronates Having Different Coupling Mode in Rat Model of Muscle Pain Disorder that is Caused by Carrageenan

B7-1. Object

According to the object of determining influence of a difference in coupling mode of hyaluronic acid derivative, to which the nonsteroidal anti-inflammatory drug (NSAID) has been introduced, on efficacy, the analgesic effect of diclofenac coupled hyaluronic acid (diclofenac-aminoethanol-hyaluronic acid: DF-HA), and diclofenac coupled hyaluronic acid introduced with a sterically hindered group (diclofenac-(1-amino-2-propanol)-hyaluronic acid: DF-(Me)-HA) were evaluated 14 days after the administration.

B7-2. Methods

The following were prepared as a test substance in which citric acid buffer is used as a solvent.
Test Substance:
(1) citric acid buffer (Control)
(2) 1% (w/v %) diclofenac coupled hyaluronic acid (DF-HA)
(3) 1% (w/v %) diclofenac coupled hyaluronic acid introduced with a sterically hindered group (DF-(Me)-HA)

As an inflammatory agent, 10 mg/mL carrageenan solution was used. As general anesthesia, inhalation of isoflurane (concentration of 3.0%, flow rate of 2.0 L/min) filled in a small animal anesthetizer (TK-4, manufactured by BioMachinery Co., Ltd.) was used.

A rat (Crj: SD line (SPF), male, 7-week old) was fixed dorsally under general anesthesia, and a broad region around the left gastrocnemius muscle was shaved using a shaver. The area for injection was sprayed with 70% alcohol for sterilization, and by using an injection tube applied with needle for subcutaneous insulin administration (MYJECTOR (registered trade mark), TERUMO CORPORATION), each test solution was injected (volume of 100 μL/site) for intramuscular administration into the left medial gastrocnemius muscle of a rat.

14 Days after administering the test substance, each group was administered with 10 mg/mL carrageenan solution. As for the administration method, like the test substance, under inhalation of isoflurane, the region around the gastrocnemius muscle was sprayed with 70% alcohol for sterilization, and by using an injection tube applied with 29 G needle for subcutaneous insulin administration, it was injected (volume of 100 μL/site) for intramuscular administration into the left gastrocnemius muscle of a rat.

At Hour 3 after the administration of the carrageenan solution, the stimulation pressure evaluation was performed for the administration site by using a PAM device (manufactured by Bio Research Center) which measures an analgesic effect. Specifically, after applying pressure stimulation on an administration site (temporal region in medial gastrocnemius muscle), the stimulation pressure (N (Newton)) at which the rat shows a pain-related behaviour (i.e., paw withdrawal, crying, jerks and shaking, or the like) as a result of pressure stimulation on the temporal region in gastrocnemius muscle was measured. The results are shown in FIG. 10.

Figure 10:
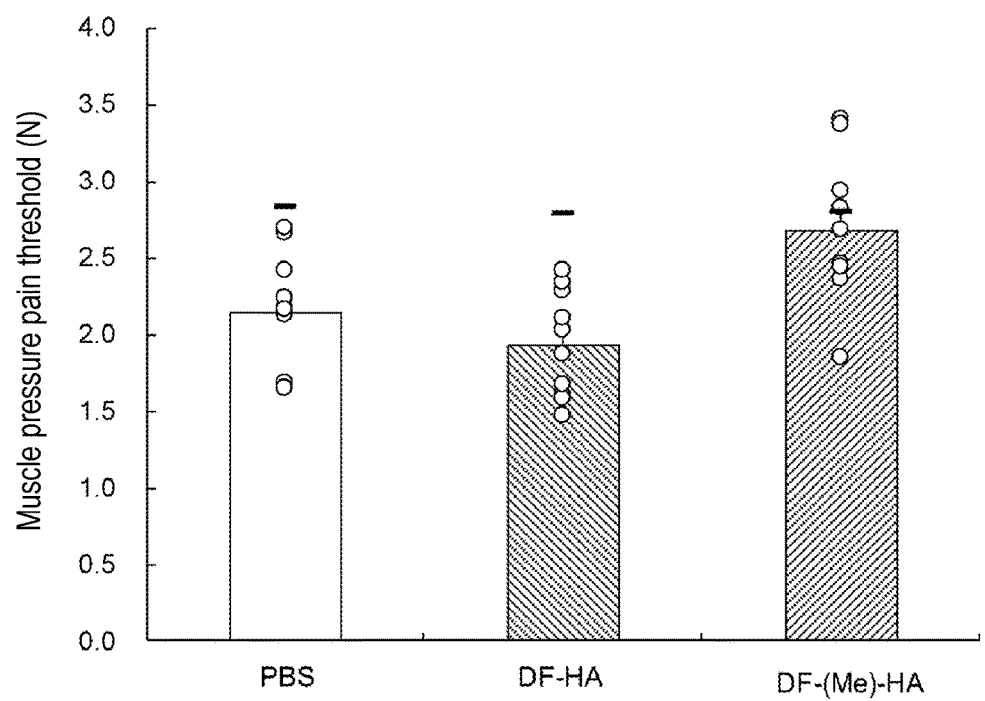
FIG. 10 is a graph illustrating the effect of a diclofenac coupled hyaluronic acid on muscle pressure pain threshold in a rat model of muscle disorder which is caused by carrageenan.

In FIG. 10, the results are shown as the average stimulation pressure±standard error (number of samples for each group=10).

B7-3. Results

From FIG. 10, it was found that, by 1% DF-HA which has been applied 14 days ago by intramuscular administration, the muscle pressure pain threshold value was not increased, and no difference in a significant sense was observed compared to the control group. Meanwhile, 1% DF-(Me)-HA has increased in a significant sense the muscle pressure pain threshold value compared to the control group (i.e., p<0.05 (vs Control) according to t test).

B7-4. Conclusion

It was concluded that the analgesic effect is exhibited for 14 days by 1% DF-(ME)-HA while the analgesic effect by 1% DF-HA applied by intramuscular administration lasts less than 14 days. Thus, the long-acting efficacy of DF-(Me)-HA compared to DF-HA was clearly demonstrated.

From the above, it was found that the GAG derivative of this embodiment can control the drug dissociation rate without significantly depending on a drug structure. It was also found that the drug release at administration site can be achieved for desired period of time.

<Test Example B8> Determination of Effect of Diclofenac Coupled Chondroitin Sulfate in Rat Model of Muscle Pain Disorder that is Caused by Carrageenan B8-1. Object According to the object of determining the long-acting analgesic effect of intramuscular administration of diclofenac coupled chondroitin sulfate (diclofenac-(2-aminoethanol)-chondroitin sulfate: DF-CS), the analgesic effect of DF-CS 7 days after the administration was evaluated using the above model.

B8-2. Methods

The followings were prepared as a test substance in which PBS is used as a solvent.
Test Substance:
(1) PBS (Control)
(2) 1% (w/v %) diclofenac coupled chondroitin sulfate (DF-CS)

As an inflammatory agent, 10 mg/mL carrageenan solution was used. As general anesthesia, inhalation of isoflurane (concentration of 3.0%, flow rate of 2.0 L/min) filled in a small animal anesthetizer (TK-4, manufactured by BioMachinery Co., Ltd.) was used.

A rat (Crj: SD line (SPF), male, 9-week old) was fixed dorsally under general anesthesia, and a broad region around the left gastrocnemius muscle was shaved using a shaver. The area for injection was sprayed with 70% alcohol for sterilization, and by using an injection tube applied with needle for subcutaneous insulin administration (MYJECTOR (registered trade mark), TERUMO CORPORATION), the test solution was injected (volume of 100 μL/site) for intramuscular administration into the left gastrocnemius muscle of a rat.

7 Days after administering the test substance, each group was administered with 10 mg/mL carrageenan solution. As for the administration method, like the test substance, under inhalation of isoflurane, the region around the gastrocnemius muscle was sprayed with 70% alcohol for sterilization, and by using an injection tube applied with 29 G needle for subcutaneous insulin administration, it was injected (volume of 100 μL/site) for intramuscular administration into the left gastrocnemius muscle of a rat.

At Hour 3 after the administration of the carrageenan solution, the stimulation pressure evaluation was performed for the administration site by using a PAM device (manufactured by Bio Research Center) which measures an analgesic effect. Specifically, after applying pressure stimulation on an administration site (temporal region in medial gastrocnemius muscle), the stimulation pressure (N (Newton)) at which the rat shows a pain-related behaviour (i.e., paw withdrawal, crying, jerks and shaking, or the like) as a result of pressure stimulation on the temporal region in gastrocnemius muscle was measured. The results are shown in FIG. 11.

Figure 11:
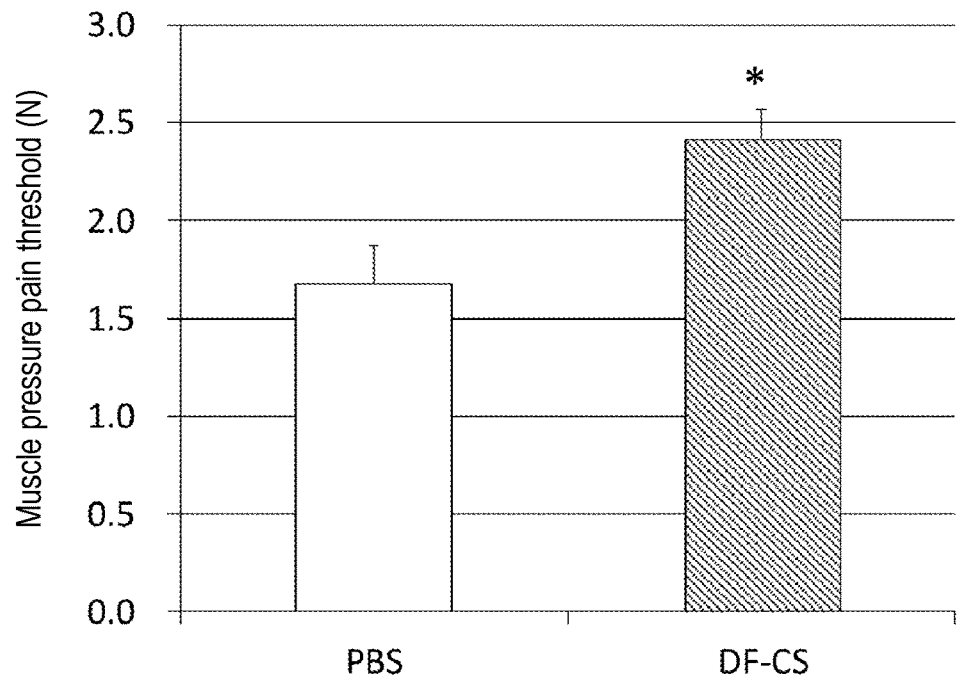
FIG. 11 is a graph illustrating the effect of a diclofenac coupled chondroitin sulfate on muscle pressure pain threshold in a rat model of muscle pain disorder which is caused by carrageenan.

In FIG. 11, the results are shown as the average stimulation pressure±standard error (number of samples for each group=6 or 7). Furthermore, * represents, in the t test, *p<0.05 (vs Control).

B8-3. Results

From FIG. 11, it was found that, by 1% DF-CS which has been applied 7 days ago by intramuscular administration, the muscle pressure pain threshold value was increased in a significant sense.

B8-4. Conclusion

It was evident that the analgesic effect is exhibited for 7 days by 1% DF-CS which has been applied by intramuscular administration.

<Test Example B9> Determination of Effect of Diclofenac Coupled Chondroitin Sulfate in Rat Model of Muscle Pain Disorder that is Caused by Carrageenan

B9-1. Object

According to the object of determining the influence of a difference in coupling mode of chondroitin sulfate derivative, to which the nonsteroidal anti-inflammatory drug (NSAID) has been introduced, on efficacy, the analgesic effects of diclofenac coupled chondroitin sulfates (DF-(Me)-CS, DF-(Thr)-CS and DF-(Ser)-CS) with different spacer coupling mode were evaluated 10 days after the administration by using the above model.

B9-2. Methods

Figure 12:
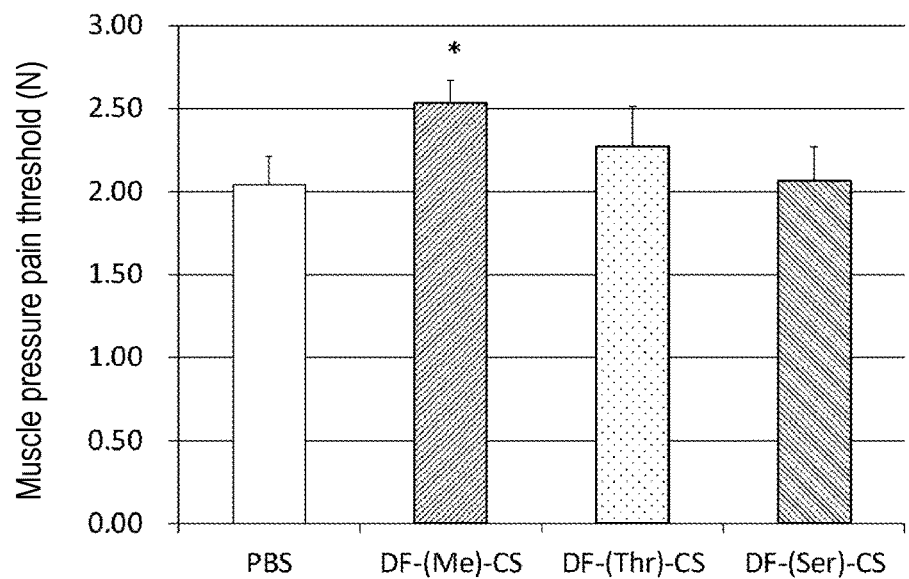
FIG. 12 is a graph illustrating the effect of a diclofenac coupled chondroitin sulfate on muscle pressure pain threshold in a rat model of muscle pain disorder which is caused by carrageenan.
Figure 1:
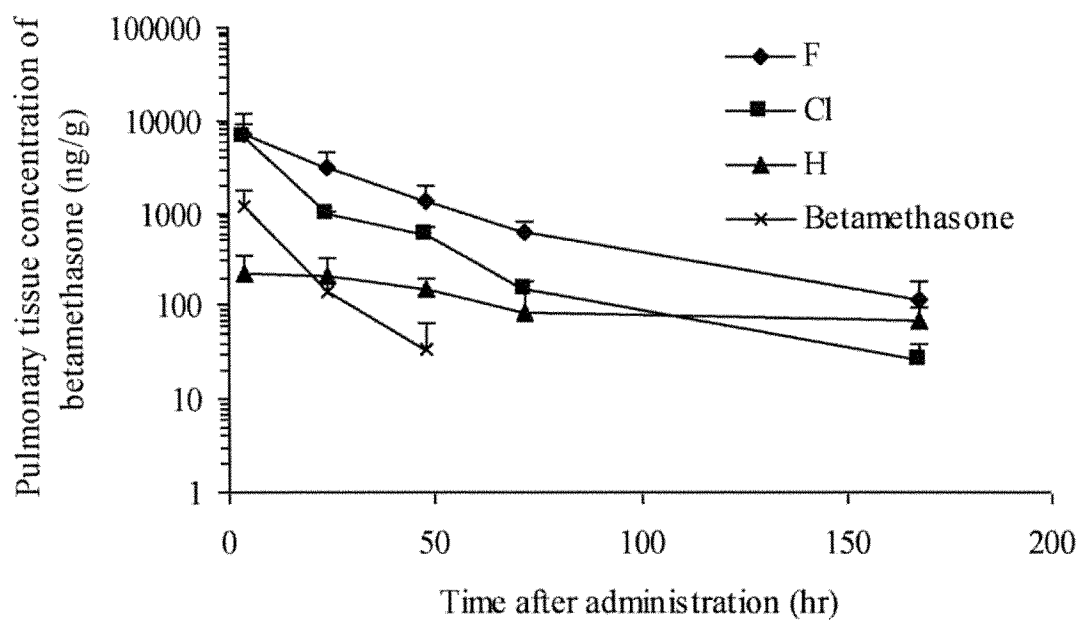
Figure 2:
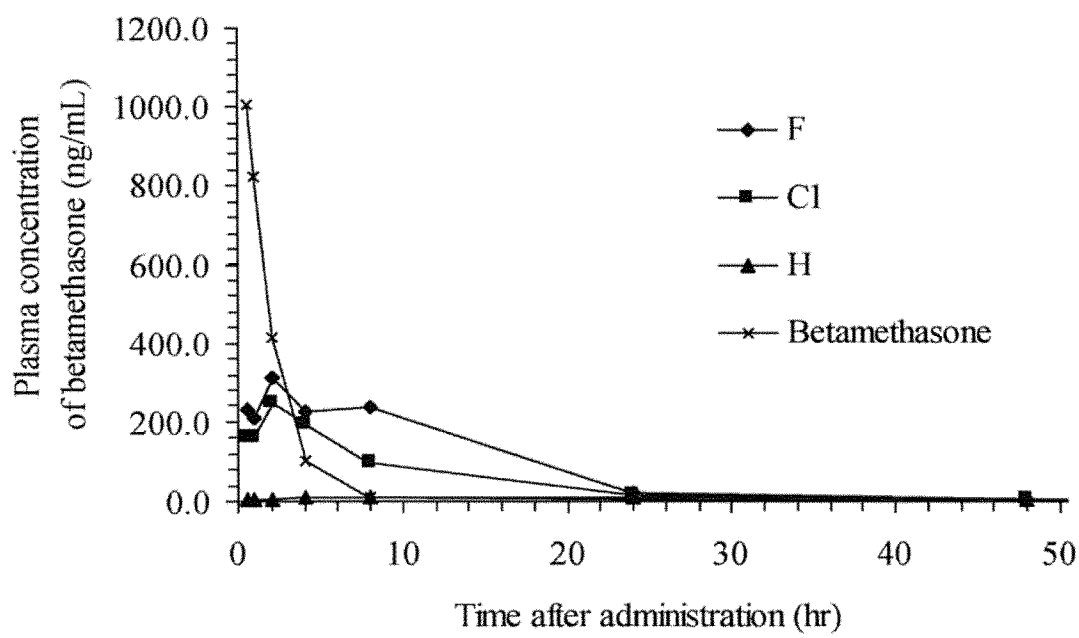

The following were prepared as a test substance in which PBS is used as a solvent.
Test Substance:
(1) PBS (Control)
(2) 1% (w/v %) diclofenac-(1-amino-2-propanol)-chondroitin sulfate (DF-(Me)-CS)
(3) 1% (w/v %) diclofenac (threonine ethyl ester)-chondroitin sulfate (DF-(Thr)-CS)
(4) 1% (w/v %) diclofenac (serine ethyl ester)-chondroitin sulfate (DF-(Ser)-CS)
The experiment was performed according to the experimental order of the above Test example B6. The results are shown in FIG. 12.
In FIG. 12, the results are shown as the average stimulation pressure±standard error (number of samples for each group=8). Furthermore, * represents, in the t test, *p<0.05 (vs Control).

B9-3. Results

From FIG. 12, it was found that, by 1% DF-(Me)-CS which has been applied 10 days ago by intramuscular administration, the muscle pressure pain threshold value was increased in a significant sense compared to the control group.

B9-4. Conclusion

It was concluded that the analgesic effect is exhibited for 10 days by 1% DF-(Me)-CS which has been applied by intramuscular administration.
It was found from the above that, for a case in which diclofenac is selected as a physiologically active substance that is coupled to glycosaminoglycan with a spacer therebetween, a long-acting pain suppressing effect by the glycosaminoglycan derivative can be obtained by using, instead of an electron withdrawing group, a sterically hindered group as a substituent group that is introduced to a coupling group of amino alcohol as a spacer-forming molecule.
Disclosures of Japanese Patent Application No. 2013-144364 (filing date: Jul. 10, 2013) and Japanese Patent Application No. 2013-144365 (filing date: Jul. 10, 2013) are incorporated herein by reference in their entirety.
Regarding all the literatures, patent applications, and technical standards described in the present specification, each of the literatures, patent applications, and technical standards is incorporated herein by reference to the same extent as it is specifically and separately described.

The invention claimed is:
1. A glycosaminoglycan derivative comprising:
a group derived from glycosaminoglycan and a group derived from a physiologically active substance having at least one of a carboxy group and a hydroxy group that are coupled by a covalent bond with a spacer therebetween, in which the spacer is selected in accordance with a decomposition rate of the covalent bond to the group derived from a physiologically active substance;
wherein the glycosaminoglycan is at least one selected from the group consisting of a chondroitin sulfate, a hyaluronic acid, a heparin, a heparan sulfate, a keratan sulfate, a dermatan sulfate, and a derivative thereof;
wherein the group derived from the physiologically active substance and the spacer are covalently bonded through an ester bond;
wherein the group derived from glycosaminoglycan and the spacer are covalently bonded through an amide bond;
wherein the spacer is a divalent group derived from an amino acid represented by the following formula (I):

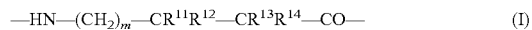

$$-HN-(CH_2)_m-CR^{11}R^{12}-CR^{13}R^{14}-CO- \quad (I)$$

wherein in formula (I), m is an integer of 0 to 12 and $R^{11}$ to $R^{14}$ each independently represents a hydrogen atom, an electron withdrawing group, an electron donating group, or a sterically hindered group; and
wherein a dissociation rate of the physiologically active substance from the glycosaminoglycan derivative is 0.1 to 5%/day in a phosphate buffered saline with pH of 7.5 at 36° C.
2. The glycosaminoglycan derivative according to claim 1, wherein the physiologically active substance is at least one selected from the group consisting of a nonsteroidal anti-inflammatory drug, a steroid, an anti-rheumatic drug, an anti-allergic drug, a therapeutic agent for hyperlipidemia, and a 1 stimulator.
3. A pharmaceutical composition comprising the glycosaminoglycan derivative described in claim 1.
4. A controlled release preparation comprising the glycosaminoglycan derivative described in claim 1.
5. A continuous type pain suppressing agent comprising the glycosaminoglycan derivative described in claim 1.
6. A method for producing a glycosaminoglycan derivative, the method comprising:
preparing a physiologically active substance having at least one of a carboxy group or a hydroxy group, selecting a spacer for forming a covalent bond with a group derived from the physiologically active substance in accordance with a decomposition rate of the covalent bond, and
forming a covalent bond between the group derived from the physiologically active substance and a group derived from glycosaminoglycan with the spacer therebetween;
wherein the glycosaminoglycan is at least one selected from the group consisting of a chondroitin sulfate, a hyaluronic acid, a heparin, a heparan sulfate, a keratan sulfate, a dermatan sulfate, and a derivative thereof;
wherein the group derived from the physiologically active substance and the spacer are covalently bonded through an ester bond;
wherein the group derived from glycosaminoglycan and the spacer are covalently bonded through an amide bond;

wherein the spacer is a divalent group derived from an amino acid represented by the following formula (I):

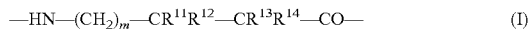

wherein in formula (I), m is an integer of 0 to 12 and $R^{11}$ to $R^{14}$ each independently represents a hydrogen atom, an electron withdrawing group, an electron donating group, or a sterically hindered group; and wherein a dissociation rate of the physiologically active substance from the glycosaminoglycan derivative is 0.1 to 5%/day in a phosphate buffered saline with pH of 7.5 at 36° C.

7. A glycosaminoglycan derivative comprising:

a group derived from glycosaminoglycan, a group derived from a physiologically active substance, and a spacer which couples the group derived from glycosaminoglycan to the group derived from the physiologically active substance by a covalent bond, wherein the glycosaminoglycan is at least one selected from the group consisting of a chondroitin sulfate, a hyaluronic acid, a heparin, a heparan sulfate, a keratan sulfate, a dermatan sulfate, and a derivative thereof, wherein the physiologically active substance has a hydroxy group, a molecule for forming the spacer has a carboxy group corresponding to the hydroxy group, and the group derived from the physiologically active substance and the spacer are covalently bonded through an ester bond, wherein the glycosaminoglycan has a carboxy group, the molecule for forming the spacer has an amino group corresponding to the carboxy group of the glycosaminoglycan, and the group derived from glycosaminoglycan and the spacer are covalently bonded through an amide bond, wherein the molecule for forming the spacer has a coupling group which couples the carboxy group and the amino group and the length of the coupling group between the carboxy group and the amino group is 2 to 12 atoms, and wherein a dissociation rate of the physiologically active substance from the glycosaminoglycan derivative is 0.1 to 5%/day in a phosphate buffered saline with pH of 7.5 at 36° C.

8. The glycosaminoglycan derivative according to claim 1, wherein the physiologically active substance has a hydroxy group.

9. The glycosaminoglycan derivative according to claim 1, wherein the physiologically active substance is a steroid.

10. The glycosaminoglycan derivative according to claim 1, wherein the glycosaminoglycan is at least one selected from the group consisting of chondroitin sulfate and a derivative thereof.

* * * * *

UNITED STATES PATENT AND TRADEMARK OFFICE
CERTIFICATE OF CORRECTION

PATENT NO. : 10,098,962 B2
APPLICATION NO. : 14/903817
DATED : October 16, 2018
INVENTOR(S) : Kenji Miyamoto et al.

It is certified that error appears in the above-identified patent and that said Letters Patent is hereby corrected as shown below:

On the Title Page

Item (56) under FOREIGN PATENT DOCUMENTS, the citation "WO 2004/0157810 A2 3/2004" should read -- WO 2004/017904 A2 3/2004 --.

In the Drawings

Please replace Fig. 2 with Fig. 2 as shown on the attached page.

In the Specification

At Column 3, Line number 6, formula (II) "—HN—(CH2)n—CR21R22—CR23R24—CO—" should read -- —HN—(CH2)n—CR21R22—CR23R24—O— --.

At Column 8, Line number 22, the "," after the word "solution" should be deleted and replaced with a -- . --.

At Column 9, Line number 4, a -- . -- needs to be inserted after the word "like".

At Column 12, Line number 44, "of a" should read -- of α --.

At Column 15, Line number 13, "at a postion" should read -- at α position --.

At Column 15, Line number 17, "at a postion" should read -- at α position --.

At Column 15, Line number 39, the word "pimellic" should read -- pimelic --.

At Column 15, Line number 40, the word "azellaic" should read -- azelaic --.

Signed and Sealed this
Ninth Day of April, 2019

Andrei Iancu
*Director of the United States Patent and Trademark Office*

CERTIFICATE OF CORRECTION (continued)
U.S. Pat. No. 10,098,962 B2

At Column 15, Line number 48, "2-phosphoglyserine acid" should read -- 2-phosphoglycerine acid --.

At Column 15, Line numbers 48-49, "3-phosphoglyserine acid" should read -- 3-phosphoglycerine acid --.

At Column 15, Line number 49, "cereblonic acid" should read -- cerebronic acid --.

At Column 27, Line number 14, a -- . -- should be inserted after "group)".

At Column 28, Line number 22, "$^1$-NMR" should read -- $^1$H-NMR --.

At Column 28, Line number 37, "methylmoprpholinium" should read -- methylmorpholinium --.

At Column 29, Line numbers 15-20, Scheme 2, compound 3, "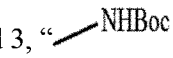" should be replaced with -- 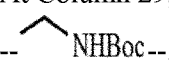 --.

At Column 29, Line numbers 25-30, Scheme 2, compound 4, "" should be replaced with --  --.

At Column 32, Line number 5, "2-chloroacrylonitirile" should read -- 2-chloroacrylonitrile --.

At Column 32, Line number 54, "$^1$-NMR" should read -- $^1$H-NMR --.

At Column 34, Line number 7, "at a postion" should read -- at α position --.

At Column 34, Line numbers 59-61, Scheme 4, compound 20, "" should be replaced with -- 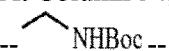 --.

At Column 35, Line numbers 3-5, Scheme 4, compound 21, "" should be replaced with --  --.

At Column 45, Line numbers 15-18, Scheme 7 - continued, compound 44, a -- , -- should be inserted after "CS".

At Column 46, Line number 12, "53.12" should read -- δ3.12 --.

At Column 53, Line numbers 3-5, Scheme 11 - continued, compound 15, "" should read --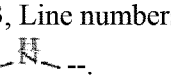 --.

At Column 53, Line number 43, "1H-NMR" should read -- $^1$H-NMR --.

CERTIFICATE OF CORRECTION (continued)

At Column 54, Line numbers 45-48, <u>Scheme 12</u>, compound 19, "  " should read --  --.

At Column 55, Line number 8, "δ6.43" should read -- δ1.43 --.

At Column 57, Line number 11, "(1H, $)" should read -- (1H, s) --.

At Column 61, Line number 25, "Eq" should read -- eq --.

At Column 61, Line number 25, "Mmol" should read -- mmol --.

At Column 61, Line number 25, "Compound" should read -- compound --.

At Column 61, Line number 57, a -- . -- should be inserted after the word "following".

At Column 62, Line number 26, "Dissolved" should read -- dissolved --.

At Column 64, Line number 5, "CDCl3" should read -- CDCl$_3$ --.

At Column 66, Line number 24, the line "60% from the compound 2" should be moved up to the previous line as a continuation of the same paragraph.

At Column 66, Line number 25, a -- . -- should be inserted after the word "following".

At Column 68, Line number 30, a -- . -- should be inserted after the word "following".

At Column 68, Line number 47, a -- . -- should be inserted after the word "following".

At Column 70, Line number 10, "50.93" should read -- δ0.93 --.

At Column 74, Line number 57, "50.96" should read -- δ0.96 --.

At Column 75, Line numbers 54-56, <u>Scheme 21</u>, compound 1, "  " should read --  --.

At Column 88, Line number 23, "(6H, $)" should read -- (6H, s) --.

At Column 91, Line number 24, "50.94" should read -- δ0.94 --.

At Column 91, Line number 26, "4.32 (1H, $)" should read -- 4.32 (1H, s) --.

At Column 91, Line number 26, "6.15 (1H, $)" should read -- 6.15 (1H, s) --.

At Column 91, Line number 27, a -- . -- should be inserted after "(2H, m)".

At Column 91, Line number 43, a -- . -- should be inserted after "(2H, dd)".
At Column 93, Line number 37, "isoclatic" should read -- isocratic --.

CERTIFICATE OF CORRECTION (continued)
U.S. Pat. No. 10,098,962 B2

At Column 94, Line numbers 25-30, TABLE 6, solution E, "(PH 8.1)" should read --(pH 8.1)--.

At Column 97, Line number 46, "isoclatic" should read -- isocratic --.

At Column 100, Line number 32, "isoclatic" should read -- isocratic --.

At Column 107, Line number 39, "intratracheall" should read -- intratracheal --.

At Column 108, Line number 23, a -- . -- should be inserted after "min)".

At Column 116, Line numbers 4-5, "DF-CS 7 days after the adminstration was evaluated using the above model" should be moved up to the previous line as a continuation of the same paragraph.

In the Claims

At Column 118, Claim number 2, Line number 39, "1 stimulator" should read -- β stimulator --.